US011637244B2

(12) United States Patent
Geng et al.

(10) Patent No.: US 11,637,244 B2
(45) Date of Patent: Apr. 25, 2023

(54) LIGHT-EMITTING MATERIAL, COMPOUND, AND ORGANIC LIGHT-EMITTING ELEMENT

(71) Applicants: KYUSHU UNIVERSITY, NATIONAL UNIVERSITY CORPORATION, Fukuoka (JP); KYULUX, INC., Fukuoka (JP)

(72) Inventors: Yan Geng, Fukuoka (JP); Chihaya Adachi, Fukuoka (JP); Hajime Nakanotani, Fukuoka (JP); Naoto Notsuka, Fukuoka (JP); Keiro Nasu, Fukuoka (JP)

(73) Assignees: KYUSHU UNIVERSITY, NATIONAL UNIVERSITY CORPORATION, Fukuoka (JP); KYULUX, INC., Fukuoka (JP)

( * ) Notice: Subject to any disclaimer, the term of this patent is extended or adjusted under 35 U.S.C. 154(b) by 448 days.

(21) Appl. No.: 16/471,231

(22) PCT Filed: Dec. 21, 2017

(86) PCT No.: PCT/JP2017/046017
§ 371 (c)(1),
(2) Date: Jun. 20, 2019

(87) PCT Pub. No.: WO2018/117241
PCT Pub. Date: Jun. 28, 2018

(65) Prior Publication Data
US 2019/0348611 A1 Nov. 14, 2019

(30) Foreign Application Priority Data
Dec. 21, 2016 (JP) .............................. JP2016-247496

(51) Int. Cl.
H01L 51/00 (2006.01)
C09K 11/06 (2006.01)
(Continued)

(52) U.S. Cl.
CPC ........ H01L 51/0067 (2013.01); C07D 251/24 (2013.01); C07D 401/10 (2013.01);
(Continued)

(58) Field of Classification Search
None
See application file for complete search history.

(56) References Cited

U.S. PATENT DOCUMENTS 4,335,136 A * 6/1982 Cherkofsky ......... C07D 207/33
548/161
6,433,184 B1 8/2002 Choi et al.
(Continued)

FOREIGN PATENT DOCUMENTS

CN 101921531 A 12/2010
EP 0866110 A1 9/1998
(Continued)

OTHER PUBLICATIONS

Machine English translation of Fukuda et al. (JP 2004-311413 A). Aug. 17, 2022.*
(Continued)

Primary Examiner — Jay Yang
(74) Attorney, Agent, or Firm — Browdoy and Neimark, PLLC

(57) ABSTRACT

A compound represented by the following general formula is excellent in light emission properties. $R^1$ and $R^2$ each independently represent a fluorinated alkyl group, D represents a substituent in which Hammett's $\sigma_p$ value is negative, and A represents a substituent in which Hammett's $\sigma_p$ value is positive.

(Continued)

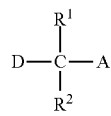

15 Claims, 13 Drawing Sheets

(51) Int. Cl.
*C09K 11/02* (2006.01)
*C07D 401/10* (2006.01)
*C07D 251/24* (2006.01)
*H01L 51/50* (2006.01)

(52) U.S. Cl.
CPC .............. *C09K 11/02* (2013.01); *C09K 11/06* (2013.01); *H01L 51/0061* (2013.01); *H01L 51/0072* (2013.01); *C09K 2211/1007* (2013.01); *C09K 2211/1018* (2013.01); *C09K 2211/1022* (2013.01); *H01L 51/5012* (2013.01); *H01L 51/5016* (2013.01); *H01L 51/5096* (2013.01)

(56) References Cited

U.S. PATENT DOCUMENTS

2012/0248968 A1\* 10/2012 Ogiwara ............. H01L 51/0059
    313/504
2013/0256645 A1 10/2013 Min et al.

FOREIGN PATENT DOCUMENTS

| JP | S63-051415 | | 3/1983 |
| JP | H4-117424 | A | 4/1992 |
| JP | H10-251633 | A | 9/1998 |
| JP | 2001-019767 | A | 1/2001 |
| JP | 2004-288380 | A | 10/2004 |
| JP | 2004-311413 | A | 11/2004 |
| JP | 2004-311424 | A | 11/2004 |
| JP | 2005-085658 | A | 3/2005 |
| JP | 2008-231127 | A | 10/2008 |
| JP | 2016-017078 | A | 2/2016 |
| JP | 2017-222623 | A | 12/2017 |
| KR | 10-0729737 | B1 | 6/2007 |
| WO | 2013/011955 | A1 | 1/2013 |
| WO | 2013/154064 | A1 | 10/2013 |
| WO | 2014/133121 | A1 | 9/2014 |
| WO | 2015/072470 | A1 | 5/2015 |

OTHER PUBLICATIONS

Partial Supplementary European Search Report dated Jun. 18, 2020 issued in the corresponding European Patent Application No. 17883485. 9.
Office Action dated Oct. 1, 2021 issued in the corresponding European patent Application No. 17883485.9.
Office Action dated Oct. 5, 2021 issued in the corresponding Japanese patent Application No. 2017-244764 with its English Machine Translation.
Extended European Search Report dated Sep. 29, 2020 from European Patent Application No. 17883485.9.
International Preliminary Report On Patentability of Chapter I/II, i.e., International Search Opinion for corresponding PCT International Application No. PCT/JP2017/046017, dated Apr. 3, 2019, with English translation.
International Search Report and Search Opinion for corresponding PCT International Application No. PCT/JP2017/046017 dated Apr. 4, 2018.
Tigelaar et al., Study of the incorporation of protic ionic liquids into hydrophilic and hydrophobic rigid-rod elastomeric polymers, Polymer, 47(12)4269-4275 (2006).
Walree et al., Comparison between SiMe2 and CMe2 spacers as—Bridges for photoinduced charge transfer, J. Am. Chem. Soc.,, 118:8395-8407 (1996).
Uoyama et al., Highly efficient organic light-emitting diodes from delayed fluorescence, Nature, 492:234-238 (2012).
Hansch et al., A Survey of Hammett Substituent Constants and Resonance and Field Parameters, Chem. Rev., 91:165-195 (1991).
Office Action dated Jun. 8, 2022 issued in the corresponding Korean patent Application No. 10-2019-7018175 with its English Machine Translation.
Office Action dated Aug. 26, 2022 issued in the corresponding Chinese patent application No. 201780079513.8 with ts English Machine Translation.

\* cited by examiner

LIGHT-EMITTING MATERIAL, COMPOUND, AND ORGANIC LIGHT-EMITTING ELEMENT

TECHNICAL FIELD

The present invention relates to a compound useful as a light-emitting material and an organic light-emitting element using thereof.

BACKGROUND ART

Studies for enhancing light emission efficiency of an organic light-emitting element such as an organic electroluminescence element (organic EL element) has been actively performed. In particular, as a result of energetically proceeding examination of a molecular structure focused on charge movement or energy state in molecule with respect to an organic compound as a light-emitting material, several compound groups capable of obtaining high light emission efficiency were found.

For example, as such a compound group, a compound group having a structure in which a donor group and an acceptor group are linked to each other is proposed. If the compound having this structure comes to an excited state due to rebonding energy of a carrier supplied from each electrode of the organic electroluminescence element, electrons move from the donor group to the acceptor group. After that, the compound that has come to the excited state is deactivated while emitting light, and at the same time, the electrons that have moved to the acceptor group return to the acceptor group. In this manner, the compound included in the compound group has a property in which electrons come and go between the donor group and the acceptor group depending on the energy state, and changes the chemical structure or the disposition of the donor group or the acceptor group, and thus it is possible to control various energy levels. With this, it is possible to remarkably improve light emission efficiency (NPL 1).

CITATION LIST

Non-Patent Literature

[NPL 1] Nature 492, 234-238

SUMMARY OF INVENTION

Technical Problem

The present inventors evaluated light emission properties of various compounds having a structure in which a donor group and an acceptor group are linked to each other, and clearly checked that the compounds have a common advantage of realizing a unique energy state that cannot be obtained by either of the donor group or the acceptor group. However, it was found that the light emission properties significantly vary by the structure of a linking portion that links the donor group and the acceptor group, and thus it is not necessarily possible to provide a favorable light-emitting material simply by linking the donor group and the acceptor group.

With this, the present inventors proceeded intensive studies for the purpose of obtaining a general formula of a compound excellent in light emission properties by having a donor group and an acceptor group and generalizing a structure of an organic light-emitting element with high light emission efficiency.

Solution to Problem

As a result of proceeding intensive studies, the present inventors found that if a linking group having a specific structure is employed as a linking group of linking the donor group and the acceptor group, excellent light emission properties are exhibited. Here, it was found that the compound having a structure in which the donor group and the acceptor group are linked by the specific linking group is a useful compound of emitting delayed fluorescence. In addition, the present inventors obtained a founding that it is possible to provide an organic light-emitting element with high light emission efficiency by using such a compound in a light-emitting material. The present invention has been proposed based on the founding and specifically has the following structure.

[1] A light-emitting material including a compound represented by the following general formula (1).

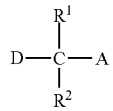

General formula (1)

In the general formula (1), $R^1$ and $R^2$ each independently represent a fluorinated alkyl group, D represents a substituent in which Hammett's $\sigma_p$ value is negative, and A represents a substituent in which Hammett's $\sigma_p$ value is positive.

[2] The light-emitting material according to [1], in which $R^1$ and $R^2$ each independently represent a perfluoroalkyl group.

[3] The light-emitting material according to [1] or [2], in which $R^1$ and $R^2$ each independently have any of 1 to 3 carbon atoms.

[4] The light-emitting material according to any one of [1] to [3], in which D has a substituted or non-substituted diarylamino structure.

[5] The light-emitting material according to [4], in which D is an aryl group substituted with a substituted or non-substituted diarylamino group.

[6] The light-emitting material according to any one of [1] to [5], in which A includes a substituted or non-substituted heteroaryl group.

[7] The light-emitting material according to [6], in which A is an aryl group substituted with a substituted or non-substituted heteroaryl group.

[8] A host material including a compound represented by the general formula (1).

[9] A positive hole blocking material including a compound represented by the general formula (1).

[10] An electron blocking material including compound represented by the general formula (1).

[11] A compound represented by the general formula (1).

[12] A delayed fluorescent body having a structure represented by the general formula (1).

[13] An organic light-emitting element including a compound represented by the general formula (1).

[14] The organic light-emitting element according to [13], having a light-emitting layer including the compound.

[15] The organic light-emitting element according to [14], in which a content of the compound in the light-emitting layer is less than 50% by weight, and the light-emitting layer includes a host material in addition to the compound.

[16] The organic light-emitting element according to [14], in which a content of the compound in the light-emitting layer is equal to or more than 50% by weight, and the light-emitting layer includes a light-emitting material in addition to the compound.

[17] The organic light-emitting element according to any one of [13] to [16], in which an anode, a plurality of organic layers including a light-emitting layer, and a cathode are stacked in order, and the compound is included in a layer in contact with a cathode side of the light-emitting layer.

[18] The organic light-emitting element according to any one of [13] to [16], in which the anode, the plurality of organic layers including a light-emitting layer, and the cathode are stacked in order, and the compound is included in a layer in contact with an anode side of the light-emitting layer.

[19] The organic light-emitting element according to any one of [13] to [18], emitting delayed fluorescence.

Advantageous Effects of Invention

The compound of the present invention has an electron-donating group and an electron-attracting group, and exhibits excellent light emission properties. For this reason, the compound of the present invention is useful as a light-emitting material. In addition, the compound of the present invention includes a material emitting delayed fluorescence. The organic light-emitting element using the compound of the present invention as a light-emitting material realizes high light emission efficiency.

DESCRIPTION OF EMBODIMENTS

Figure 1:
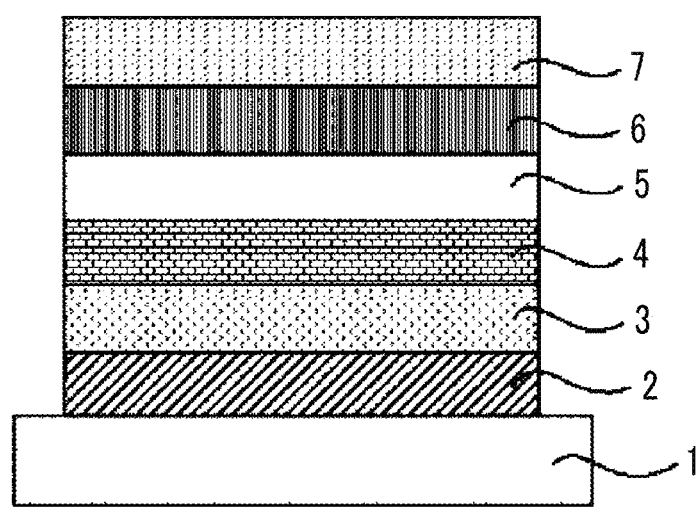
FIG. 1 is a schematic sectional view illustrating a layer configuration example of an organic electroluminescence element.

Hereinafter, the present invention will be described in detail. Explanation of constituent conditions to be described is based on representative embodiments or specific examples of the present invention, but the present invention is not limited to the embodiments or the specific examples. A numerical value range represented by using "to" in the present specification means a range including a numerical value described before and after the "to" as a lower limit value or an upper limit value. In addition, the kind of isotopes of a hydrogen atom present in molecule of a compound used in the present invention is not particularly limited. For example, all of the hydrogen atoms in molecule may be $^1$H, or a part or the entirety may be $^2$H (deuterium D).

[Compound Represented by General Formula (1)]

A light-emitting material of the present invention includes a compound represented by the following general formula (1).

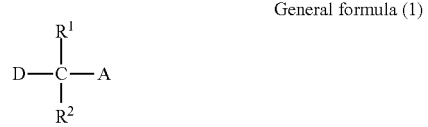

General formula (1)

In the general formula (1), $R^1$ and $R^2$ each independently represent a fluorinated alkyl group. The "fluorinated alkyl group" in the present invention refers to a group having a structure in which at least one of hydrogen atoms of the alkyl group is substituted with a fluorine atom. The fluorinated alkyl groups represented by $R^1$ and $R^2$ may be perfluoroalkyl groups in which all hydrogen atoms of the alkyl group are substituted with fluorine atoms, or may be partially fluorinated alkyl groups in which only a part of hydrogen atoms of the alkyl group is substituted with fluorine atoms. Among these, the fluorinated alkyl group is preferably a perfluoroalkyl group. The fluorinated alkyl group preferably has any of 1 to 20 carbon atoms, more preferably has any of 1 to 10 carbon atoms, further more preferably has any of 1 to 5 carbon atoms, and particularly preferably has any of 1 to 3 carbon atoms. When the fluorinated alkyl group has equal to or more than 3 carbon atoms, the fluorinated alkyl group may be straight-chain, or may be branched. The fluorinated alkyl groups represented by $R^1$ and $R^2$ may be the same as each other, or may be different from each other. As an example of a case where the fluorinated alkyl groups represented by $R^1$ and $R^2$ are different from each other, a case where the number of carbon atoms or fluorine atoms is different, a case where the fluorinated alkyl groups are straight-chain or branched, a case where the number of branches or the position of branches in the branched fluorinated alkyl groups are different, and the like can be exemplified.

D represents a substituent in which Hammett's $\sigma_p$ value is negative, and A represents a substituent in which Hammett's $\sigma_p$ value is positive. Here, the "Hammett's $\sigma_p$ value" is a value proposed by L. P. Hammett, and influence of the substituent on a reaction rate or equilibrium of a para-substituted benzene derivative is quantified. Specifically, the value is a constant ($\sigma_p$) specific to a substituent in the following formula: $\log (k/k0) = \rho\sigma_p$ or $\log (K/K_0) = \rho\sigma_p$ between a substituent and a reaction rate constant or equilibrium constant in the para-substituted benzene derivative. In the above formula, k represents a rate constant of a benzene derivative having no substituent, $k_0$ represents a rate constant of a benzene derivative substituted with a substituent, K represents an equilibrium constant of a benzene derivative having no substituent, $K_0$ represents an equilibrium constant of a benzene derivative substituted with a substituent, and $\rho$ represents a reaction constant determined by the kind and the condition of reaction. Regarding explanation related to the "Hammett's $\sigma_p$ value" in the present invention and a numerical value of each substituent, description related to the $\sigma_p$ value of Hansch, C. et. Al., Chem. Rev., 91, 165-195 (1991) can be referred to. There is a tendency that a substituent in which Hammett's $\sigma_p$ value is negative exhibits electron-donating properties (donor properties), and a substituent in which Hammett's $\sigma_p$ value is positive exhibits electron-attracting properties (acceptor properties). In the following explanation, "Hammett's $\sigma_p$ value being negative" refers to "electron-donating properties", and "Hammett's $\sigma_p$ value being positive" refers to "electron-attracting properties".

As the substituent in which Hammett's $\sigma_p$ value represented by D is negative, an electron-donating substituent bonded by a hetero atom selected from the group consisting of a nitrogen atom, an oxygen atom, a sulfur atom, a silicon atom, and a phosphorus atom, or an aryl group exhibiting electron-donating properties is preferably employed. The aryl group exhibiting electron-donating properties is generally a substituted aryl group, and is preferably an aryl group substituted with an electron-donating substituent bonded by a hetero atom selected from the group consisting of a nitrogen atom, an oxygen atom, a sulfur atom, a silicon atom, and a phosphorus atom.

In addition, the substituent in which Hammett's $\sigma_p$ value represented by D is negative preferably has a substituted or non-substituted diarylamino structure, and is more preferably an aryl group substituted with a substituted or non-substituted diarylamino group. Here, the "diarylamino structure" means both of a heteroaromatic ring structure forming a heterocyclic ring by linking a diarylamino group and an aryl group of the diarylamino group by a single bond and a heteroaromatic ring structure forming a heterocyclic ring by linking a diarylamino group and an aryl group of the diarylamino group by a linking group. An aromatic ring constituting each aryl group having a diarylamino structure and an aromatic ring constituting each aryl group (each aryl group of diarylamino group and aryl group substituted with diarylamino group) of the aryl group substituted with the diarylamino group may be a single ring, may be a condensed ring obtained by condensing two or more aromatic rings, or may be a linking ring obtained by linking two or more aromatic rings. In a case where two or more aromatic rings are linked, the aromatic rings may be linked in a straight-chain shape, or may be linked in a branched shape. The aromatic ring constituting the diarylamino structure and each aryl group of the aryl groups substituted with a diarylamino group preferably has 6 to 22 carbon atoms, more preferably has 6 to 18 carbon atoms, further more preferably has 6 to 14 carbon atoms, and even further more preferably has 6 to 10 carbon atoms. As a specific example of the each aryl group, a phenyl group, a naphthyl group, and a biphenyl group can be exemplified. Regarding explanation and a preferable range of the diarylamino structure and the substituent in a case where the aryl group substituted with a diarylamino group has a substituent, explanation and a preferable range of a substituent group represented by the following $R^{11}$ to $R^{20}$ can be referred to. Regarding explanation and a preferable range of a linking group linking aryl groups in a case where the diarylamino structure is the heteroaromatic ring structure, explanation and a preferable range of a linking group in a case of forming a linking group obtained by bonding $R^{15}$ and $R^{16}$ of the following general formula (2) with each other can be referred to.

The substituent in which Hammett's $\sigma_p$ value represented by D is preferably an electron-donating group represented by the following general formula (2).

General formula (2)

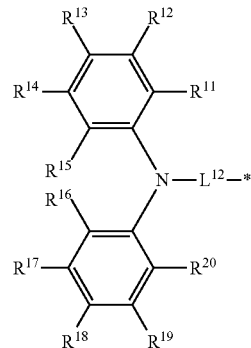

In the general formula (2), $R^{11}$ to $R^{20}$ each independently represent a hydrogen atom or a substituent. The number of the substituents is not limited, and all of $R^{11}$ to $R^{20}$ may be non-substituent (that is, hydrogen atom). In a case where two or more of $R^{11}$ to $R^{20}$ are substituents, a plurality of the substituents may be the same or different.

Examples of the substituent represented by $R^{11}$ to $R^{20}$ include a hydroxy group, a halogen atom, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an alkyl-substituted amino group having 1 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkylamide group having 2 to 20 carbon atoms, an arylamide group having 7 to 21 carbon atoms, a trialkylsilyl group having 3 to 20 carbon atoms, and the like. Among these specific examples, a group capable of being substituted with a substituent may be further substituted. More preferable substituents are an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an aryl-substituted amino group having 1 to 20 carbon atoms, an aryl group having 6 to 40 carbon atoms, a heteroaryl group having 3 to 40 carbon atoms.

$R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may be bonded to each other to form a ring structure. The ring structure may be an aromatic ring or may be an aliphatic ring. In addition, the ring structure may include a hetero atom, and the ring structure may be a condensed ring of two or more rings. Here, the hetero atom is preferably selected from the group consisting of a nitrogen atom, an oxygen atom, and a sulfur atom. Examples of the formed ring structure include a benzene ring, a naphthalene ring, a pyrridine ring, a pyridazine ring, a pyrimidine ring, a pyrazine ring, a pyrrole ring, an imidazole ring, a pyrazole ring, an imidazoline ring, an oxazole ring, an isoxazole ring, a thiazole ring, an isothiazole ring, a cyclohexadiene ring, a cyclohexene ring, a cyclopentadiene ring, a cycloheptatriene ring, a cycloheptadiene ring, a cycloheptaene ring, and the like.

Among the groups represented by the general formula (2), a group in which $R^{15}$ and $R^{16}$ are not bonded to each other, a group in which $R^{15}$ and $R^{16}$ are bonded to each other, or a group in which $R^{15}$ and $R^{16}$ are bonded to each other to form a linking group of which linking chain length is 1 atom is preferable. In a case where $R^{15}$ and $R^{16}$ are bonded to each other to form a linking group of which linking chain length is one atom, a ring structure formed as a result of bonding $R^{15}$ and $R^{16}$ to each other is a six-membered ring. Specific examples of the linking group formed by bonding $R^{15}$ and $R^{16}$ to each other include a linking group represented by —O—, —S—, —N($R^{91}$)—, or —C($R^{92}$)($R^{93}$)—. Here, $R^{91}$ to $R^{93}$ each independently represent a hydrogen atom or a substituent. Examples of the substituent represented by $R^{91}$ include an alkyl group having 1 to 20 carbon atoms, an aryl group having 6 to 40 carbon atoms, and a heteroaryl group having 3 to 40 carbon atoms. As the substituents represented by $R^{92}$ and $R^{93}$, each independently, a hydroxy group, a halogen atom, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an aryl-substituted amino group having 1 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkylamide group having 2 to 20 carbon atoms, an arylamide group having 7 to 21 carbon atoms, a trialkylsilyl group having 3 to 20 carbon atoms, and the like can be exemplified.

In the general formula (2), $L^{12}$ represents a single bond, a substituted or non-substituted an arylene group, or a substituted or non-substituted heteroarylene group. * represents a bonding position to a carbon atom (C) in the general formula (1). $L^{12}$ is preferably a single bond or a substituted or non-substituted arylene group.

An aromatic ring constituting an arylene group represented by $L^{12}$ may be a single ring, may be a condensed ring in which two or more aromatic rings are condensed, or may be a linking ring in which two or more aromatic rings are linked. In a case where two or more aromatic rings are linked, the aromatic ring may be a ring linked in a straight chain, or may be a ring linked in a branched shape. The aromatic ring constituting an arylene group represented by $L^{12}$ preferably has 6 to 22 carbon atoms, more preferably has 6 to 18 carbon atoms, further more preferably has 6 to 14 carbon atoms, and even further more preferably has 6 to 10 carbon atoms. Specific examples of the arylene group include a phenylene group, a naphthalenediyl group, and a biphenylene group. In addition, a heterocyclic ring constituting a heteroarylene group represented by $L^{12}$ may be a single bond, may be a condensed ring in which one or more heterocyclic rings and an aromatic ring or a heterocyclic ring are condensed, or may be a linking ring in which one or more heterocyclic rings and an aromatic ring or a heterocyclic ring are linked. The heterocyclic ring preferably has 5 to 22 carbon atoms, more preferably has 5 to 18 carbon atoms, further more preferably has 5 to 14 carbon atoms, and even further more preferably has 5 to carbon atoms. The heterocyclic atom constituting a heterocyclic ring is preferably a nitrogen atom. Specific examples of the heterocyclic ring include a pyridine ring, a pyridazine ring, a pyrimidine ring, a triazole ring, and a benzotriazole ring. A preferable ring represented by is a phenylene group. When $L^{12}$ is a phenylene group, the phenylene group may be any of a 1,2-phenylene group, a 1,3-phenylene group, and a 1,4-phenylene group, but is preferably the 1,4-phenylene group. In addition, $L^{12}$ may be substituted with a substituent. The number and the substitution position of the substituents of $L^{12}$ are not particularly limited. Regarding explanation and a preferable range of the substituent introduced into $L^{12}$, explanation and a preferable range of the substituents represented by $R^{11}$ to $R^{20}$ can be referred to.

Preferable examples of the group represented by the general formula (2) include a group represented by any of the following general formulae (4) to (8).

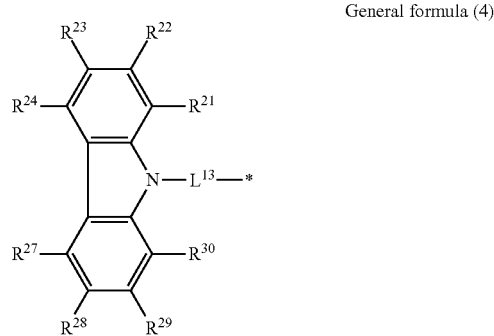

General formula (4)

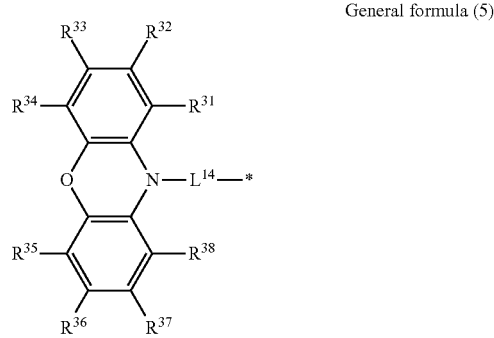

General formula (5)

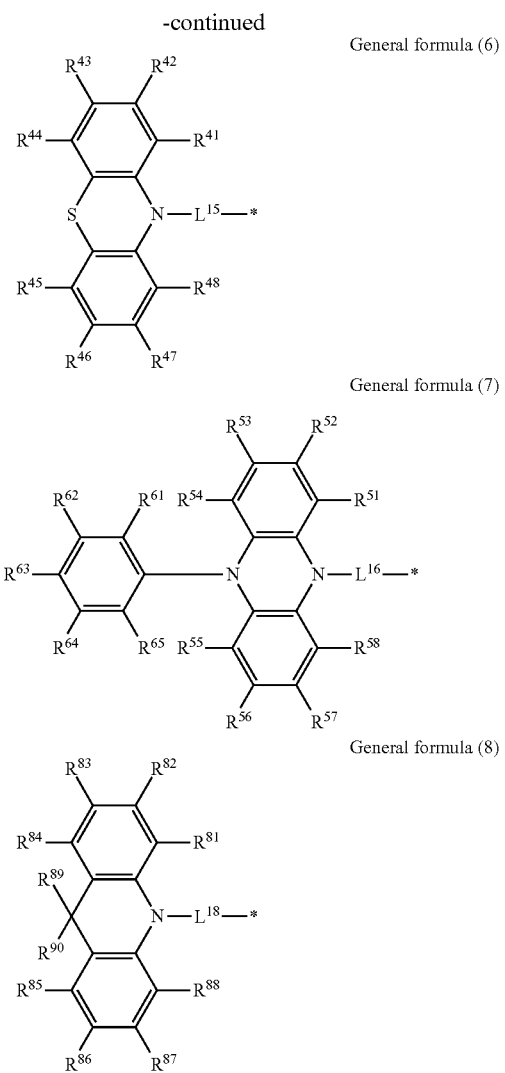

General formula (6)

General formula (7)

General formula (8)

In the general formulae (4) to (8), $R^{21}$ to $R^{24}$, $R^{27}$ to $R^{38}$, $R^{41}$ to $R^{48}$, $R^{51}$ to $R^{58}$, $R^{61}$ to $R^{65}$, $R^{81}$ to $R^{90}$ each independently represent a hydrogen atom or a substituent. Here, regarding explanation and a preferable range of the substituent, explanation and a preferable range of the substituents represented by $R^{11}$ to $R^{20}$ can be referred to. $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, and $R^{81}$ to $R^{90}$ each independently is preferably a group represented by any of the general formulae (4) to (8). In addition, at least two of $R^{21}$, $R^{23}$, $R^{28}$, and $R^{30}$ of the general formula (4) is preferably a substituted or a non-substituted alkyl group, but it is more preferably that all of $R^{21}$, $R^{23}$, $R^{28}$, and $R^{30}$ are substituted or non-substituted alkyl groups, $R^{21}$ and $R^{30}$ are substituted or non-substituted alkyl groups, or $R^{23}$ and $R^{28}$ are substituted or non-substituted alkyl groups. In addition, the substituted or non-substituted alkyl groups are more preferably substituted or non-substituted alkyl groups having 1 to 6 carbon atoms. $R^{89}$ and $R^{90}$ of general formula (8) are preferably substituted or non-substituted alkyl groups, and more preferably substituted or non-substituted alkyl groups having 1 to 6 carbon atoms. The number of the substituents in the general formulae (4) to (8) is not particularly limited. A case where all are non-substituted (that is, hydrogen atom) is also preferable. In addition, in a case where the number of the substituents in each of the general formulae (4) to (8) is 2 or more, the substituents may be the same or different. In a case where there is a substituent in the general formulae (4) to (8), the substituent is preferably any of $R^{22}$ to $R^{24}$ and $R^{27}$ to $R^{29}$, and more preferably at least one of $R^{23}$ and $R^{29}$ in a case of the general formula (4), the substituent is preferably any of $R^{32}$ to $R^{37}$ in a case of the general formula (5), the substituent is preferably any of $R^{42}$ to $R^{47}$ in a case of the general formula (6), the substituent is preferably any of $R^{52}$, $R^{53}$, $R^{56}$, $R^{57}$, and $R^{62}$ to $R^{64}$ in a case of the general formula (7), and the substituent is preferably any of $R^{82}$ to $R^{87}$, $R^{89}$, and $R^{90}$ in a case of the general formula (8).

In the general formulae (4) to (8), $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ may be bonded to each other to form a ring structure. Regarding explanation and a preferable range of the ring structure, explanation and a preferable range of the ring structure formed by R11 and R12 and the like being bonded to each other in the general formula (2) can be referred to.

In the general formulae (4) to (8), $L^{13}$ to $L^{16}$ and $L^{18}$ represent a single bond, a substituted or non-substituted alkyl group, or a substituted or non-substituted heteroarylene group. * represents a bonding position to a carbon atom (C) in the general formula (1). Regarding explanation and a preferable range of the arylene group or the heteroarylene group represented by $L^{13}$ to $L^{16}$ and $L^{18}$, and a substitutent introduced into the group, explanation and a preferable range of the arylene group or the heteroarylene group represented by $L^{12}$, and a substituent introduced into the group can be referred to. $L^{13}$ to $L^{16}$ and $L^{18}$ are preferably single bonds and substituted or non-substituted arylene groups.

The substituent in which Hammett's $\sigma_p$ value represented by D is negative is preferably an electron-donating group represented by the following general formula (3), for example.

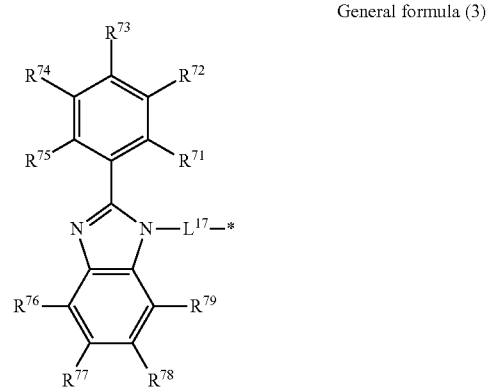

General formula (3)

In the general formula (3), $R^{71}$ to $R^{79}$ each independently represent a hydrogen atom or a substituent. $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, and $R^{78}$ and $R^{79}$ may be bonded to each other to form a ring structure. $L^{17}$ represents a single bond, a substituted or non-substituted arylene group, or a substituted or non-substituted heteroarylene group. * represents a bonding position to a carbon atom (C) in the general formula (1).

Regarding explanation and a preferable range of the substituent represented by $R^{71}$ to $R^{79}$, explanation and a preferable range of the substituents represented by $R^{11}$ to $R^{20}$ can be referred to. In addition, $R^{71}$ to $R^{79}$ each independently are a group represented by any of the general formulae (4) to (8). In a case where there is a substituent, the substitution position is preferably any of $R^{72}$ to $R^{74}$, $R^{77}$, and $R^{78}$.

Regarding explanation and a preferable range of the arylene group or the heteroarylene group represented by $L^{17}$, and a substituent introduced into the group, explanation and a preferable range of the arylene group or the heteroarylene group represented by $L^{12}$, and a substituent introduced into the group can be referred to.

The substituent in which Hammett's $\sigma_p$ value represented by A is positive preferably includes a substituted or non-substituted heteroaryl group, and is more preferably an aryl group substituted with a substituted or non-substituted heteroaryl group. In a case where A includes a substituted or non-substituted heteroaryl group, an aromatic heterocyclic ring included in the heteroaryl group is preferably a π-electron-deficient aromatic heterocyclic ring. Examples of the hetero atom included in the heteroaryl group include a nitrogen atom, an oxygen atom, a sulfur atom, and a boron atom, and the heteroaryl group preferably includes at least one nitrogen atom as a ring. As the heteroaryl group, a group formed of 5 rings or 6 rings including a nitrogen atom as a ring, or a group having a structure in which a benzene ring is condensed in 5 rings or 6 rings including a nitrogen atom as a ring can be exemplified, and is preferably a monovalent group obtained by excluding one hydrogen atom from a pyridine ring, a pyrazine ring, a pyrimidine ring, a pyridazine ring, and a triazine ring, or a group having a structure in which the aromatic heterocyclic rings are shrunk and a group having a structure in which the aromatic heterocyclic rings are shrunk. In addition, examples of the substituent in a case where the heteroaryl group has a substituent include an alkyl group having 1 to 20 carbon atoms, an aryl group having 6 to 40 carbon atoms, a cyano group, a halogen atom, a heteroaryl group having 5 to 40 carbon atoms, and the like. A substituent capable of being substituted with a substituent among the substituents may be substituted.

In a case where A is an aryl group substituted with a substituted or non-substituted heteroaryl group, an aromatic ring constituting the aryl group (aryl group substituted with heteroaryl group) may be a single ring, a condensed ring in which two or more aromatic rings are condensed, or a linking ring in which two or more aromatic rings are linked. In a case where two or more aromatic rings are linked, the aromatic rings may be linked in a straight chain shape or may be linked in a branched shape. The aromatic ring constituting the aryl group preferably has 6 to 22 carbon atoms, more preferably has 6 to 18 carbon atoms, further more preferably has 6 to 14 carbon atoms, and even further more preferably has 6 to 10 carbon atoms. Specific examples of the aryl group include a phenyl group, a naphthyl group, and a biphenyl group. Regarding explanation and a preferable range of a substituent in a case where the aryl group has a substituent in addition to the heteroaryl group, explanation and a preferable range of a substituent introduced into a group represented by $L^{12}$ can be referred to.

The substituent in which Hammett's $\sigma_p$ value represented by A is positive is preferably a group represented by the following general formula (9).

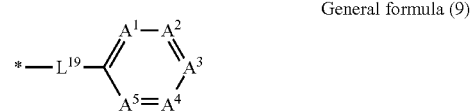

General formula (9)

In the general formula (9), $A^1$ to $A^5$ each independently represent N or $C(R^{19})$, and $R^{19}$ represents a hydrogen atom or a substituent. It is preferable that at least one of $A^1$ to $A^5$ is N, and it is more preferable that one to three of $A^1$ to $A^5$ are N, and it is further more preferable that three to five of $A^1$ to $A^5$ are N. When a group represented by the general formula (9) has a plurality of $R^{19}$, the plurality of $R^{19}$ may be the same as one another or different from one another. Examples of the substituent represented by $R^{19}$ include an alkyl group having 1 to 20 carbon atoms, an aryl group having 6 to 40 Carbon atoms, a cyano group, a halogen atom, a heteroaryl group having 5 to 40 carbon atoms, and the like for example, and is preferably the aryl group laving 6 to 40 carbon atoms. The substituent capable of being substituted with a substituent among the substituents may be substituted.

In the general formula (9), $L^{19}$ represents a single bond, a substituted or non-substituted arylene group, or a substituted or non-substituted heteroarylene group. * represents a bonding position to a carbon atom (C) in the general formula (1). Regarding explanation and a preferable range of an arylene group or a heteroarylene group represented by $L^{19}$, or a substituent introduced into the group, explanation and a preferable range of the arylene group or the heteroarylene group represented by $L^{12}$, or a substituent introduced into the group can be referred to $L^{19}$ is preferably a substituted or non-substituted arylene group, more preferably a substituted or non-substituted phenylene group, and further more preferably a non-substituted phenylene group. When $L^{19}$ is a substituted or non-substituted phenylene group, the phenylene group may be any of a 1,2-phenylene group, a 1,3-phenylene group, and a 1,4-phenylene group, the phenylene group is preferably the 1,4-phenylene group.

In the following description, specific examples (A-1 to A-77) of the substituents included in A will be exemplified. However, in the present invention, the substituent in which Hammett's $\sigma_p$ value represented by A is positive should not be limitedly interpreted as including the substituents. The substituent in which Hammett's $\sigma_p$ value represented by A is positive may be a substituent represented by any of A-1 to A-77, or may be constituted of a substituent represented by any of A-1 to A-77 and a linking group linking the substituent to the carbon atom (C) of the general formula (1). In the following formula, * represents a bonding position to the carbon atom (C) of the general formula (1), or a bonding position to a linking group bonded to the carbon atom (C) of the general formula (1). In a case where there is a plurality of *, one of the plurality of * represents a bonding position to the carbon atom (C) of the general formula (1), or a bonding position to a linking group bonded to the carbon atom (C) of the general formula (1). Remaining * other than these represents a hydrogen atom or a substituent. Regarding the substituent, explanation and a preferable range of the substituents represented by Ru to $R^{20}$ can be referred to, but a substituent satisfying a condition of $D-C(R^1)(R^2)$— of the general formula (1) or a substituent satisfying a condition of D of the general formula (1) is also preferable, and among these, a substituent satisfying a condition of D-C(R$^1$)(R$^2$)— of the general formula (1) is more preferable. In a case where * of a substituent represented by any of A-1 to A-77 is directly bonded to the carbon atom (C), the substituent in which Hammett's σ$_p$ value represented by A is positive is constituted of the substituents, and in a case where * of a substituent represented by any of A-1 to A-77 is bonded to a linking group bonded to the carbon atom (C), the substituent in which Hammett's σ$_p$ value represented by A is constituted of the substituent and the linking group. The linking group in a case where a linking group is bonded to the carbon atom (C) is a substituted or non-substituted arylene group or a substituted or non-substituted heteroarylene group.

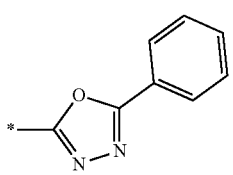

A-1

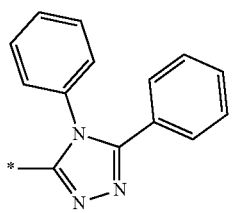

A-2

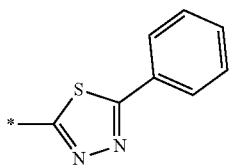

A-3

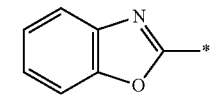

A-4

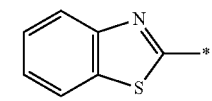

A-5

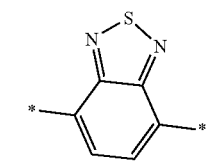

A-6

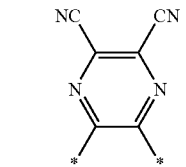

A-7

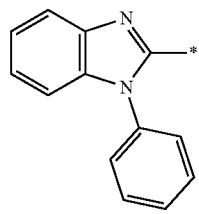

A-8

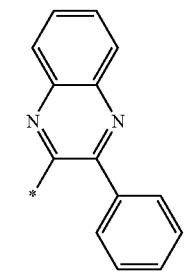

A-9

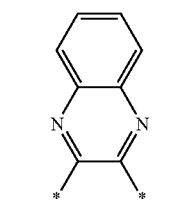

A-10

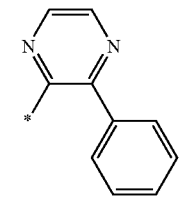

A-11

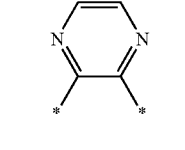

A-12

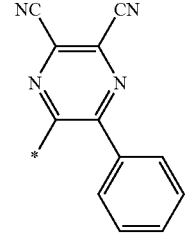

A-13

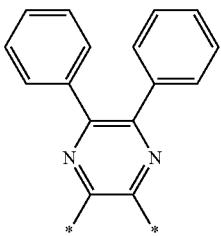

A-14

-continued
A-15
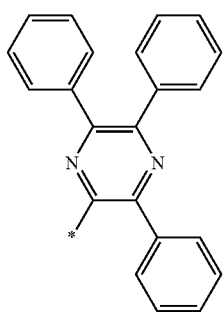
A-16
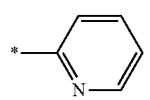
A-17
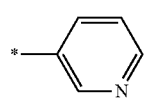
A-18
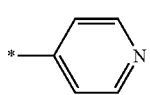
A-19
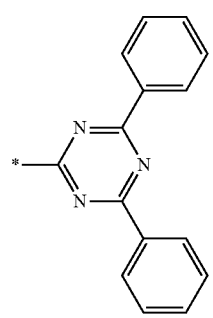
A-20
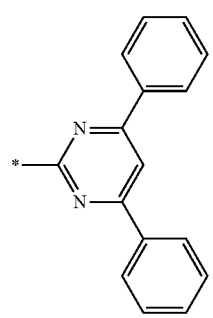
A-21
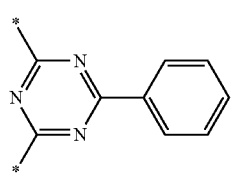
-continued
A-22
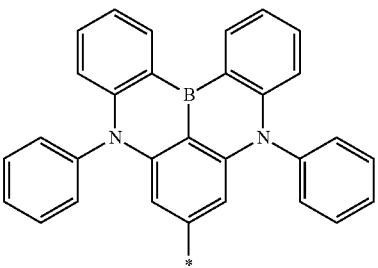
A-23
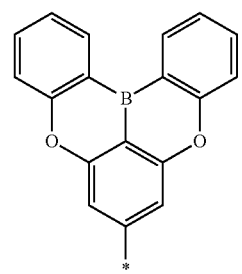
A-24
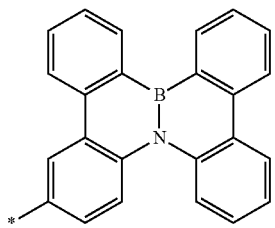
A-25
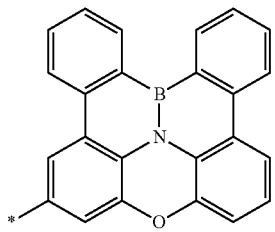
A-26
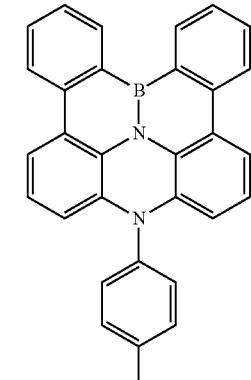
A-27
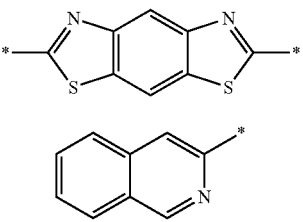
A-28

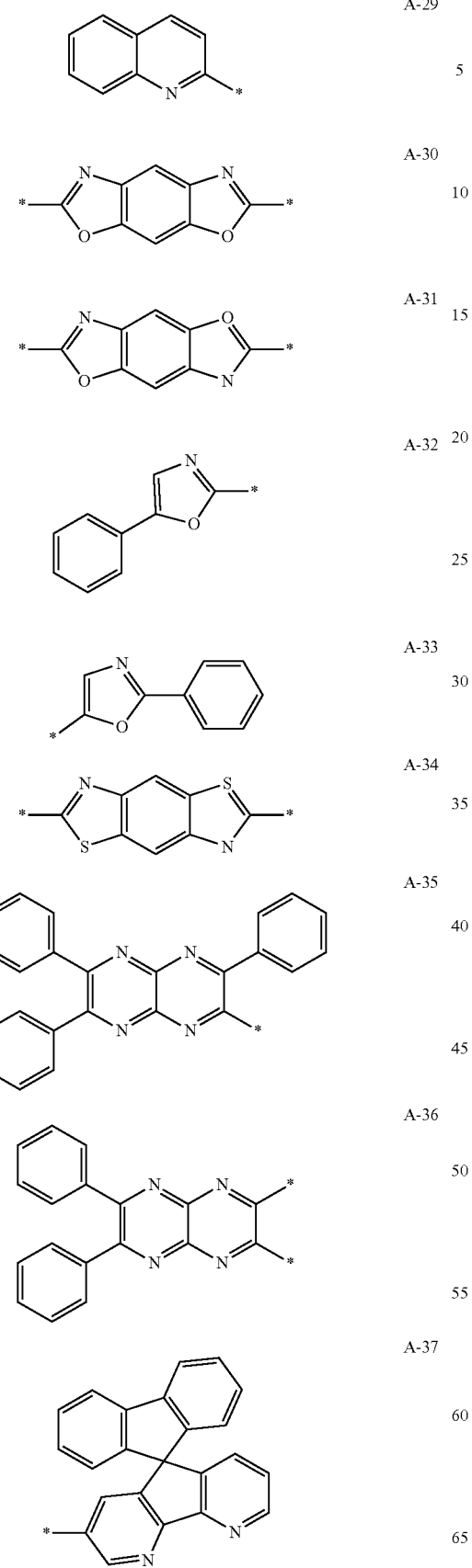
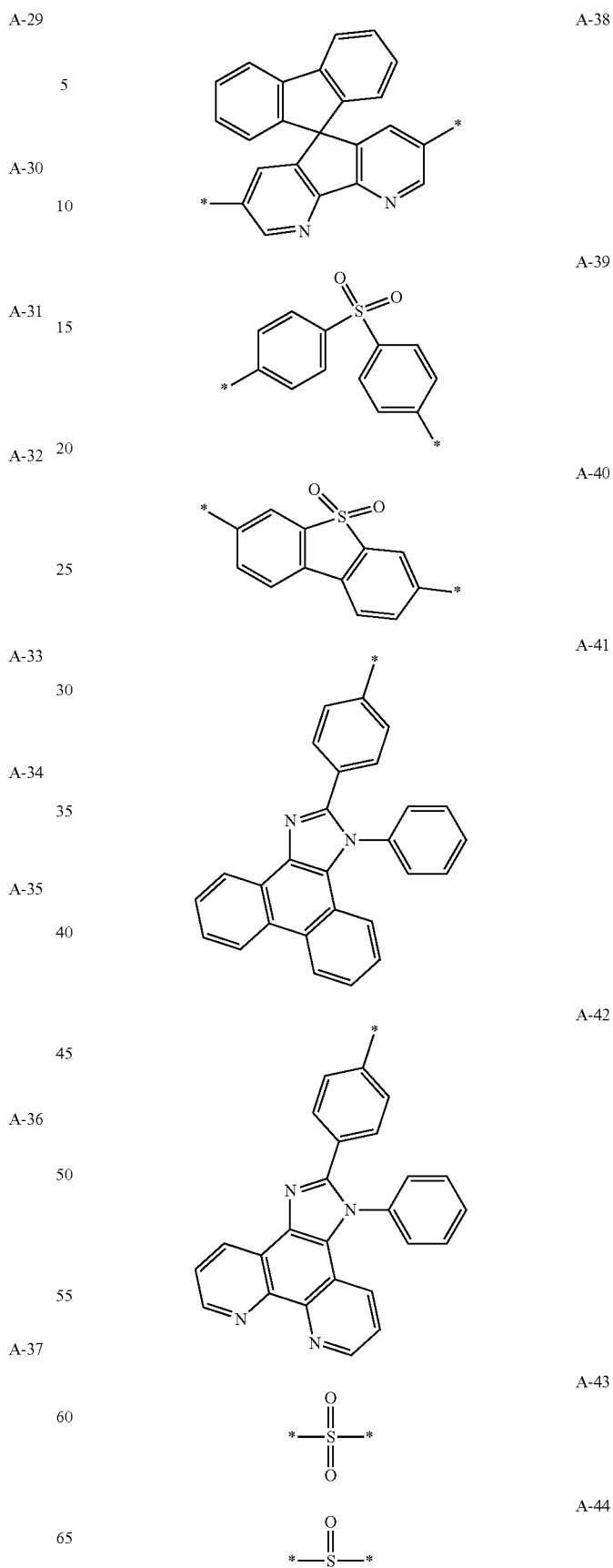

A-45 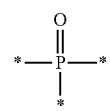
A-46 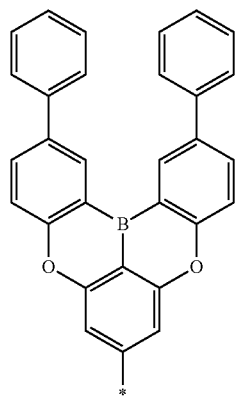
A-47 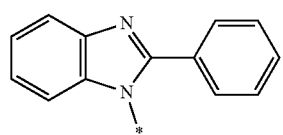
A-48 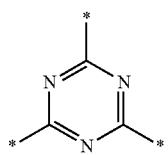
A-49 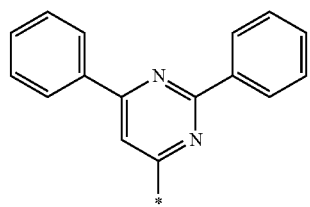
A-50 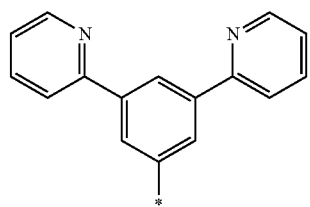
A-51 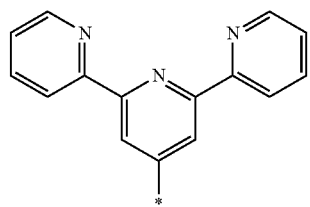
A-52 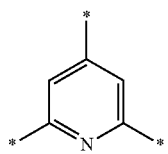
A-53 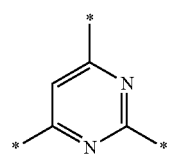
A-54 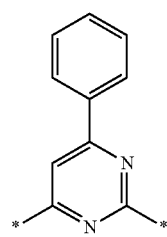
A-55 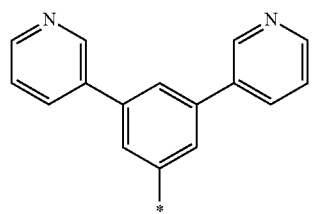
A-56 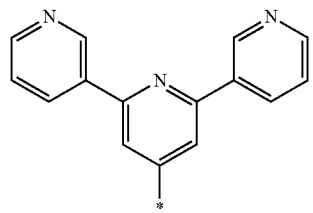
A-57 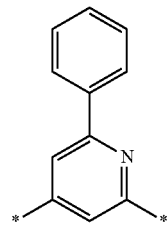
A-58 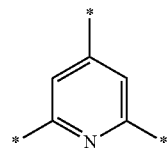
A-59 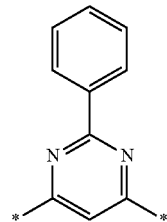

-continued
A-60 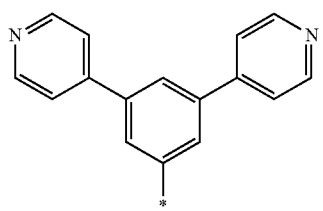
A-61 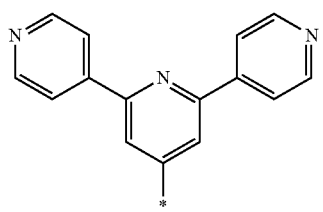
A-62 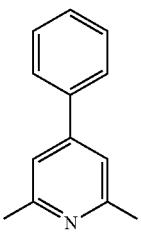
A-63 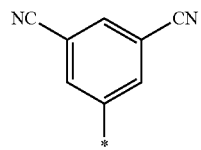
A-64 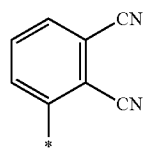
A-65 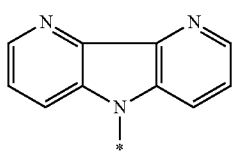
A-66 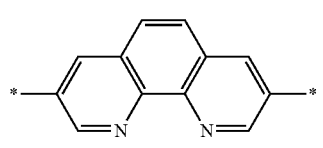
A-67 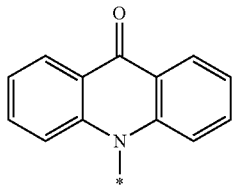
A-68 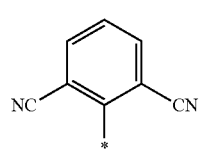
-continued
A-69 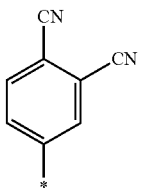
A-70 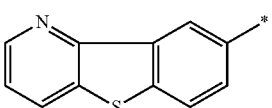
A-71 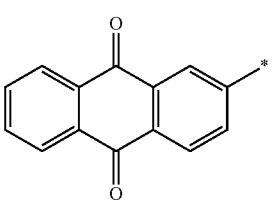
A-72 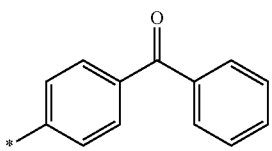
A-73 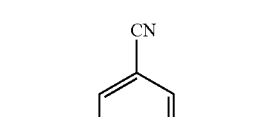
A-74 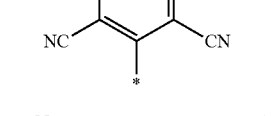
A-75 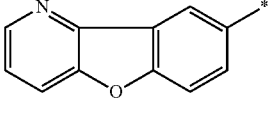
A-76 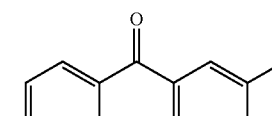
A-77 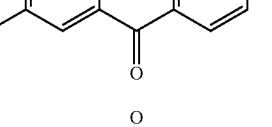
In the following description, specific examples of compounds represented by the general formula (1) will be exemplified. Compounds represented by the general formula (1) capable of being used in the present invention should not be limitedly interpreted by the specific examples.

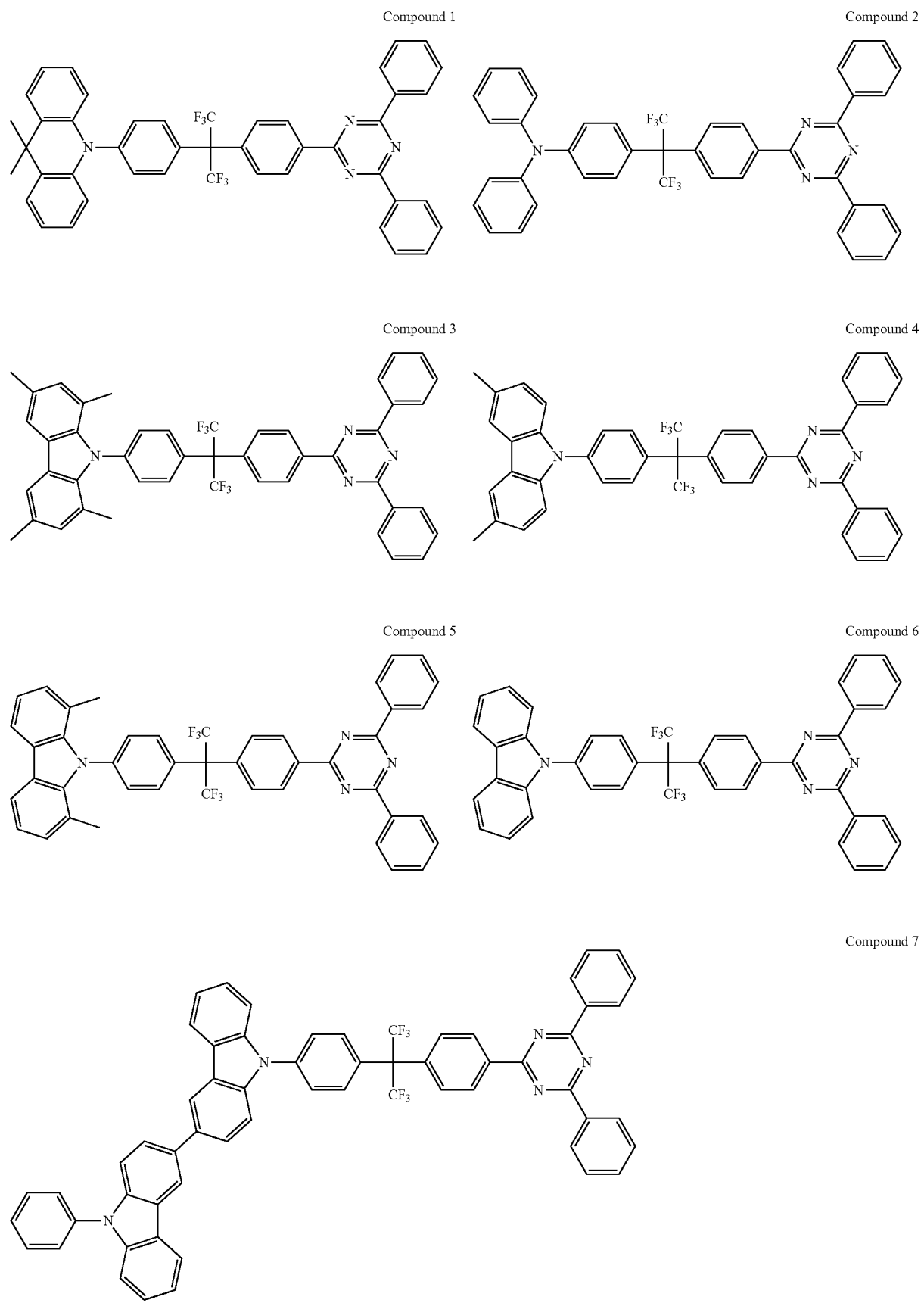

-continued
Compound 8
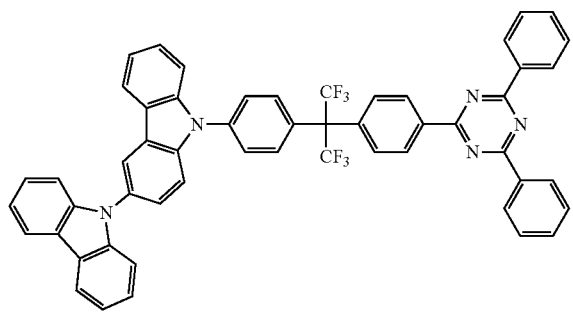
Compound 9
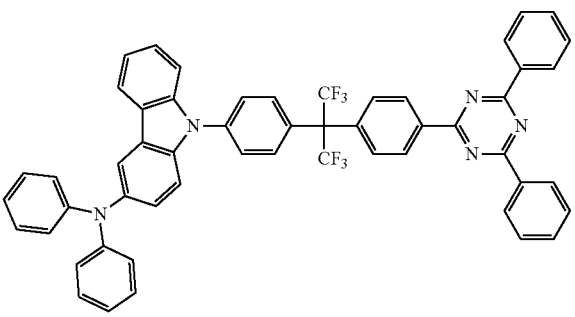
Compound 10
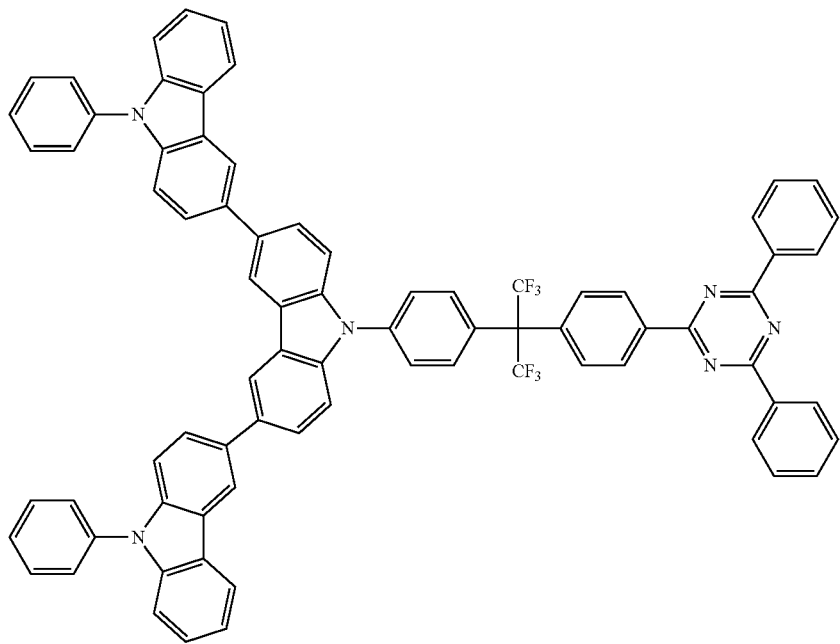
Compound 11
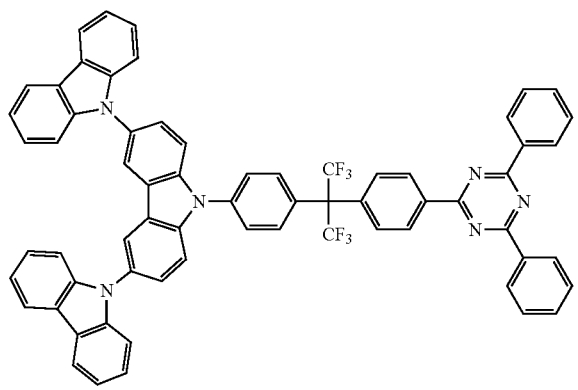
Compound 12
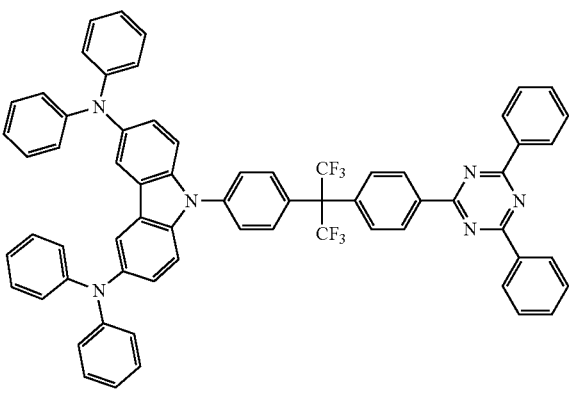

-continued
Compound 13
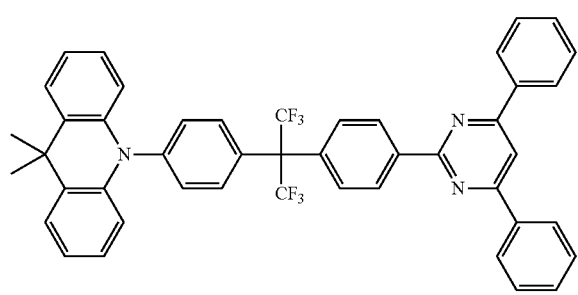
Compound 14
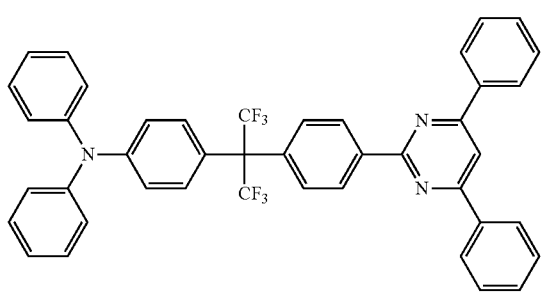
Compound 15
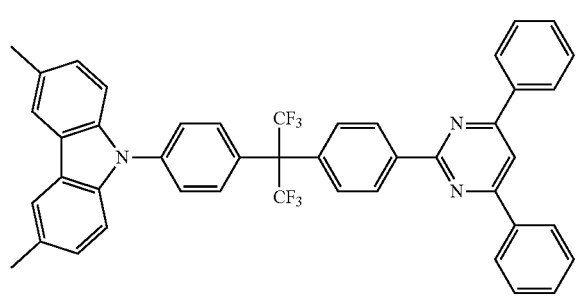
Compound 16
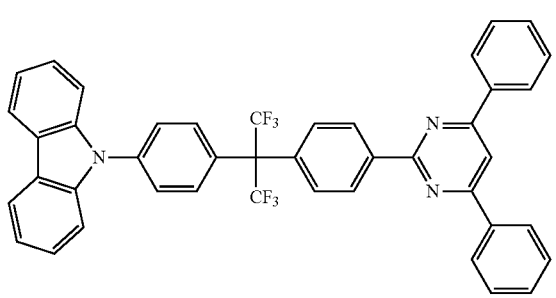
Compound 17
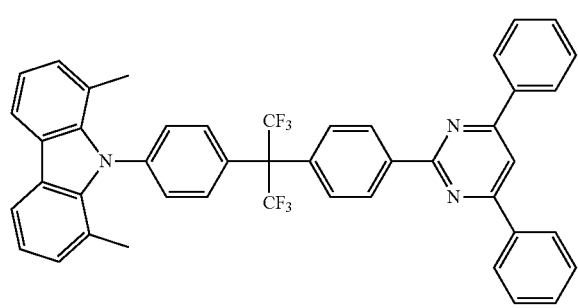
Compound 18
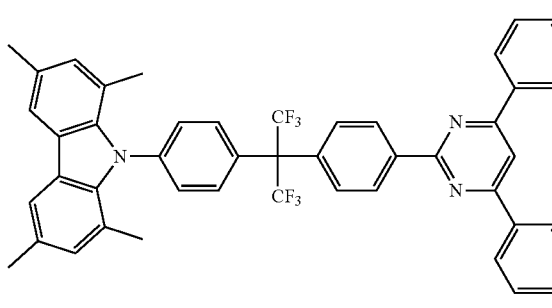
Compound 19
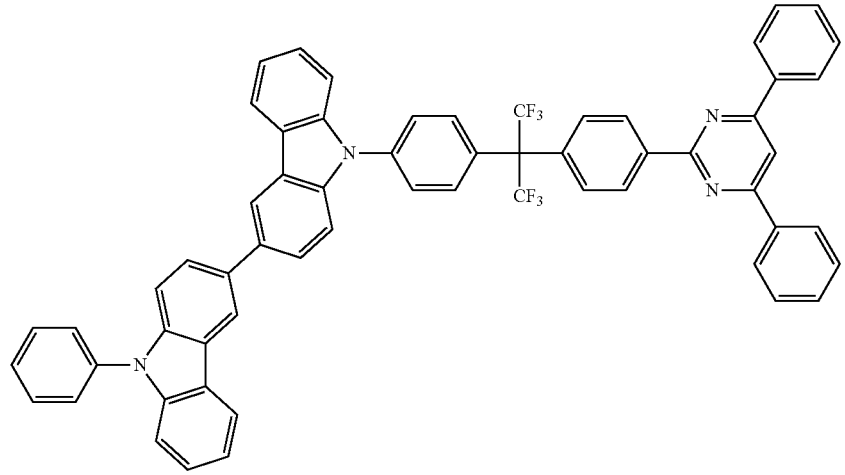

-continued
Compound 20
Compound 21
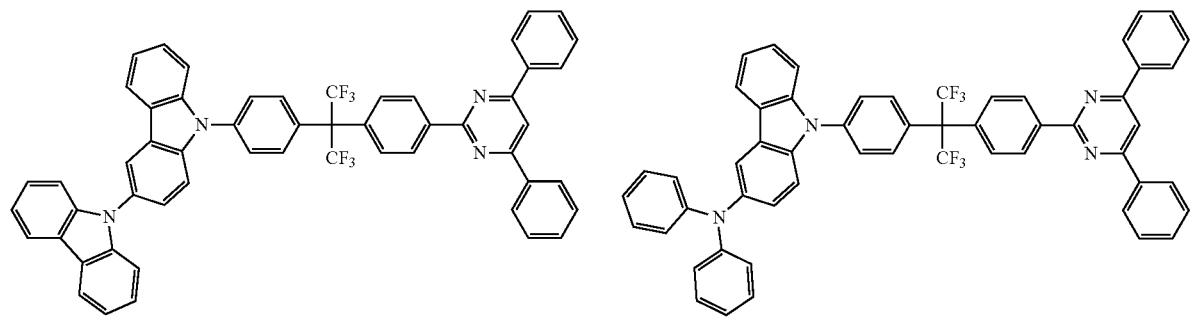
Compound 22
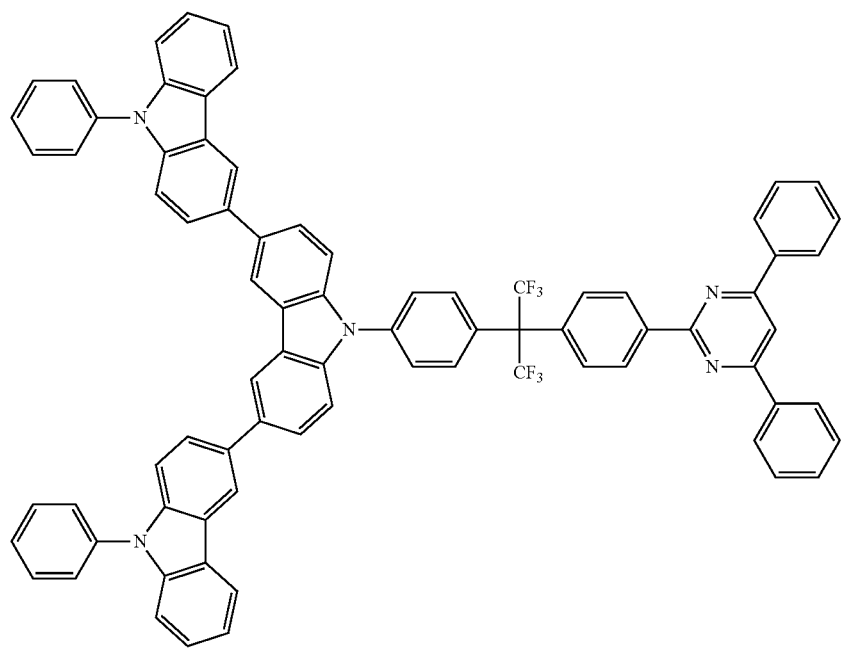
Compound 23
Compound 24
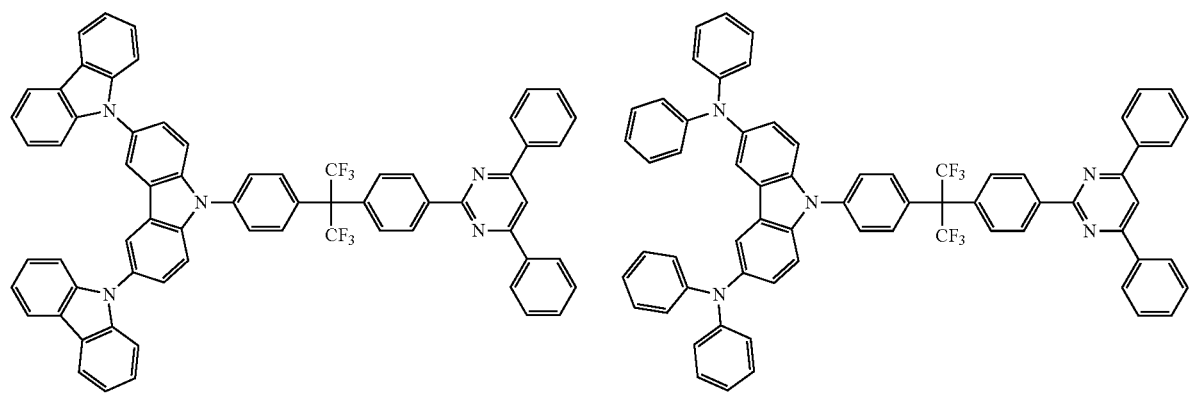

-continued
Compound 25
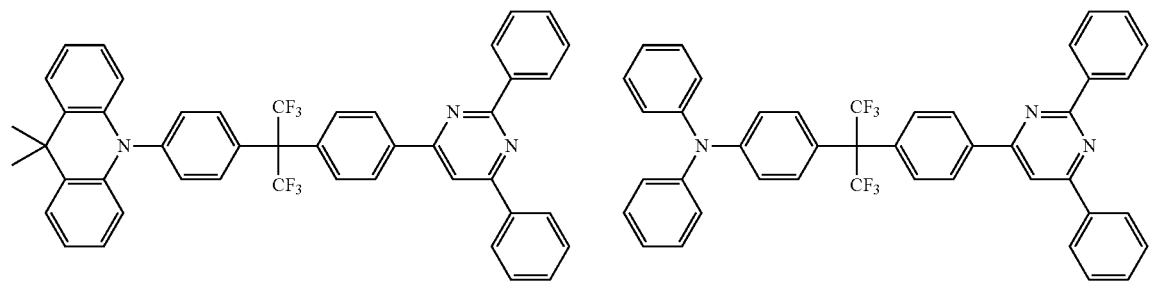
Compound 26
Compound 27
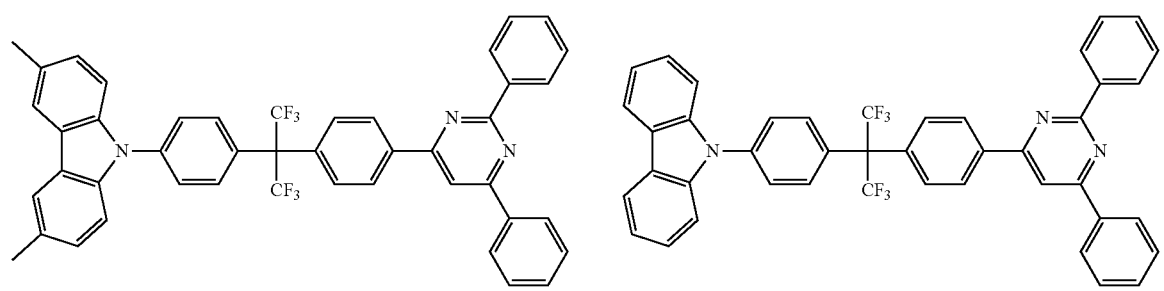
Compound 28
Compound 29
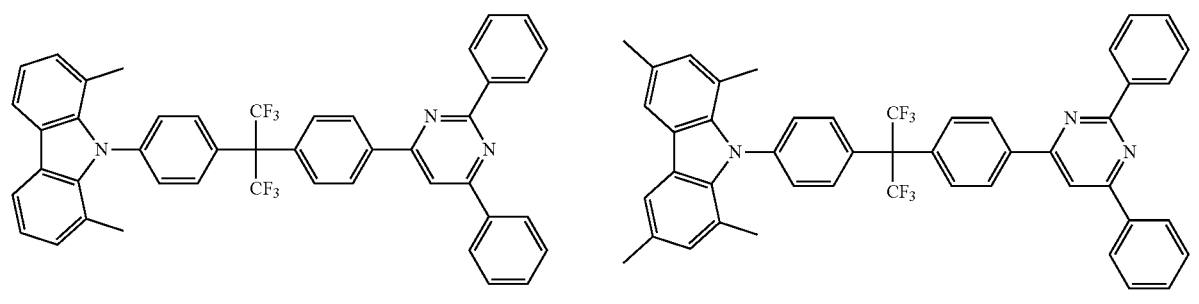
Compound 30
Compound 31
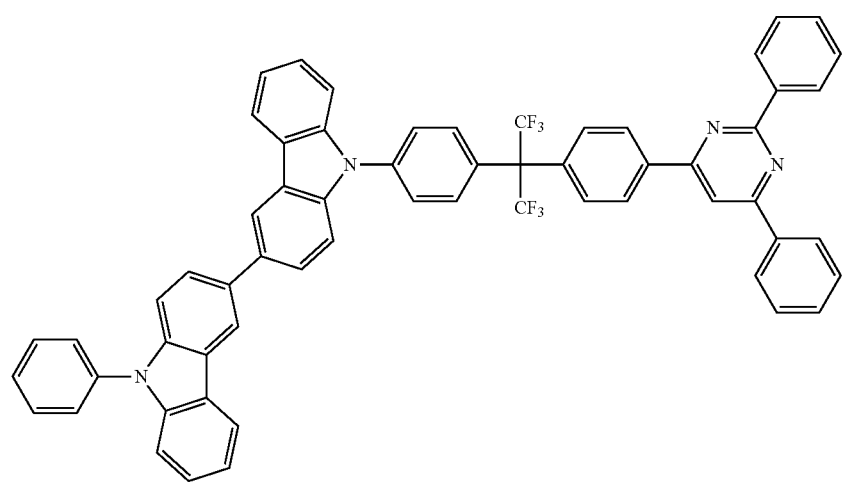

Compound 32    Compound 33
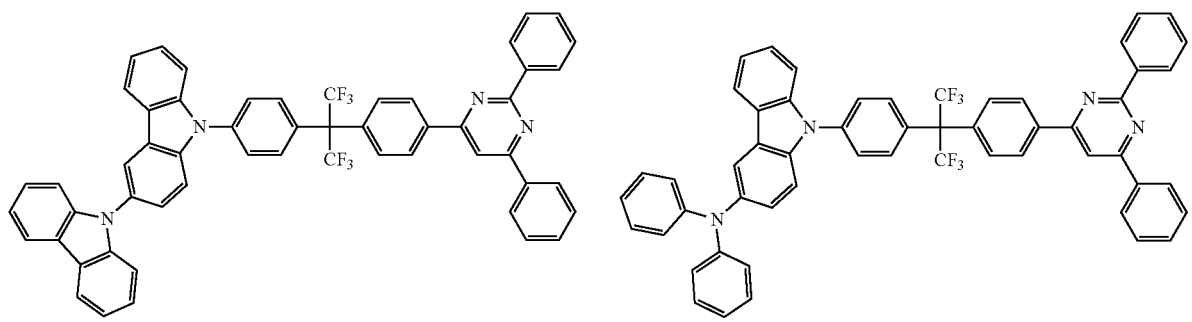
Compound 34
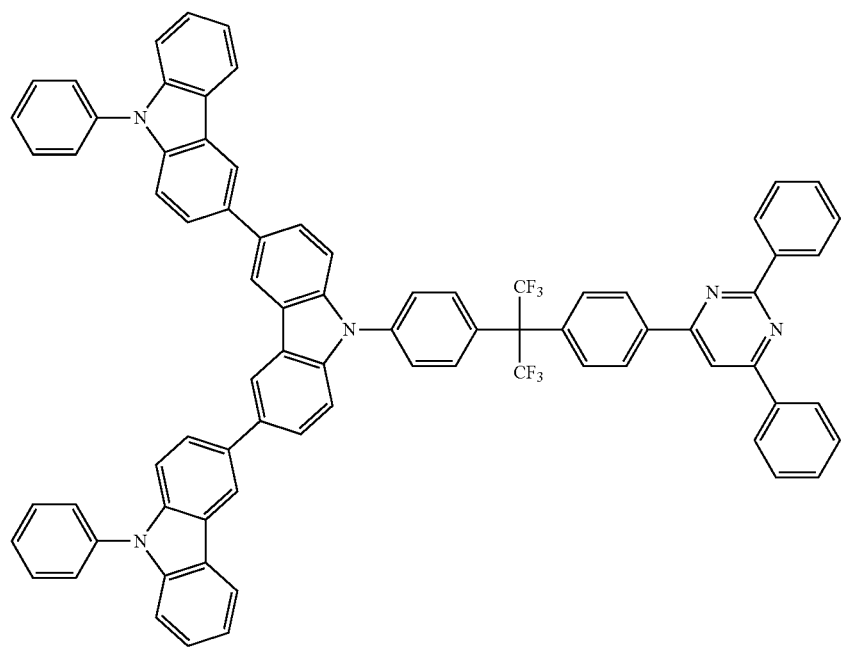
Compound 35    Compound 36
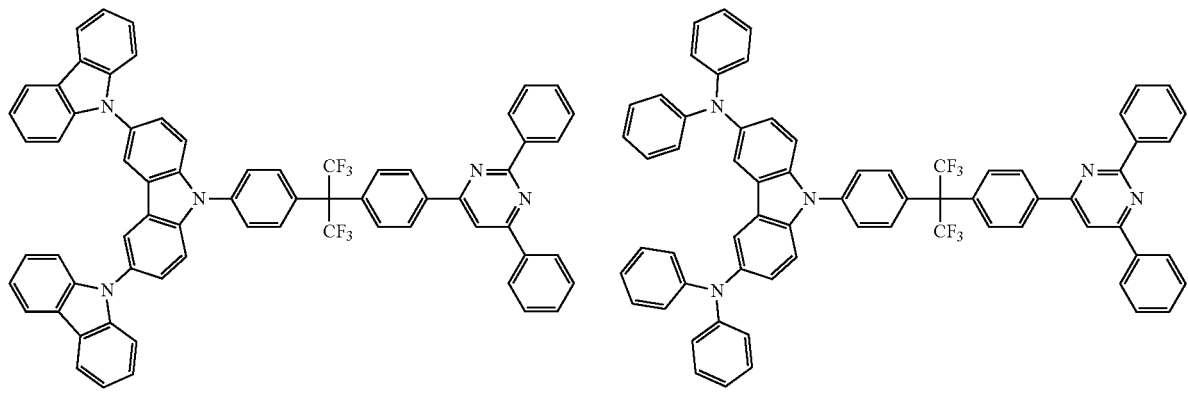

-continued
Compound 37
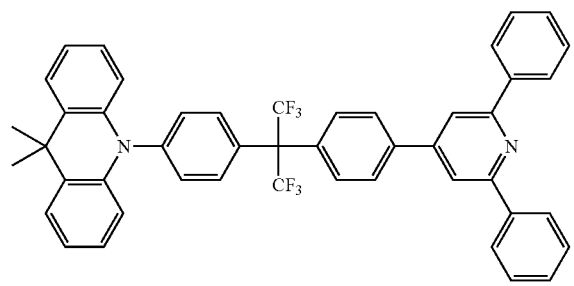
Compound 38
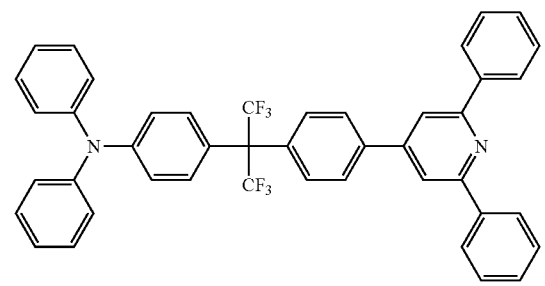
Compound 39
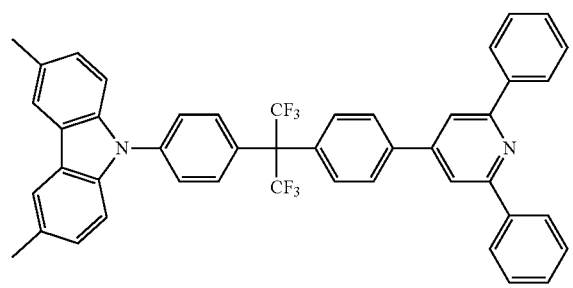
Compound 40
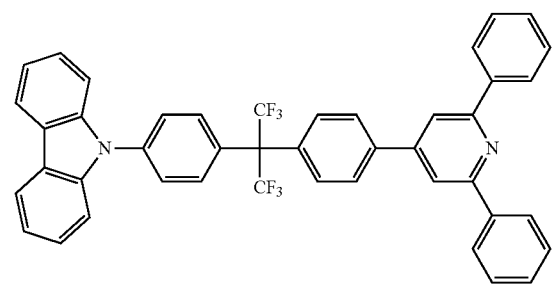
Compound 41
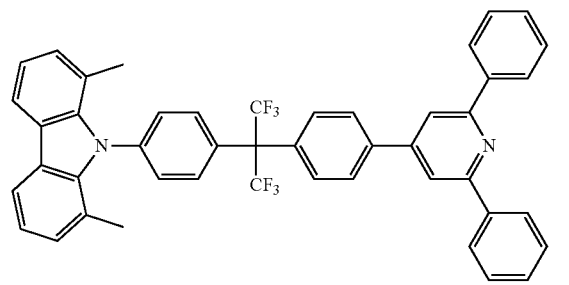
Compound 42
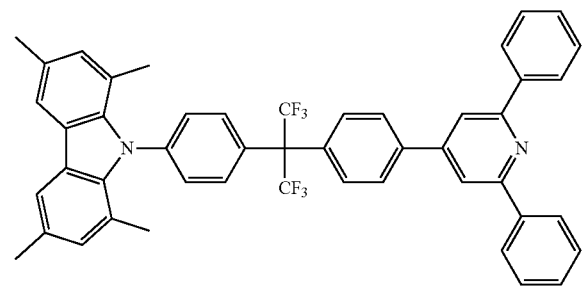
Compound 43
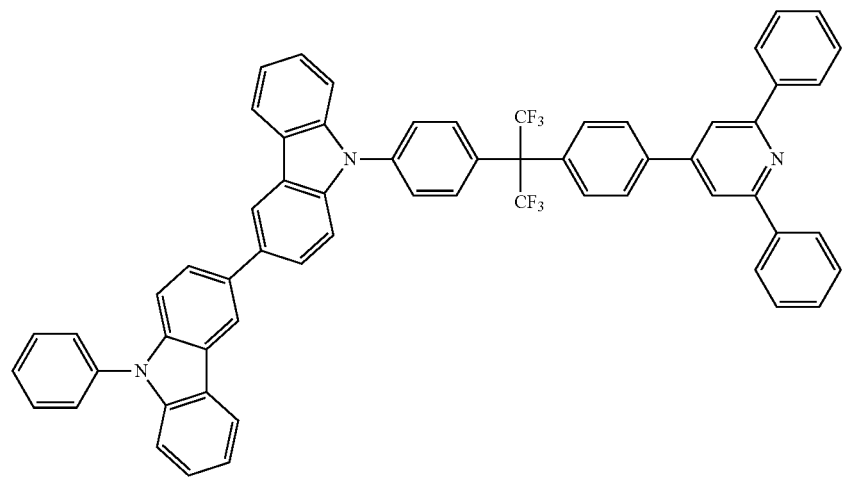

-continued
Compound 44
Compound 45
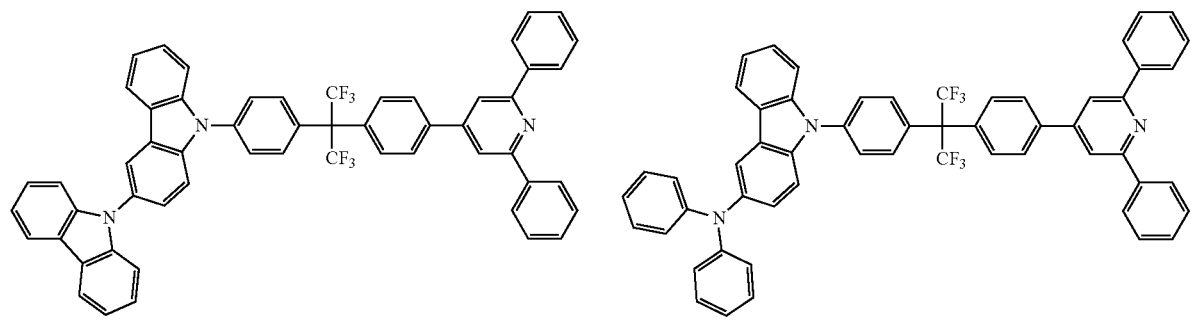
Compound 46
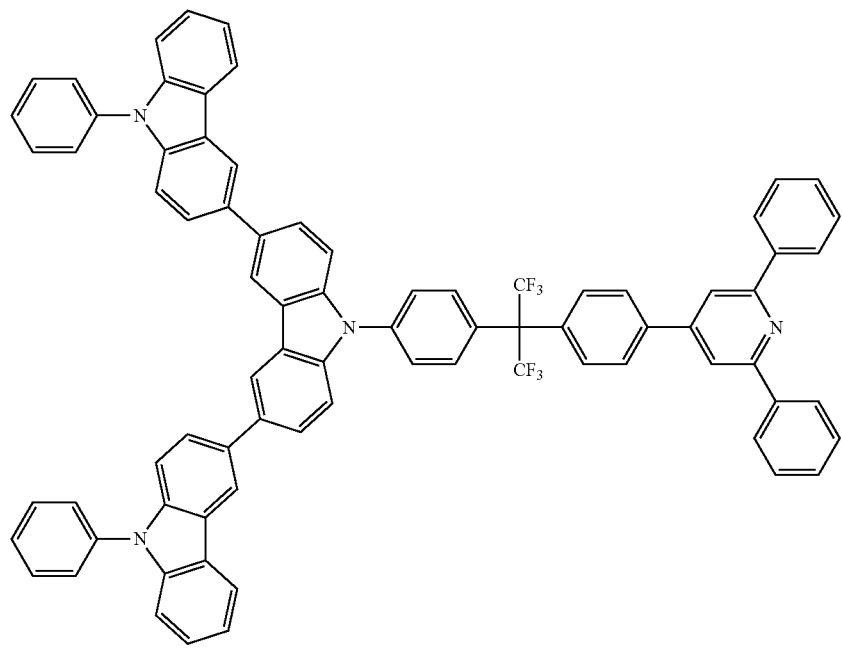
Compound 47
Compound 48
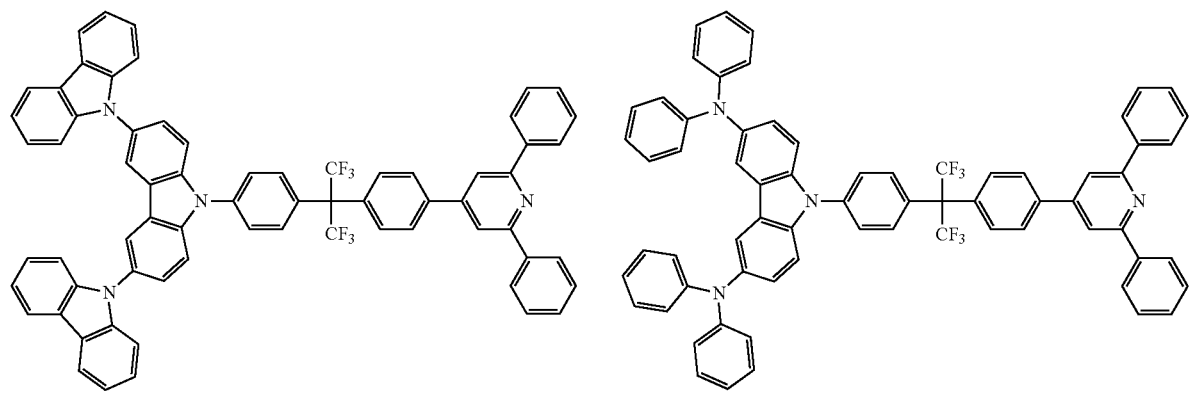

Compound 49
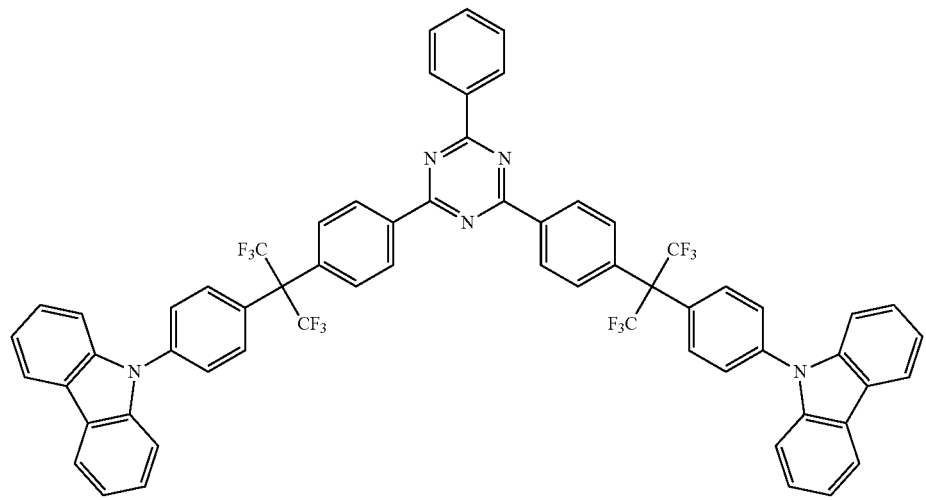
Compound 50
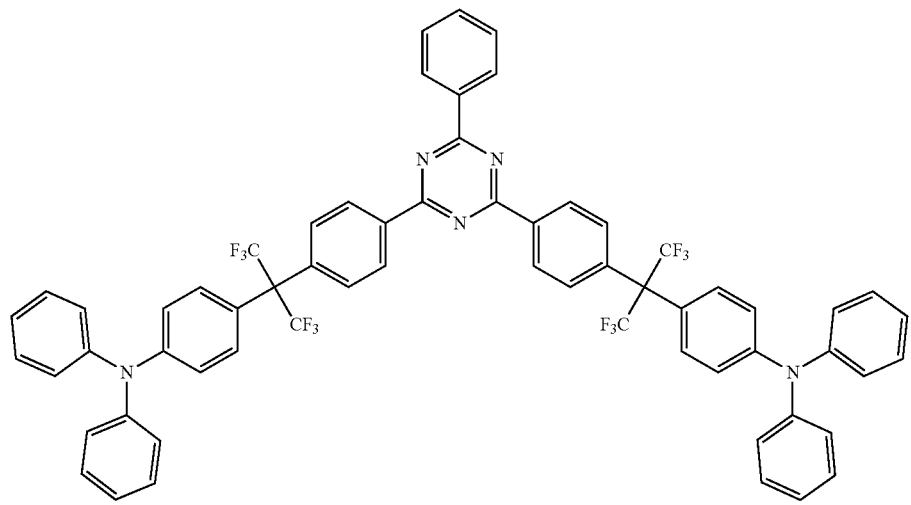
Compound 51
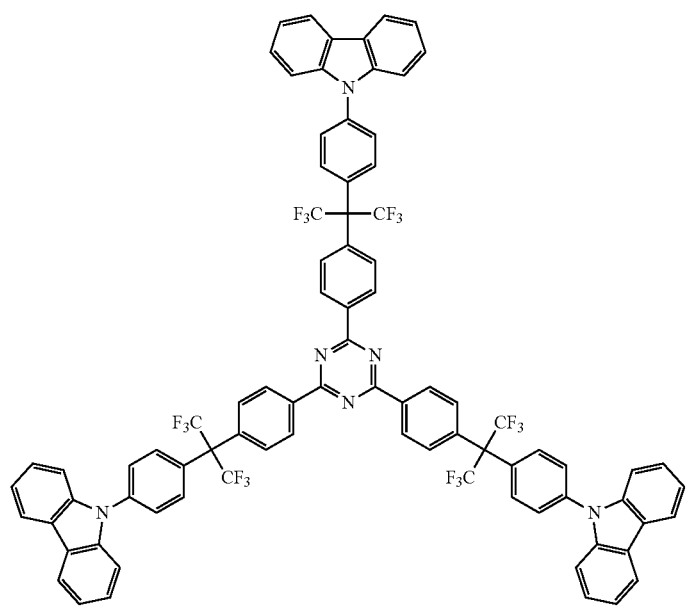

Compound 52
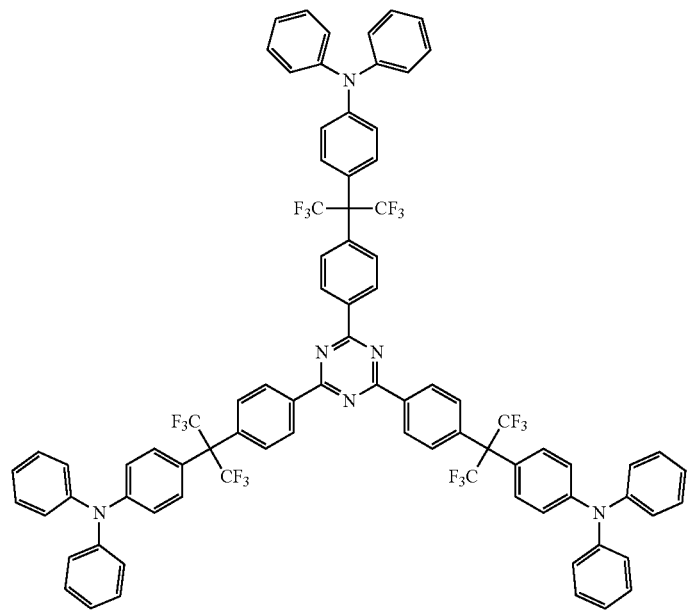
Compound 53
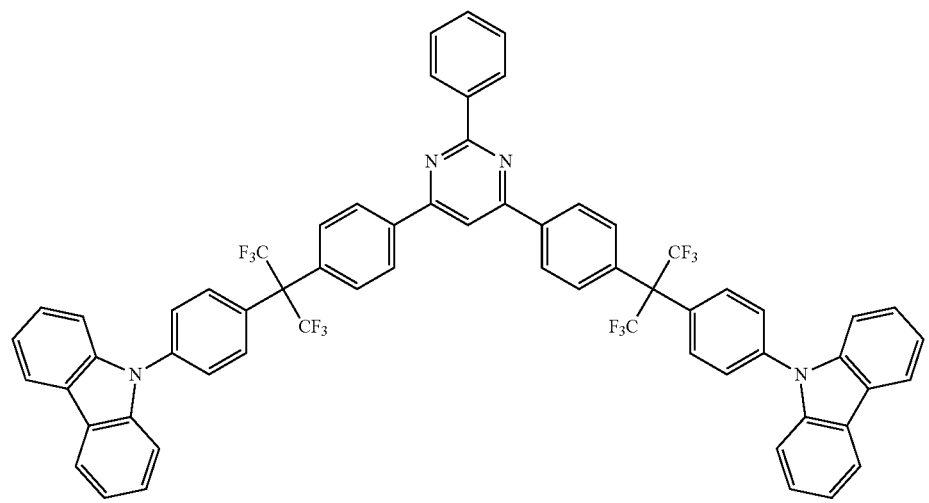
Compound 54
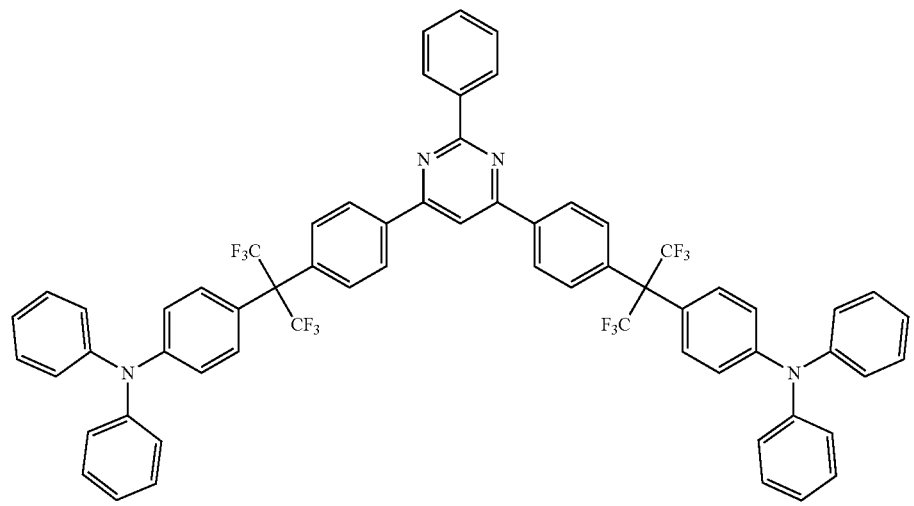

Compound 55
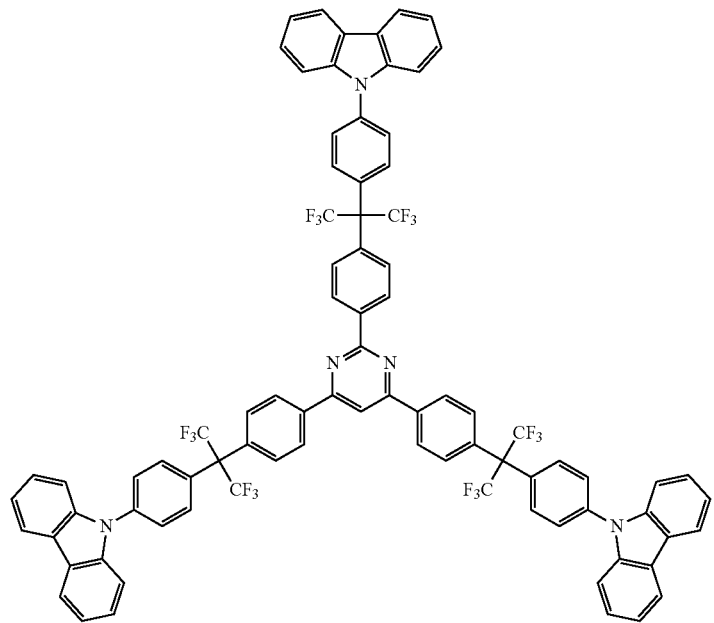
Compound 56
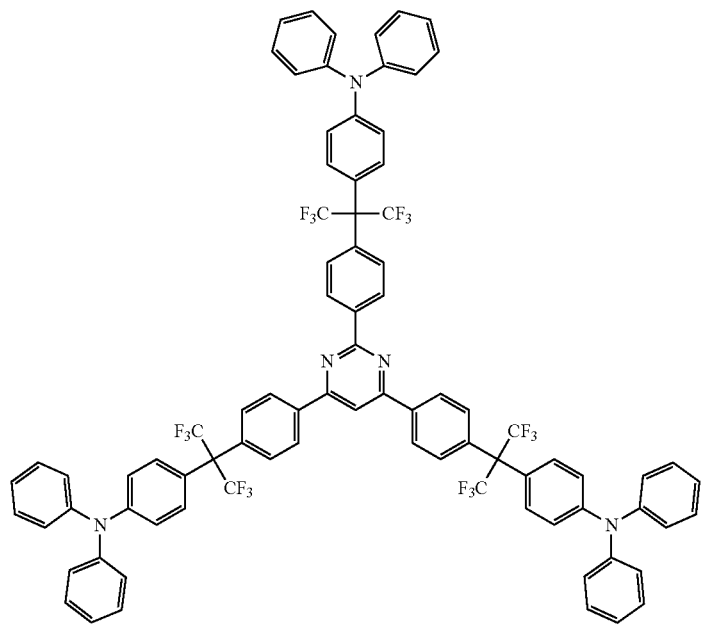

Compound 57
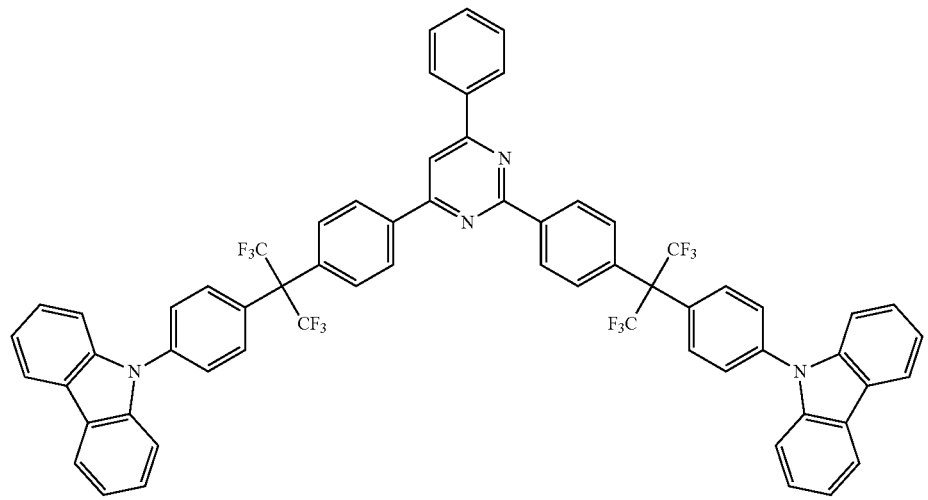
Compound 58
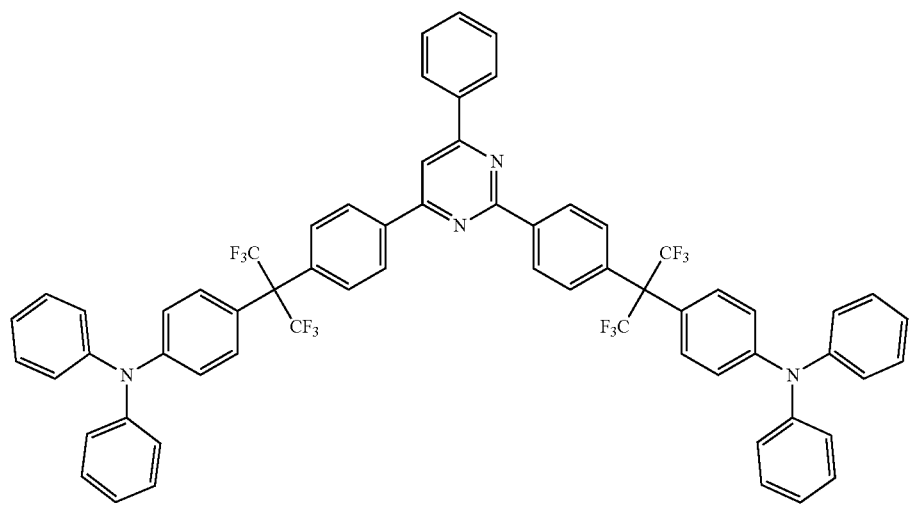
Compound 59
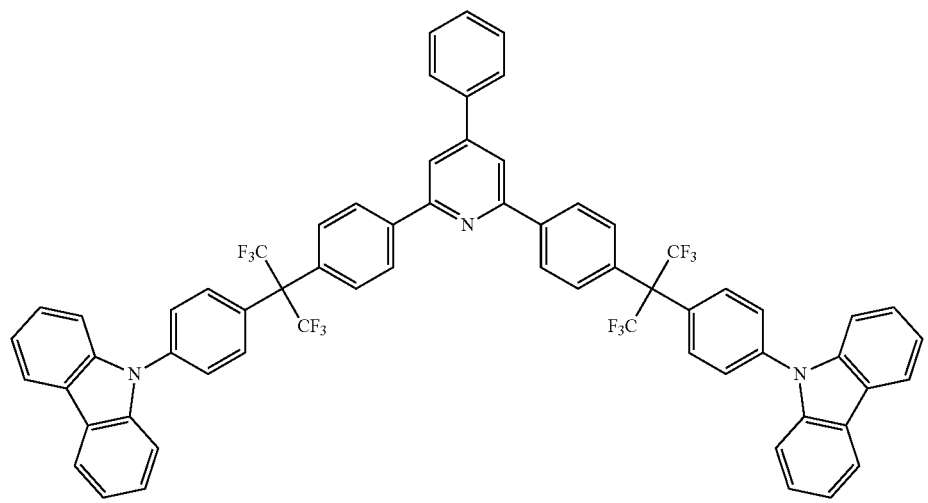

Compound 60

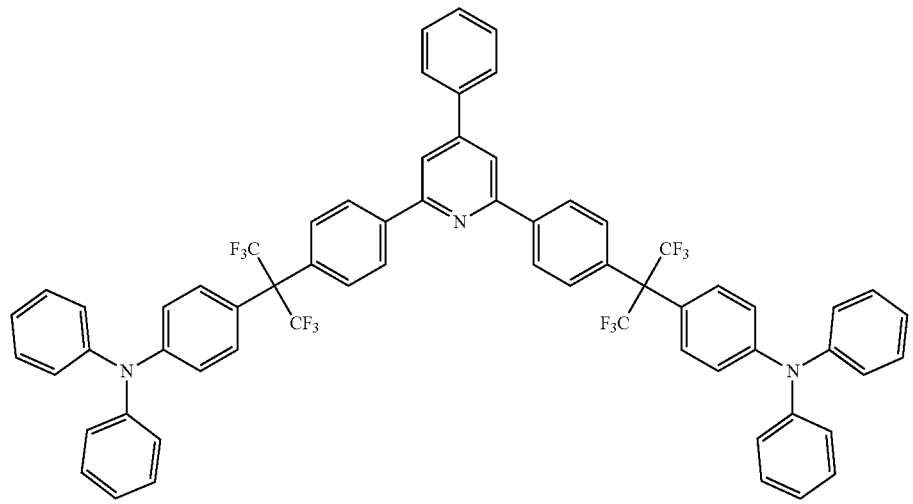

A molecular amount of the compound represented by the general formula (1) is preferably equal to or less than 1,500, more preferably equal to or less than 1,200, further more preferably equal to or less than 1,000, and even further more preferably equal to or less than 900 in a case where it is meant that an organic layer including the compound represented by the general formula (1) is film-formed by a vapor deposition method and used. A lower limit value of the molecular amount is a minimum molecular amount of the compound represented by the general formula (1).

The compound represented by the general formula (1) may be film-formed by a coating method regardless of the molecular amount. In a case of using the coating method, it is possible to form a film even with a compound of a relatively large molecular amount.

By applying the present invention, it is also considered that a compound including a plurality of structures represented by the general formula (1) in molecule is used as a light-emitting material.

For example, it is considered that a polymer obtained by causing a polymerizable group to exist in advance in a structure represented by the general formula (1) and polymerizing the polymerizable group is used as a light-emitting material. Specifically, it is considered that by preparing a monomer including a polymerizable functional group in any of $R^1$, $R^2$, D, and A of the general formula (1), and polymerizing the monomer alone or copolymerizing the monomer with another monomer, a polymer having a repeating unit is obtained and used as a light-emitting material. Or, it is considered that by coupling compounds having a structure represented by the general formula (1), a dimer or a trimer is obtained and used as a light-emitting material.

Examples of the polymer having a repeating unit including the structure represented by the general formula (1) include a polymer including a structure represented by the following general formula (11) or (12).

General formula (11)

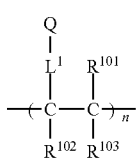

General formula (12)

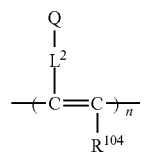

In the general formula (11) or (12), Q represents a group having a structure represented by the general formula (1), and $L^1$ and $L^2$ represent a linking group. The linking group preferably has 0 to 20 carbon atoms, more preferably has 1 to 15 carbon atoms, and further more preferably has 2 to 10 carbon atoms. The linking group preferably has a structure represented by —$X^{11}$-$L^{11}$-. Here, $X^{11}$ represents an oxygen atom or a sulfur atom, and is preferably the oxygen atom. $L^{11}$ represents a linking group, and is preferably a substituted or non-substituted alkyl group, or a substituted or non-substituted arylene group, and is more preferably a substituted or non-substituted alkylene group having 1 to 10 carbon atoms, or a substituted or non-substituted phenylene group.

In the general formula (11) or (12), $R^{101}$, $R^{102}$, $R^{103}$ and $R^{104}$ each independently represent a substituent. $R^{101}$, $R^{102}$, $R^{103}$, and $R^{104}$ each independently is preferably a substituted or non-substituted alkyl group having 1 to 6 carbon atoms, a substituted or non-substituted alkoxy group having 1 to 6 carbon atoms, and a halogen atom, more preferably a non-substituted alkyl group having 1 to 3 carbon atoms, a non-substituted alkoxy group having 1 to 3 carbon atoms, a fluorine atom, and a chlorine atom, and further more preferably a non-substituted alkyl group having 1 to 3 carbon atoms and a non-substituted alkoxy group having 1 to 3 carbon atoms.

A linking group represented by $L^1$ and $L^2$ can be bonded to any of R1, R2, D, and A of a structure of the general formula (1) constituting Q. A crosslinking structure or a mesh structure may be formed by linking two or more linking groups to one Q.

Specific structure examples of a repeating unit include a structure represented by the following formulae (13) to (16).

Formula (13)

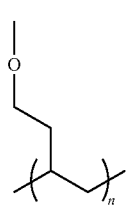

Formula (14)

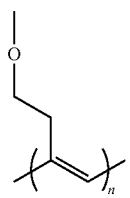

Formula (15)

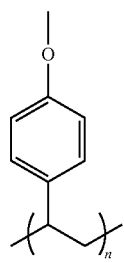

Formula (16)

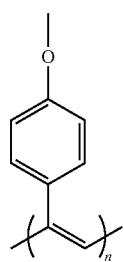

A polymer having a repeating unit including the formulae (13) to (16) can introduce a hydroxy group into any of $R^1$, $R^2$, D, and A of the structure of the general formula (1), can introduce a polymerizable group by reacting the following compound using thereof as a linker, and can perform polymerization by polymerizing the polymeriazble group.

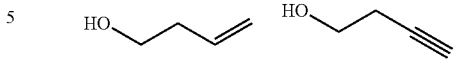

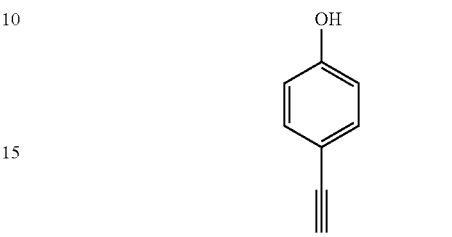

The polymer having a structure represented by the general formula (1) in molecule may be a polymer formed only a repeating unit having a structure represented by the general formula (1), or may be a polymer including a repeating unit having a structure other than that. In addition, the repeating unit having a structure represented by the general formula (1) included in the polymer may be a single kind, or may be two or more kinds. Examples of the repeating unit not having a structure represented by the general formula (1) include a repeating unit derived from a monomer used in general copolymerization. For example, a repeating unit derived from a monomer having an ethylenic unsaturated bond such as ethylene and styrene can be exemplified.

[Method of Synthesis of Compound Represented by General Formula (1)]

A compound represented by the general formula (1) I a new compound.

The compound represented by the general formula. (1) can be synthesized by combining a known reaction. For example, the compound in which D of the general formula (1) is a group represented by the general formula (2), $L^{12}$ is a phenylene group, A is a group represented by the general formula (9), and $L^{19}$ is a phenylene group can be synthesized by synthesizing an intermediate body c' by the following reaction scheme 1, and, as shown in a reaction formula (1), bonding the intermediate body c' and a precursor corresponding to a partial structure (group bonded to $L^{12}$) of the general formula (2) applying coupling reaction.

(Reaction scheme 1)

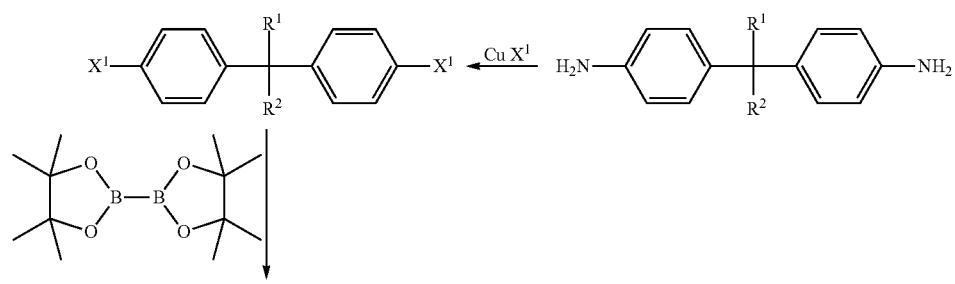

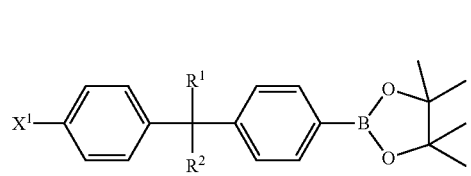 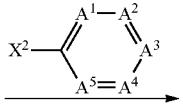 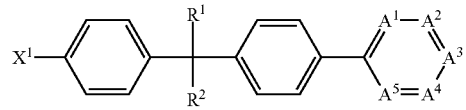

Intermediate body c'

(Reaction formula 1)

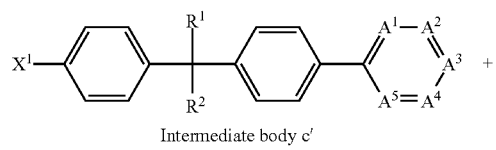 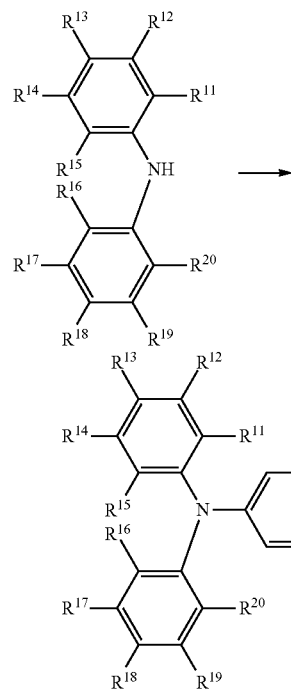

Intermediate body c'

In the reaction scheme 1 and the reaction formula 1, regarding explanation of $R^1$ and $R^2$, explanation corresponding to the general formula (1) can be referred to, regarding explanation of $R^{11}$ to $R^{20}$ explanation corresponding to the general formula (2) can be referred to, and regarding explanation of $A^1$ to $A^5$, explanation corresponding to the general formula (9) can be referred to. $X^1$ and $X^2$ each independently represent a halogen atom, and include a fluorine atom, a chlorine atom, a bromine atom, and an iodine atom, $X^1$ is preferably a bromine atom, and $X^2$ is preferably a chlorine atom.

The reaction is a reaction applying a known coupling reaction, and known reaction conditions can be appropriately selected and used. Regarding the details of the reaction, synthesis examples to be described later can be referred to. In addition, the compound represented by the general formula (1) can be synthesized also by combining known synthesis reaction other than the reaction.

[Organic Light-Emitting Element]

The compound represented by the general formula (1) of the present invention is useful as a light-emitting material of an organic light-emitting element. For this reason, the compound represented by the general formula (1) of the present invention can be effectively used as a light-emitting material in a light-emitting layer of the organic light-emitting element. In addition, the compound represented by the general formula (1) of the present invention may be used as a host or an assist dopant. In addition, the compound represented by the general formula (1) of the present invention may be used in a layer other than the light-emitting layer. For example, the compound represented by the general formula (1) of the present invention may be used in a layer in contact with a cathode side of the light-emitting layer, or may be used in a layer in contact with an anode side of the light-emitting layer. When the compound represented by the general formula (1) of the present invention is used in a layer in contact with a cathode side of the light-emitting layer, the compound represented by the general formula (1) of the present invention can function as a positive hole blocking material, and when the compound represented by the general formula (1) of the present invention is used in a layer in contact with an anode side of the light-emitting layer, the compound represented by the general formula (1) of the present invention can function as an electron blocking material.

In the compound represented by the general formula (1), a delayed fluorescent material (delayed fluorescent body) emitting delayed fluorescence is included. That is, the present invention also provides an invention of a delayed fluorescent body having a structure represented by the general formula (1), an invention using the compound represented by the general formula (1) as a delayed fluorescent body, and an invention of a method of emitting delayed fluorescence by using the compound represented by the general formula (1). An organic light-emitting element using such a compound as a light-emitting material emits delayed fluorescence and exhibits high light emission efficiency. The principle is explained as follows with reference to an organic electroluminescence element.

In the organic electroluminescence element, a carrier is injected into a light-emitting material by both of positive and negative electrodes, a light-emitting material in an excitation state is generated to emit light. In general, in a case of a carrier injection type organic electroluminescence element, among generated excitons, those excitated in an excited singlet state are 25%, and remaining 75% are excited in an excited triplet state. Therefore, using phosphorescence which is emitted from the excited triplet state makes use efficiency of of energy high. However, since the excited triplet state has a long life, saturation of an excitation state or loss of energy due to mutual action with an exciton in an excited triplet state is caused, a quantum yield of phosphorescence generally is not high in many cases. On the other hand, after transition of energy to the excited triplet state due to intersystem crossing, the delayed fluorescent material emits fluorescence reverse-intersystem crossed in an excited singlet state by triplet-triplet extinction or absorption of thermal energy. In the organic electroluminescence element, it is considered that among this, a thermally activated delayed fluorescent material by absorption of thermal energy is particularly useful. In a case where the delayed fluorescent material is used in the organic electroluminescence element, the exciton in an excited singlet state emits fluorescence as usual. On the other hand, the exciton in an excited triplet state is intersystem-crossed to an excited singlet state by absorbing heat generated by a device to emit fluorescence. At this time, since it is light emission from the excited singlet, light is emitted at the same wavelength as that of fluorescence. However, since life of generated light (light emission life) is longer than normal fluorescence by reverse intersystem crossing from the excited triplet state to the excited singlet state, the light is observed as fluorescence delayed than that. This can be defined as delayed fluorescence. If such a thermally activated exciton movement mechanism is used, it is possible to increase a ratio of the compound in the excited singlet state which is normally produced by only 25% to 25% or more through absorption of thermal energy after carrier injection. If a compound generating intense fluorescence and delayed fluorescence even at a low temperature of less than 100° C. is used, delayed fluorescence is emitted by sufficiently generating intersystem crossing from the excited triplet state to the excited singlet state with heat of the device, and thus it is possible to dramatically improve light emission efficiency.

By using the compound represented by the general formula (1) of the present invention as a light-emitting material of the light-emitting layer, it is possible to provide an excellent organic light-emitting element such as an organic photoluminescence element (organic PL element) and an organic electroluminescence element (organic EL element). The organic photoluminescence element has a structure in which at least a light-emitting layer is formed on a substrate. In addition, the organic electroluminescence element has a structure in which at least an anode, and a cathode, and an organic layer between the anode and the cathode are formed. The organic layer includes at least a light-emitting layer, and may be a layer formed only of a light-emitting layer, or may have one or more organic layers in addition to the light-emitting layer. Examples of such an organic layer include a positive hole transport layer, a positive hole injection layer, an electron blocking layer, a positive hole blocking layer, an electron injection layer, an electron transport layer, an exciton blocking layer, and the like. The positive hole transport layer may be a positive hole injection transport layer having a positive hole injection function, or may be an electron injection transport layer having an electron injection function. A specific structure example of the organic electroluminescence element is shown in FIG. 1. In FIG. 1, 1 represents a substrate, 2 represents an anode, 3 represents a positive hole injection layer, 4 represents a positive hole transport layer, 5 represents a light-emitting layer, 6 represents an electron transport layer, and, 7 represents a cathode.

In the following description, each member and each layer of the organic electroluminescence element will be described. Explanation of a substrate and a light-emitting layer also corresponds to that of the substrate and the light-emitting layer of the organic photoluminescence element.

(Substrate)

The organic electroluminescence element of the present invention is preferably supported by a substrate. The substrate is not particularly limited as long as the substrate is practically used in the organic electroluminescence element in the related art, and a substrate formed of glass, transparent plastic, quartz, silicon, and the like can be used.

(Anode)

As an anode in the organic electroluminescence element, an anode using metal having a large work function (4 eV or more), an alloy, an electroconductive compound, and a mixture thereof as an electrode material is preferably used. Specific examples of such an electrode material include metal such as Au and a conductive transparent material such as CuI, indium tin oxide (ITO), $SnO_2$, and ZnO. In addition, a material such as IDIXO ($In_2O_3$—ZnO) with which a transparent conductive film can be prepared in an amorphous form may be used. The anode may be prepared by forming a thin film with the electrode material by a method such as deposition and sputtering and forming a desired form of pattern by a photolithography method, or in a case where pattern accuracy is not required much (approximately equal to or more than 100 μm), a pattern may be formed via a desired form of mask at a time of deposition or sputtering of the electrode material. Or, in a case where an applicable material such as an organic conductive compound is used, it is possible to use a wet type film deposition method such as a print method and a coating method. In a case where light emission is taken out by the anode, it is desired to increase transmittance by 10%, and sheet resistance as an anode is preferably equal to or less than several hundreds of Ω/□. In addition, a film thickness may be a material, but generally is selected from a range of 10 to 1,000 nm and preferably 10 to 200 nm.

(Cathode)

On the other hand, as a cathode, a cathode using metal having a small work function (4 eV or less) (referred to as electron injection metal), an alloy, an electroconductive compound, and a mixture thereof as an electrode material is used. Specific examples of such an electrode material include sodium, a sodium-potassium alloy, magnesium, lithium, a magnesium/copper mixture, a magnesium/indium mixture, an aluminum/aluminum oxide ($Al_2O_2$) mixture, indium, a lithium/aluminum mixture, rare earth metal, and the like. Among these, from a viewpoint of durability against electron injection properties and oxidation, a mixture of electron injection metal and second metal having a larger and more stable value of work function than that, for example, a magnesium/copper mixture, a magnesium/aluminum mixture, a magnesium/indium mixture, an aluminum/aluminum oxide ($Al_2O_3$) mixture, a lithium/aluminum mixture, aluminum, and the like are preferable. The cathode can be prepared by forming a thin film with an electrode material by a method such as deposition and sputtering. In addition, sheet resistance as a cathode is preferably several hundreds of Ω/□, and the film thickness is selected from a range of 10 nm to 5 μm, and preferably 50 to 200 nm. In order to transmit the emitted light, when either one of the anode and the cathode of the organic electroluminescence element is transparent or translucent, light emission luminance is improved and thus desirable.

In addition, by using the conductive transparent material exemplified in explanation of the anode in the cathode, it is possible to produce a transparent or translucent cathode, and by applying this, it is possible to produce an element in which both of the anode and the cathode have transmittance.

(Light-Emitting Layer)

The light-emitting layer is a layer that emits light after the exciton is generated by rebonding a positive hole and an electron injected from each of the anode and the cathode. The light-emitting material may be used alone in the light-emitting layer, but preferably includes a light-emitting material and a host material. As the light-emitting material, it is possible to use one or two or more selected from the compound group of the present invention represented by the general formula (1). In order for the organic electroluminescence element and the organic photoluminescence element of the present invention to realize high light emission efficiency, it is important to confine a singlet exciton and a triplet exciton generated from the light-emitting material in the light-emitting material. Therefore, it is preferable to use a host material in a light-emitting layer, in addition to the light-emitting material. As a host material, it is possible to use an organic compound in which at least any one of excited singlet energy and excited triplet energy has a higher value than the light-emitting material of the present invention. As a result, it is possible to confine a singlet exciton and a triplet exciton generated in the light-emitting material of the present invention in molecule of the light-emitting material of the present invention, and it is possible to sufficiently draw the light emission efficiency. At this time, even if it is possible to sufficiently confine the singlet exciton and the triplet exciton, there is a case where high light emission efficiency can be obtained, and thus a host material realizing high light emission efficiency can be used in the present invention without particular limitation. In the organic light-emitting element and the organic electroluminescence element of the present invention, light emission is generated from the light-emitting material of the present invention included in the light-emitting layer. The light emission includes both of fluorescent light emission and delayed fluorescent light emission. Here, there is no problem whether there is a part or partial light emission from a host material in light emission.

In a case where the compound represented by the general formula (1) is used as a light-emitting material, a content of the compound represented by the general formula (1) in the light-emitting layer is preferably less than 50% by weight. In addition, an upper limit value of the content of the compound represented by the general formula (1) is preferably less than 30% by weight, and an upper limit value of the content can be, for example, less than 20% by weight, less than 10% by weight, less than 5% by weight, less than 3% by weight, less than 1% by weight, and less than 0.5% by weight. A lower limit value is preferably equal to or more than 0.001% by weight, and can be, for example, more than 0.01% by weight, more than 0.1% by weight, more than 0.5% by weight, and more than 1% by weight.

The host material in the light-emitting layer is preferably an organic compound that has a positive hole transport function and an electron transport function, can prevent a long wavelength of light emission, and has a high glass transition temperature.

In addition, as another aspect of the light-emitting layer, it is possible to exemplify an aspect including a light-emitting material and a host material, and including the compound represented by the general formula (1) as an assist dopant. As the assist dopant, it is possible to use one or two or more selected from the compound group represented by the general formula (1). The compound represented by the general formula (1) used as an assist dopant is preferably a compound in which a lowest excited singlet energy level is higher than the light-emitting material and a lowest excited singlet energy level is lower than the host material. With this, excited singlet energy generated from the host material easily moves to an assist dopant and a light-emitting material, and excited singlet energy generated from the host material and excited singlet energy moved from the host material to the assist dopant easily move to a light-emitting material. As a result, a light-emitting material in an excited singlet state is efficiently generated and high light emission efficiency can be obtained. In addition, the compound represented by the general formula (1) used as an assist dopant has a lowest excited triplet energy level lower than the host material, and a difference $\Delta E_{st}$ between the lowest excited singlet energy level and the lowest excited triplet energy level is preferably equal to or less than 0.3 eV, more preferably equal to or less than 0.2 eV, and further more preferably equal to or less than 0.1 eV. With this, the excited triplet energy generated from the host material easily moves to the assist dopant, and the assist dopant transits to an excited triplet state. In addition, reverse intersystem crossing is easily generated by the assist dopant that came into the excited triplet state, and transits to an excited singlet state. As a result of the excited singlet energy of the assist dopant being moved to a light-emitting material, a light-emitting material in an excited singlet state is efficiently generated, and extremely high light emission efficiency can be obtained. In other words, it is possible to effectively use the excited triplet energy generated from the host material or the assist dopant in light emission of the light-emitting material.

As the light-emitting material used in this aspect, a known light-emitting material can be employed, and a fluorescent light-emitting material is preferably used and a delayed fluorescent body may be used. Regarding explanation of the host material, explanation of the host material of the aspect of using the compound represented by the general formula (1) in the light-emitting material can be referred to.

In a case where the compound represented by the general formula (1) is used as an assist dopant, a content of the compound represented by the general formula (1) is used as an assist dopant, a content of the compound represented by the general formula (1) in the light-emitting layer is smaller than the content of the host material and larger than the content of the light-emitting material. That is, the content of the compound represented by the general formula (1) in the light-emitting layer preferably satisfies relationship of "the content of the light-emitting material<the content of the assist dopant<the content of the host material". Specifically, the content of the compound represented by the general formula (1) in the light-emitting layer in this aspect is preferably less than 50% by weight. In addition, an upper limit value of the content of the compound represented by the general formula (1) is preferably less than 40% by weight, and the upper limit value of the content can be less than 30% by weight, less than 20% by weight, and less than 10% by weight, for example. A lower limit value is preferably equal to or more than 0.1% by weight, and can be more than 1% by weight, and more than 3% by weight, for example.

In addition, another aspect of the light-emitting layer includes an aspect in which the light-emitting layer includes the compound represented by the general formula (1) as a host material and also includes a light-emitting material, in addition to the compound represented by the general formula (1). As the light-emitting material used at this time, a known light-emitting material can be employed, and a fluorescent light-emitting material is preferably used, and a delayed fluorescent body may be used. In a case where the compound represented by the general formula (1) is used as a host material, a content of the compound represented by the general formula (1) in the light-emitting layer is preferably equal to or more than 50% by weight, and can be equal to or more than 75% by weight, for example.

(Injection Layer)

The injection layer is a layer provided between an electrode and an organic layer in order to lower a drive voltage or improve light emission brightness, and there is a positive injection layer and an electron injection layer, and may exist between an anode and a light-emitting layer or a positive hole transport layer and between a cathode and a light-emitting layer or an electron transport layer. The injection layer can be provided depending on the necessity.

(Blocking Layer)

The blocking layer is a layer capable of blocking diffusion of an electric charge (electron or positive hole) and/or an exciton present in the light-emitting layer to the outside of the light-emitting layer. The electron blocking layer can be disposed between the light-emitting layer and the positive hole transport layer, and blocks the electron from passing through the light-emitting layer toward the positive hole transport layer. At the same time, the positive hole blocking layer can be disposed between the light-emitting layer and the electron transport layer, and blocks the positive hole from passing through the light-emitting layer toward the electron transport layer. In addition, the blocking layer can be used to block diffusion of the exciton to the outside of the light-emitting layer. That is, each of the electron blocking layer and the positive hole blocking layer can also have a function as an exciton blocking layer. The election blocking layer or the exciton blocking layer in the present specification are used as meaning including a layer having a function of the electron blocking layer and the and a function of the exciton blocking layer in one layer.

(Positive Hole Blocking Layer)

The positive hole blocking layer has a function of an electron transport layer in wide meaning. The positive hole blocking layer has a role of blocking the positive long from reaching the electron transport layer while transporting the electron, and with this, it is possible to improve rebonding probability of the electron and the positive hole in the light-emitting layer. As a material of the positive hole blocking layer, a material of the electron transport layer to be described layer can be used depending, on the necessity. In addition, it is possible to use the compound represented by the general formula (1) in the positive hole blocking layer. In this case, it is possible to employ the compound represented by the general formula (1) even as a host material of the light-emitting layer, and it is also possible to employ the compound represented by the general formula (1) having the same structure.

(Electron Blocking Layer)

The electron blocking layer has a function of transporting the positive hole in wide meaning. The electron blocking layer has, a role of blocking the electron from reaching the positive hole transporting layer while transporting the positive hole, and with this, it is possible to improve rebonding probability of the electron and the positive hole in the light-emitting layer. It is possible to use the compound represented by the general formula (1) in an electron element layer. In this case, it is possible to employ the compound represented by the general formula (1) even as a host material of the light-emitting layer, and it is also possible to employ the compound represented by the general formula (1) having the same structure. In addition, it is possible to use the compound represented by the general formula (1) even in the positive hole blocking layer, and it is also possible to employ the compound represented by the general formula (1) having the same structure as that used in the electron element layer or the light-emitting layer.

(Exciton Blocking Layer)

The exciton blocking layer is a layer for blocking an exciton generated by rebonding of the positive hole and the electron in the light-emitting layer from being diffused in an electric charge transport layer, it is possible to efficiently confine the exciton in the light-emitting layer by insertion of the layer, and it is possible to improve light emission efficiency of the element. The excition blocking layer comes to be in contact with the light-emitting layer, and can be inserted into any of an anode side and a cathode side, and also can be inerted into both of the anode side and the cathode side. That is, in a case where the exciton blocking layer is on the anode side, it is possible to insert the layer between the positive hole transport layer and the light-emitting layer, being in contact with the light-emitting layer, and in a case where the exciton blocking layer is on the cathode side, it is possible to insert the layer between the light-emitting layer and the and the cathode, being in contact with the light-emitting layer. In addition, a positive hole injection layer, an electron blocking layer, or the like can be included between the anode and the exciton blocking layer in contact with the anode side of the light-emitting layer, and an electron injection layer, an electron transport layer, a positive, hole blocking layer, and the like can be included between the cathode and the exciton blocking layer in contact with the cathode side of the light-emitting layer. In a case where a blocking layer is disposed, at least one of excited singlet energy and excited triplet energy of the material used as the blocking layer is preferably higher than the excited singlet energy and the excited triplet energy of the light-emitting material.

(Positive Hole-Transport Layer)

The positive hole transport material is formed of a positive hole transport material having a function of transporting the positive hole, and the positive hole transport layer can be provided as a single layer or a plurality of layers.

The positive hole transport layer has any of injection or transport of the positive hole and barrier properties of the electron, and may be any of an organic substance and an inorganic substance. Examples of a usable known positive hole transport material include a triazole derivative, an oxadiazole derivative, an imidazole derivative, a carbazole derivative, an indolocarbazole derivative, a polyarylalkane derivative, a pyrazoline derivative and a pyrazolone derivative, a phenylene diamine derivative, an arylamine derivative, an amino-substituted chalcone derivative, an oxazole derivative, a styrylanthracene derivative, a fluorenone derivative, a hydrazone derivative, stilbene derivative, a silazane derivative, an aniline-based copolymer, and a conductive polymer oligomer, and particularly include thiophene oligomer, but it is preferable to use a porphyrin compound, an aromatic tertiary amine compound, and a styrylamine compound, and it is more preferable to use an aromatic tertiary amine compound.

(Electron Transport Layer)

The electron transport layer is formed of a material having a function of transporting an electron, and the electron transport layer can be provided as a single layer or a plurality of layers.

The electron transport material (also used as a positive hole blocking material in some cases) may have a function of transferring an electron inserted by a cathode to the light-emitting layer. Examples of a usable electron transport layer include a nitro-substituted fluorene derivative, a diphenylquinone derivative, a thiopyran dioxide derivative, carbodiimide, a fluorenylidene methane derivative, anthraquinodimethane and an anthrone derivative, an oxadiazole derivative, and the like. In addition, it is also possible to use a thiadiazole derivative obtained by substituting an oxygen atom of an oxadiazole ring with a sulfur atom and a quinoxaline derivative having a quinoxaline ring known as an electron-attracting group, as the electron transport material in the oxadiazole derivative. In addition, it is also possible to use a polymer material in which the material is introduced into a polymer chain, or a polymer material in which the material is used as a main chain of a polymer.

When preparing an organic electroluminescence element, the compound represented by the general formula (1) may be not only used in a single-layered organic layer (for example, electron transport layer) but also used in a plurality of organic layers. At this time, the compound represented by the general formula (1) used in each organic layer may be the same, or may be different. For example, the compound represented by the general formula (1) may be used in the injection layer, the blocking layer, the positive hole blocking layer, the electron blocking layer, the exciton blocking layer, the positive hole transport layer, and the like, in addition to the electron transport layer or the light-emitting layer. The method of film-forming of these layers is not particularly limited, and a dry process, a wet process, or the like may be used.

Hereinafter, a preferable material capable of being used in the organic electroluminescence element will be specifically exemplified. However, the material capable of being used in the present invention is not limitedly interpreted by the compounds exemplified below. In addition, the compound exemplified as a material having a specific function can be divertedly used as a material having other functions. R, R', and $R_1$ to $R_{10}$ in a structure formula of the exemplified compounds below each independently represent a hydrogen atom or a substituent. X represents a carbon atom forming a ring skeleton or a hetero atom, n represents an integer of 3 to 5, Y represents a substituent, and m represents an integer of 0 or more.

First, preferable compounds capable of being used even as a host material of the light-emitting layer are exemplified.

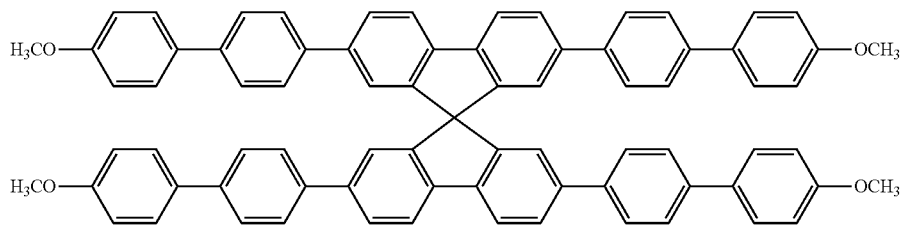

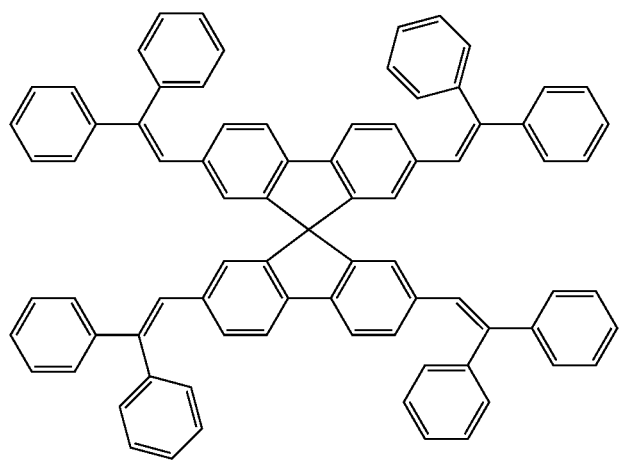

-continued
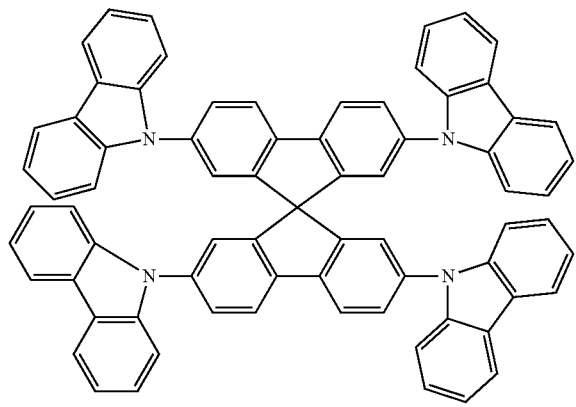
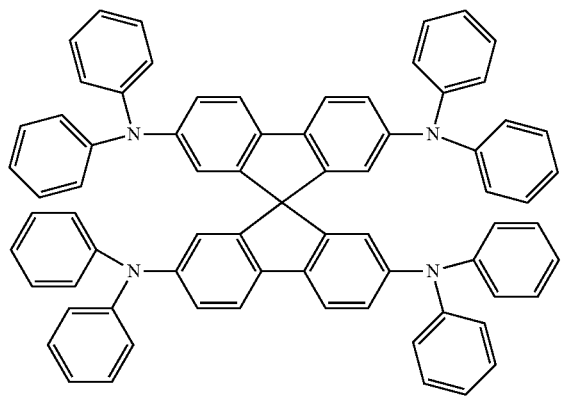
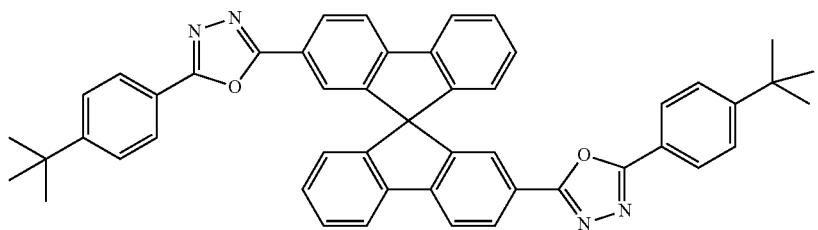
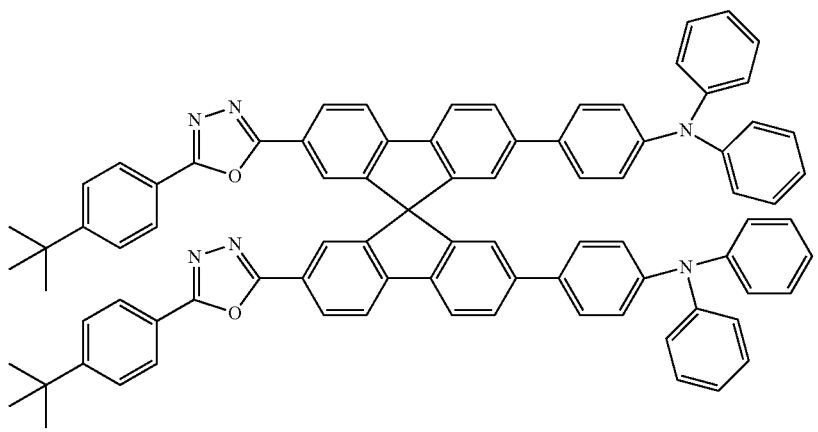

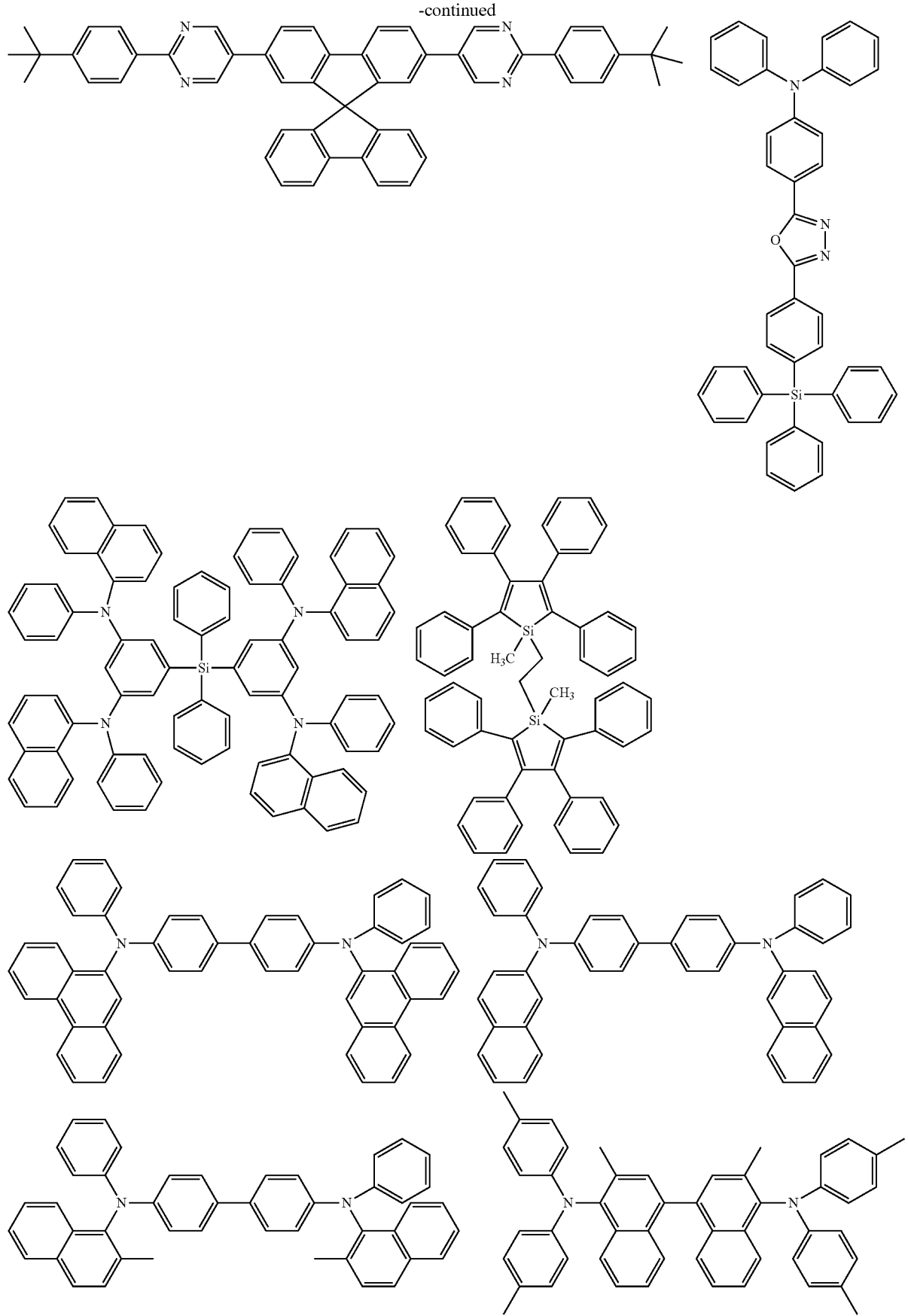

65
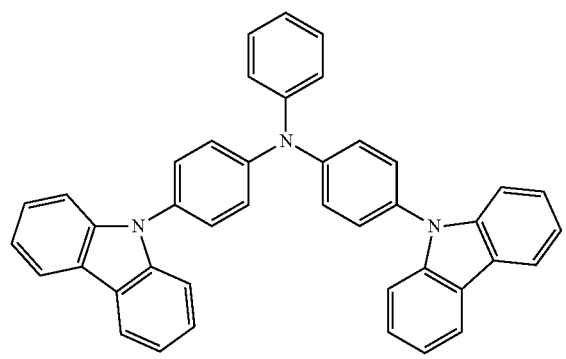
66
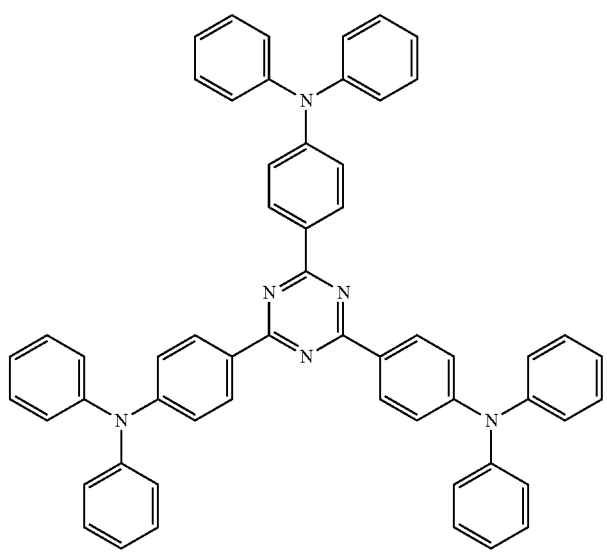
-continued
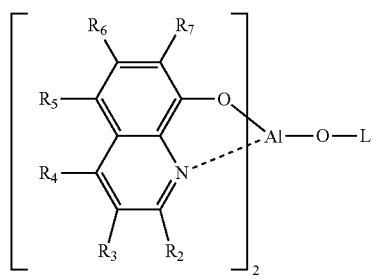 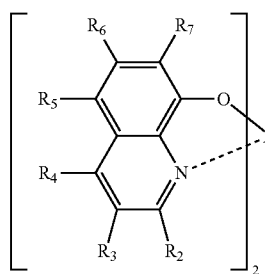 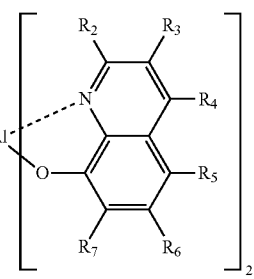
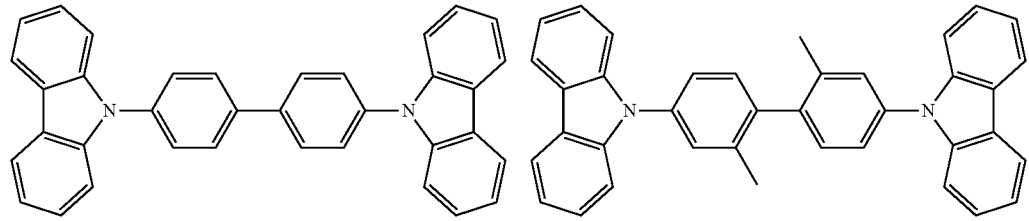
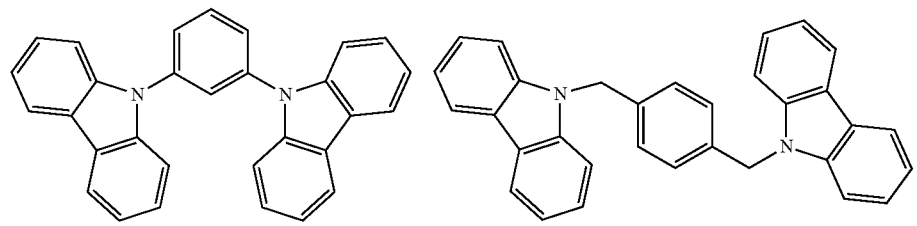
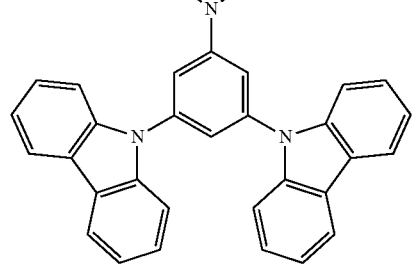 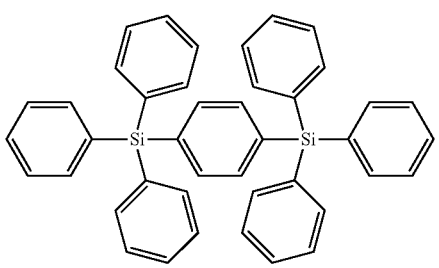

-continued
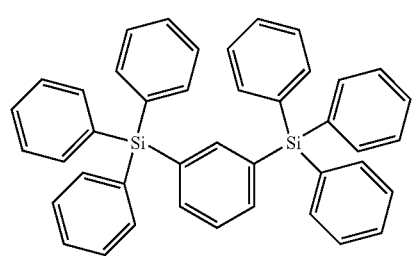
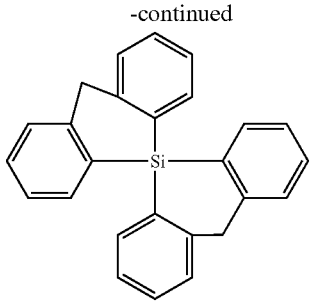
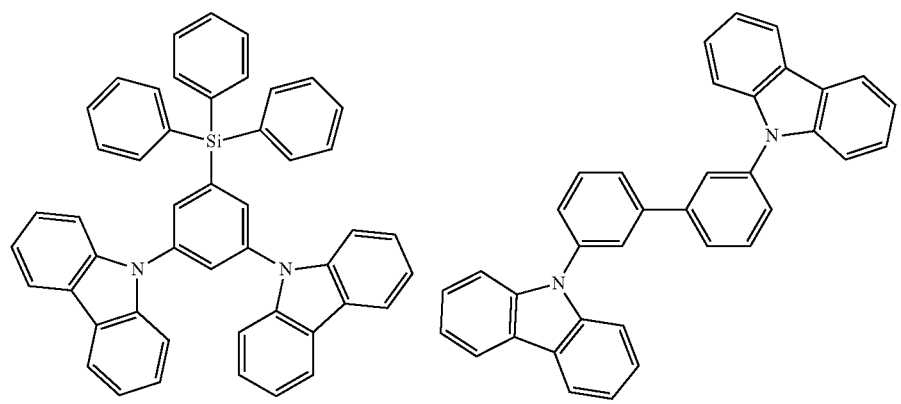
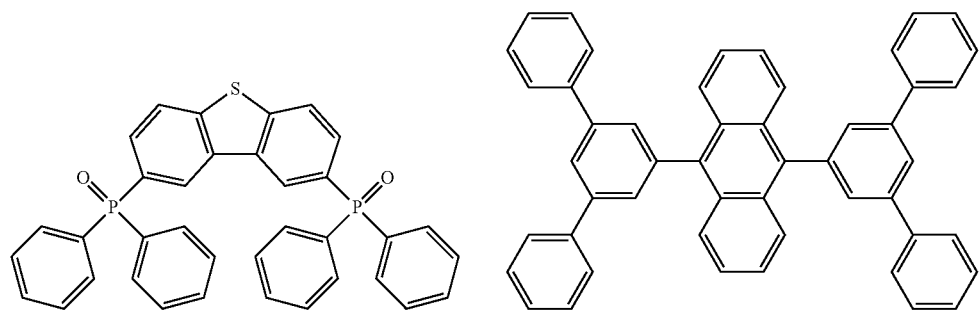
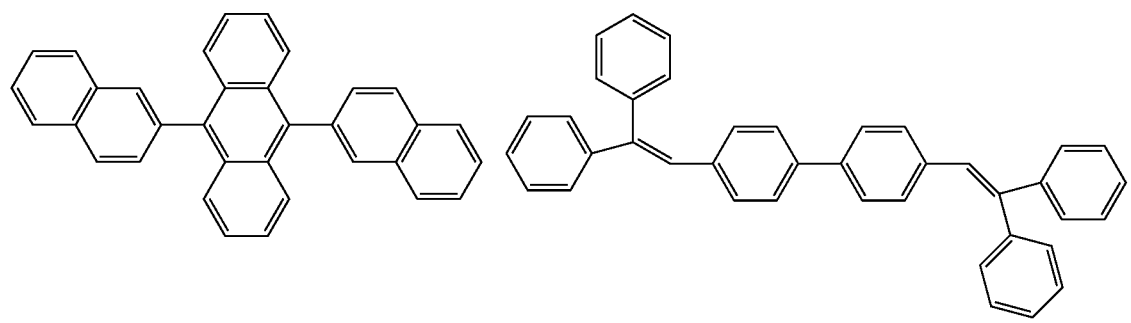

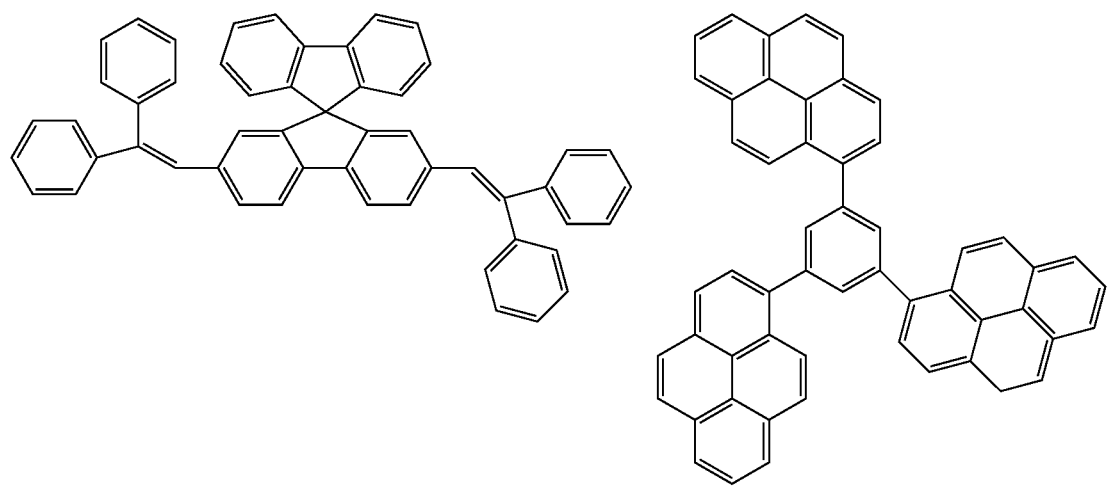
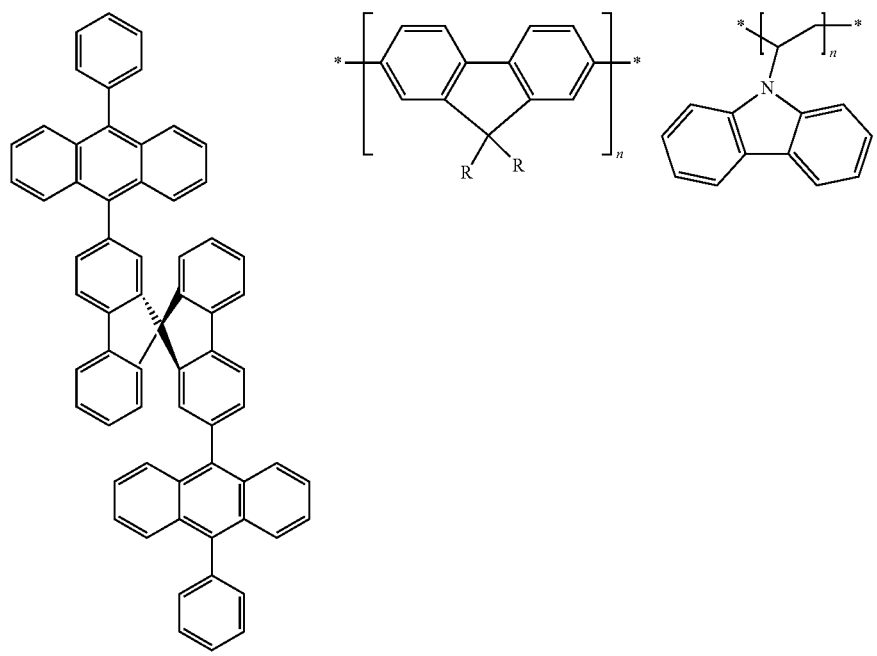
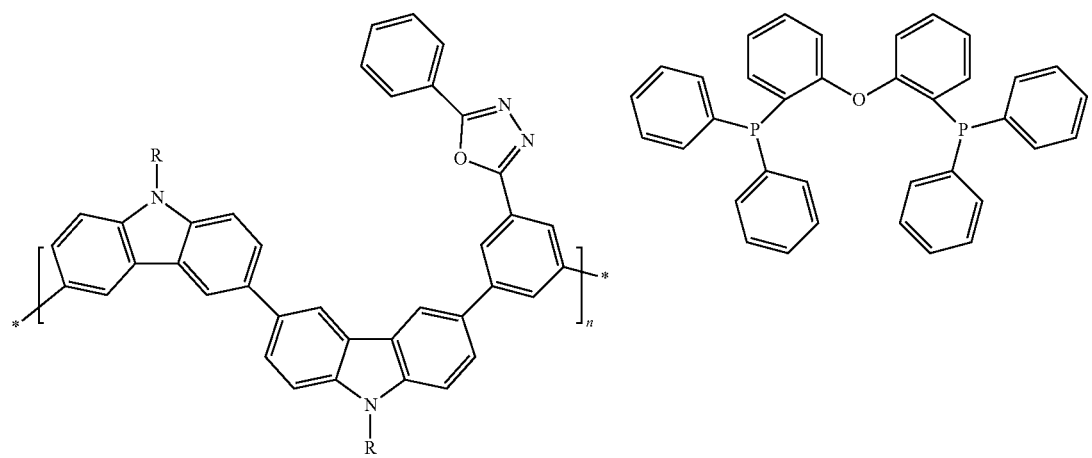

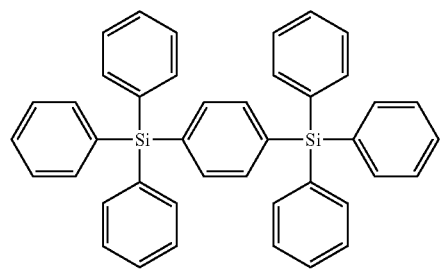
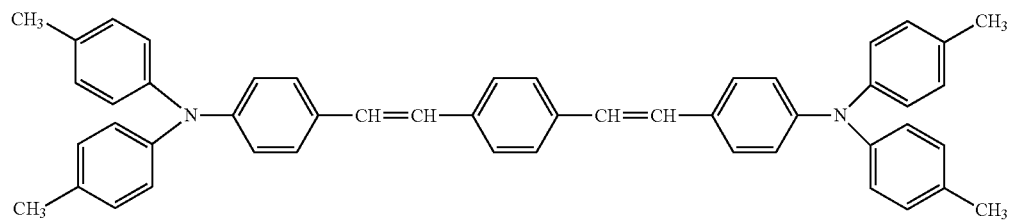
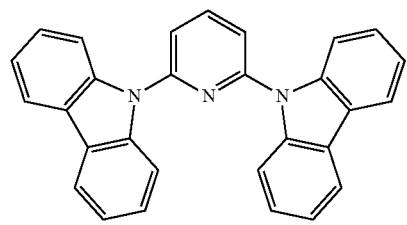
Preferable compounds capable of being used as a positive hole injection material are exemplified.
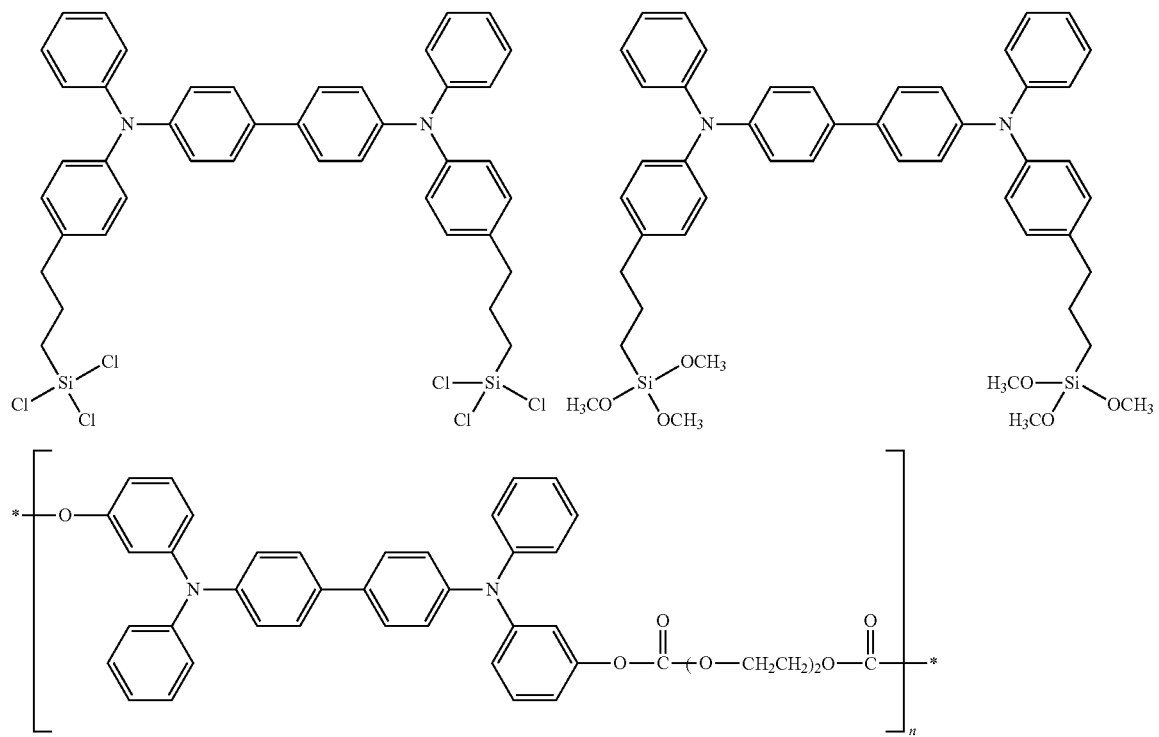

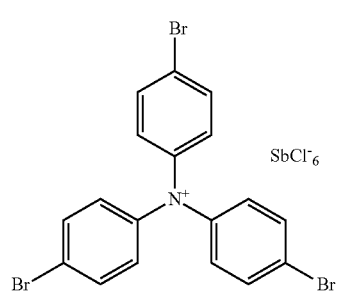
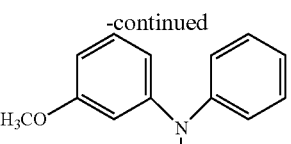
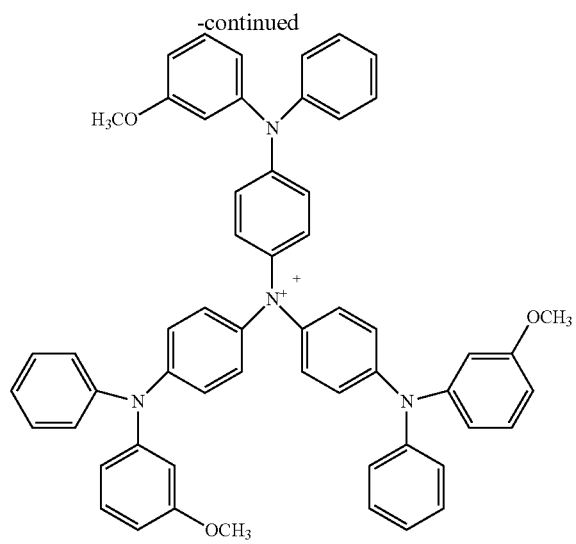
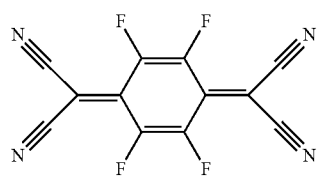
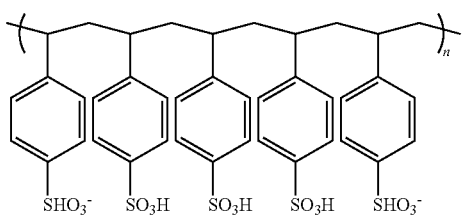
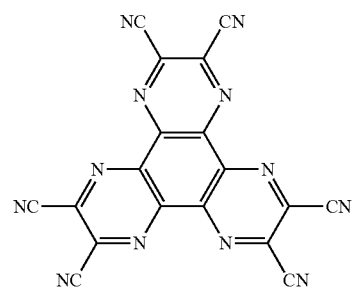
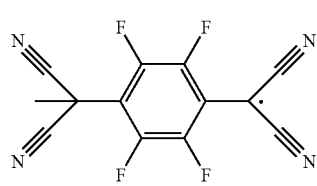
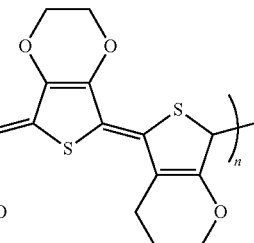
Subsequently, compounds capable of being used as a positive hole transport material are exemplified.
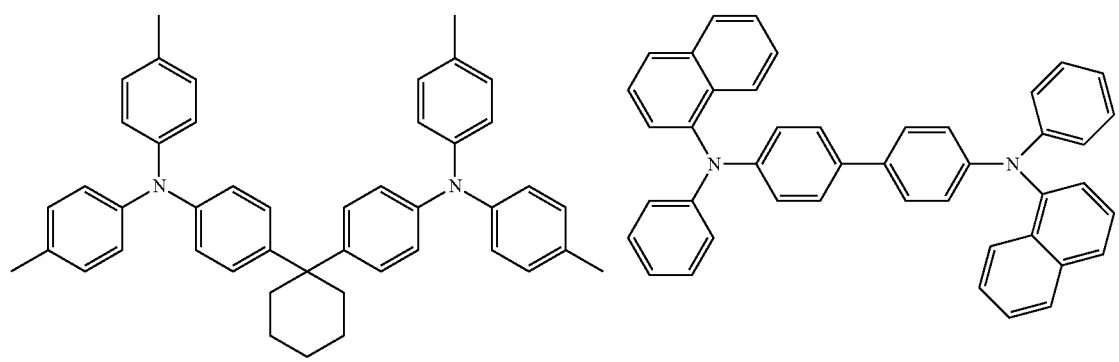

-continued
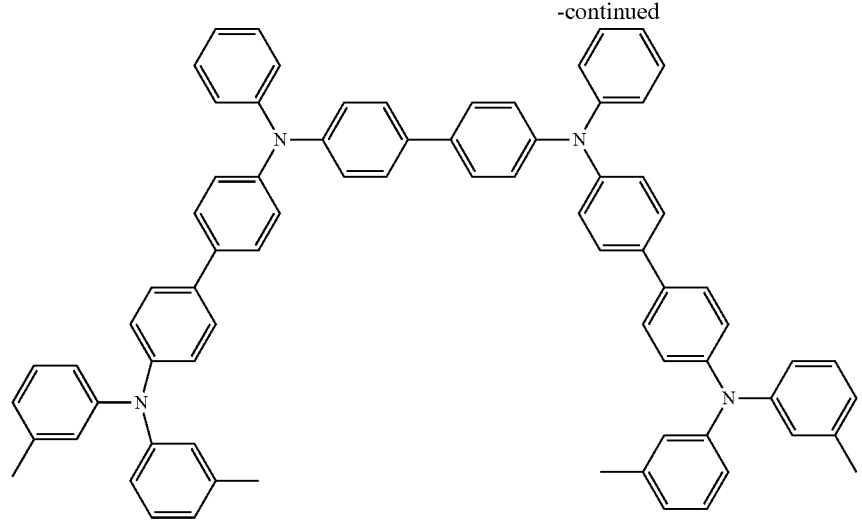
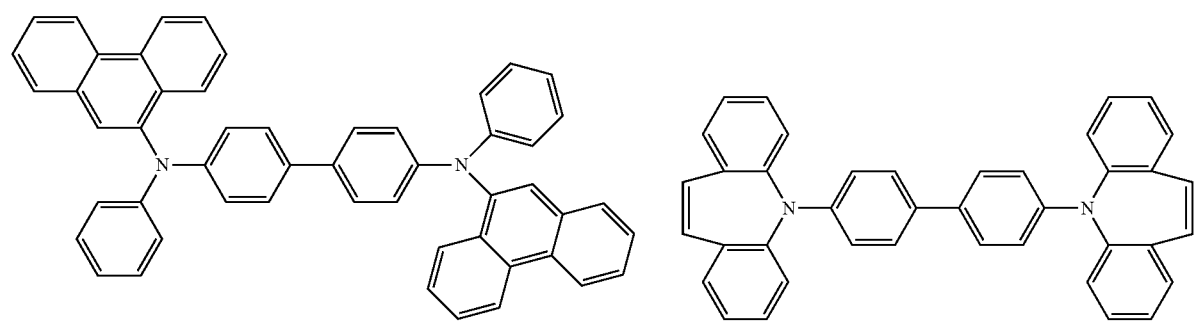
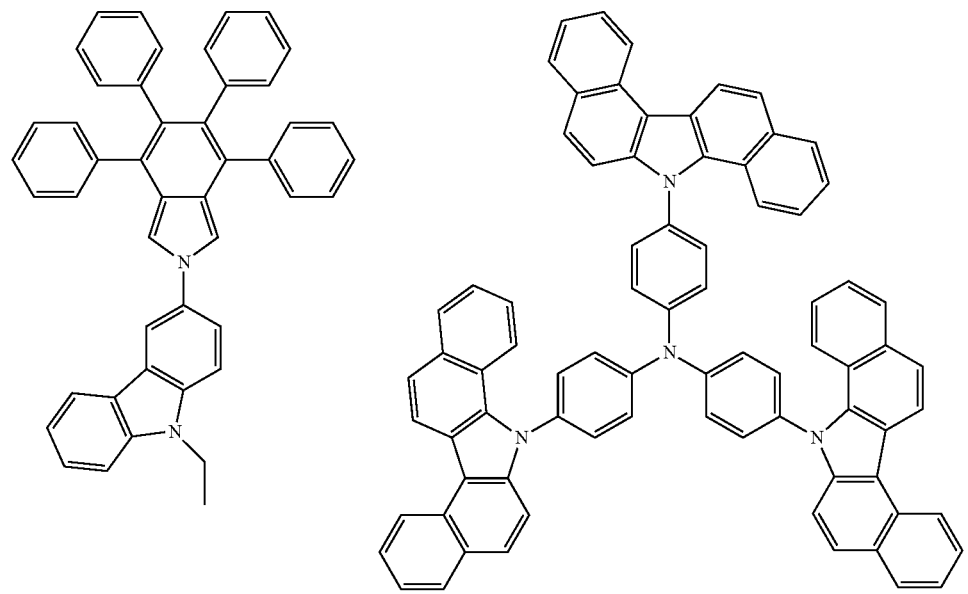

-continued
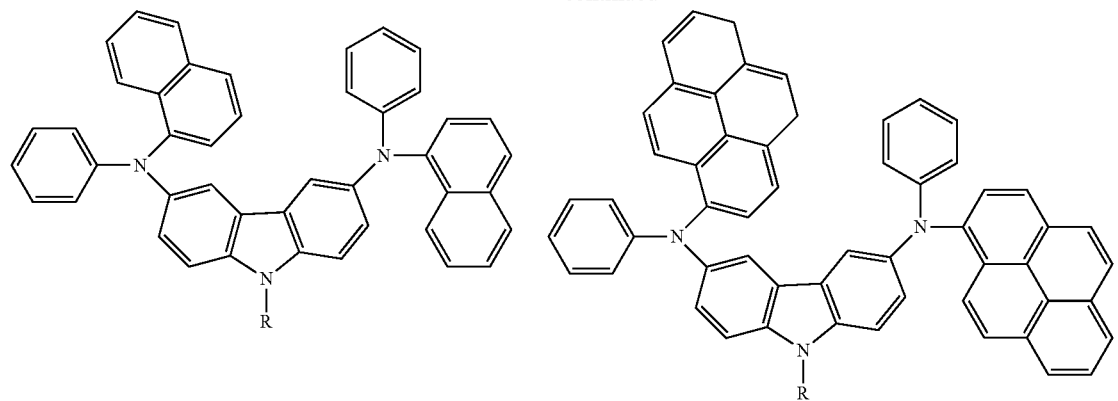
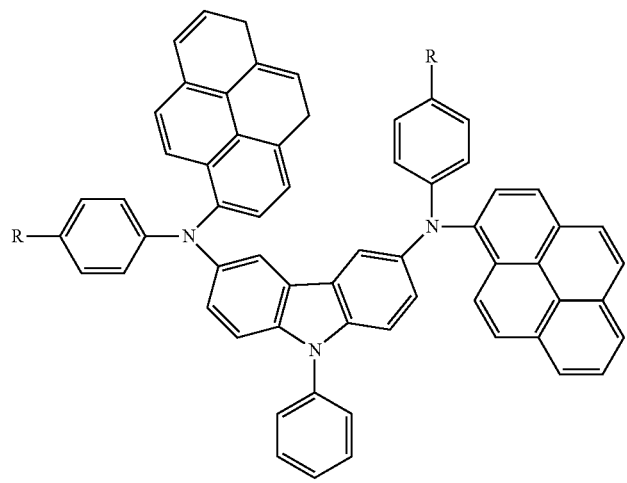
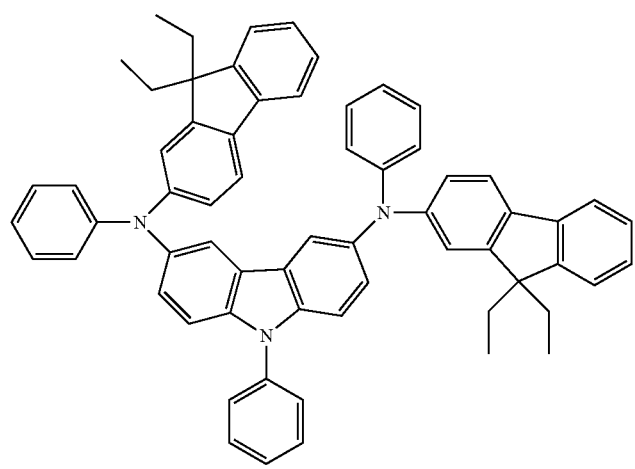

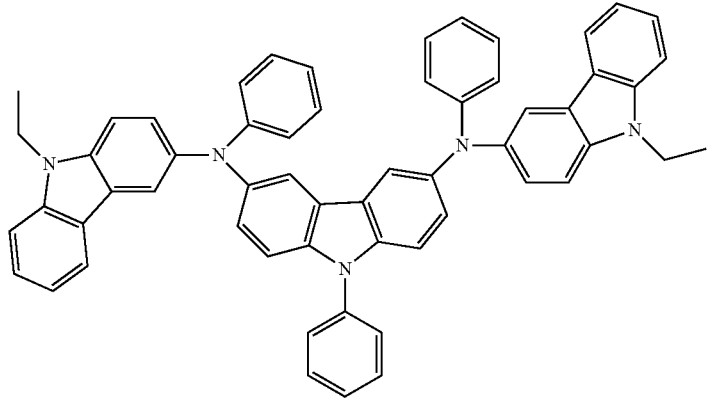
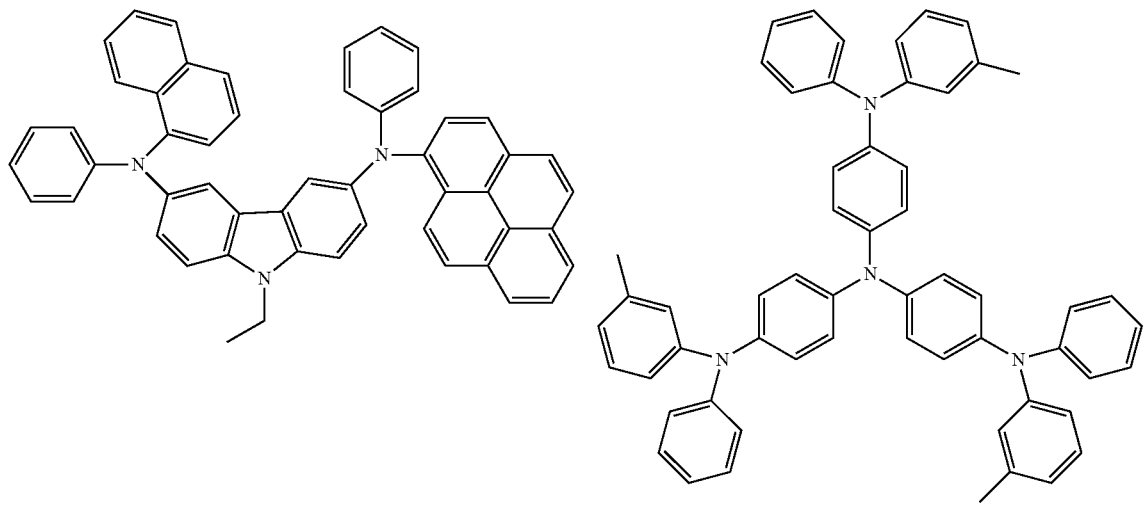
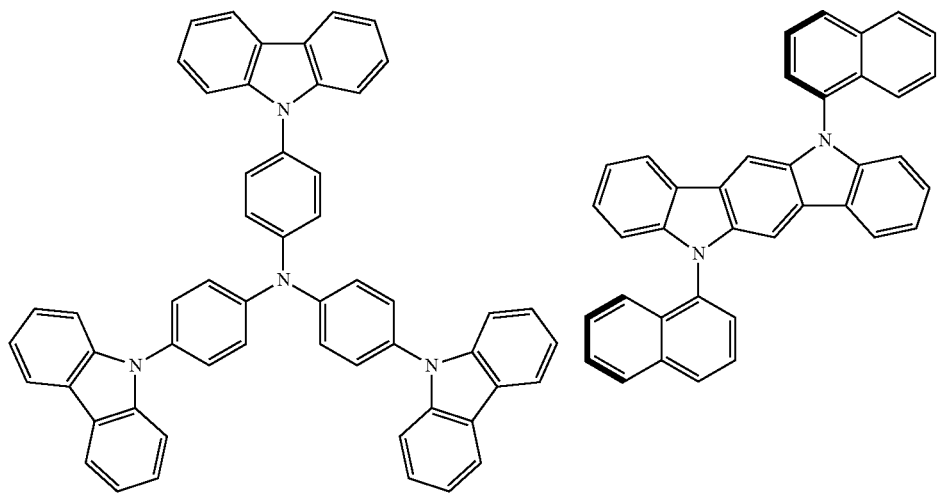

-continued
81
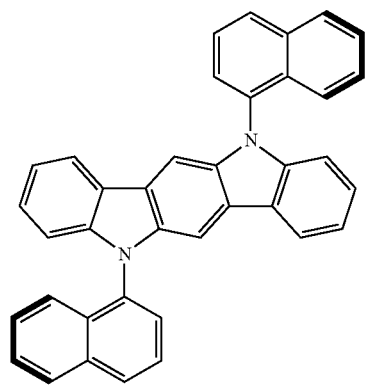
82
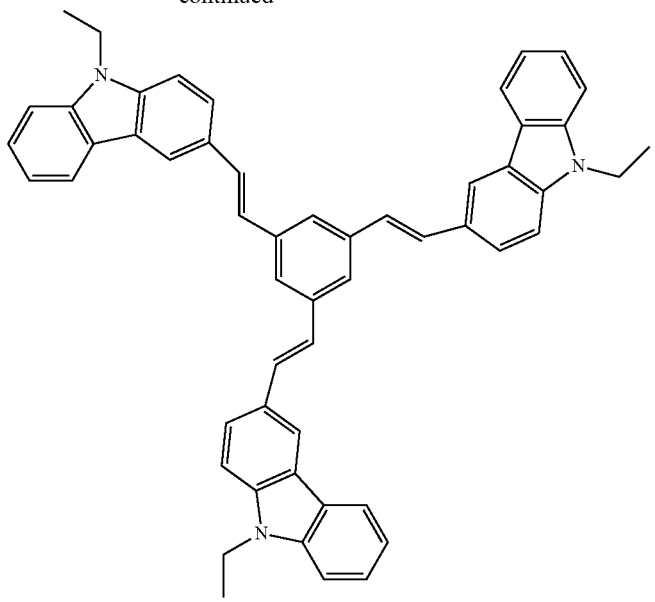
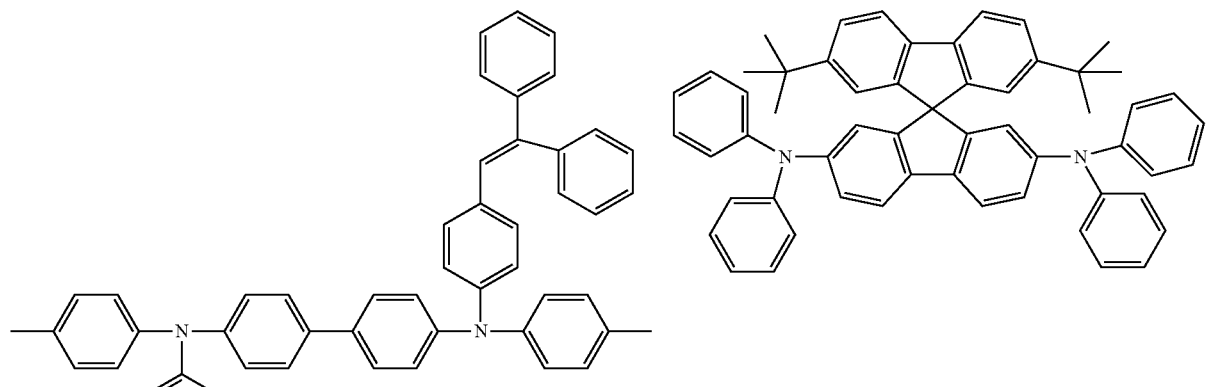
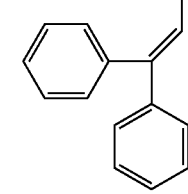
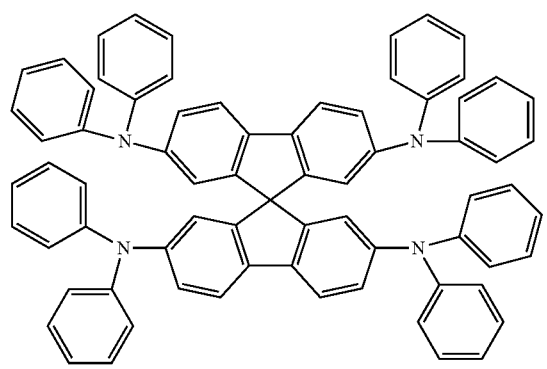
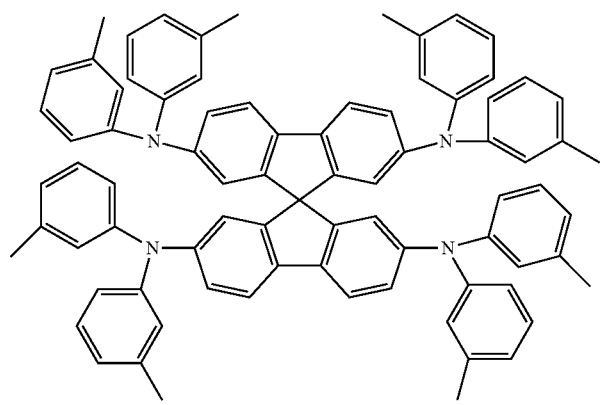

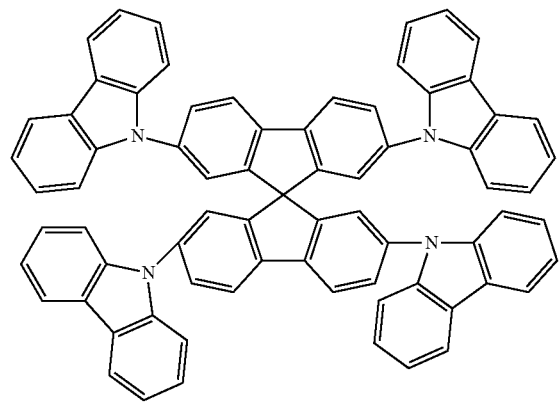
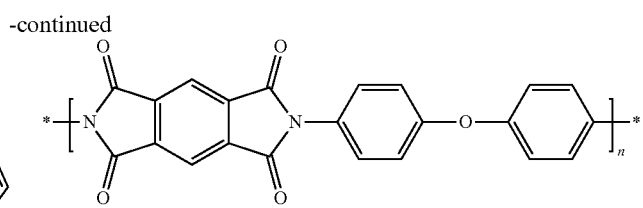
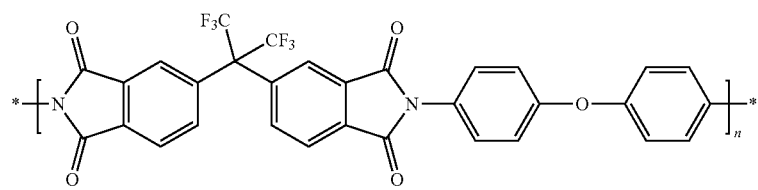
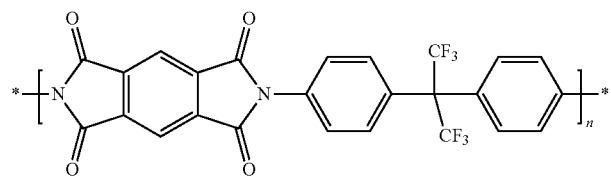
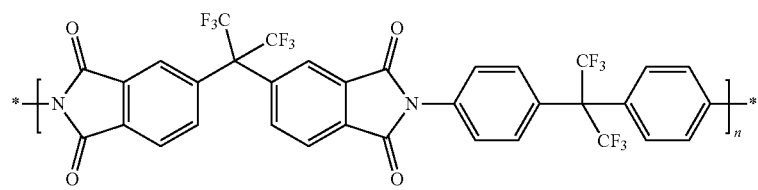
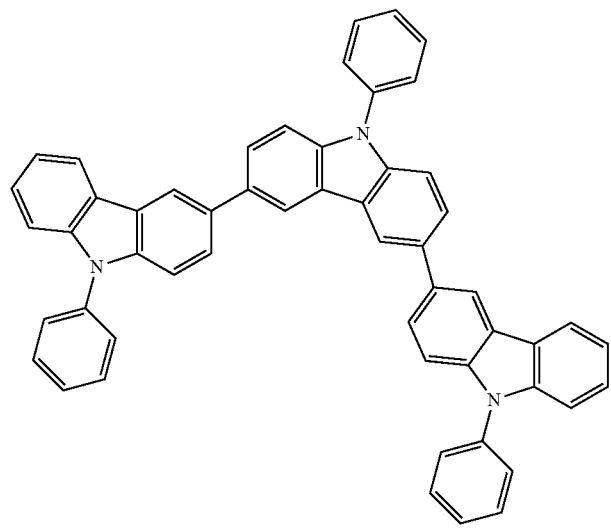
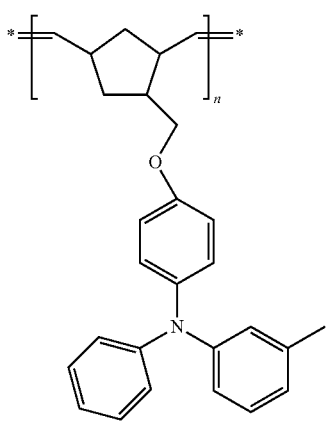

85 86
-continued
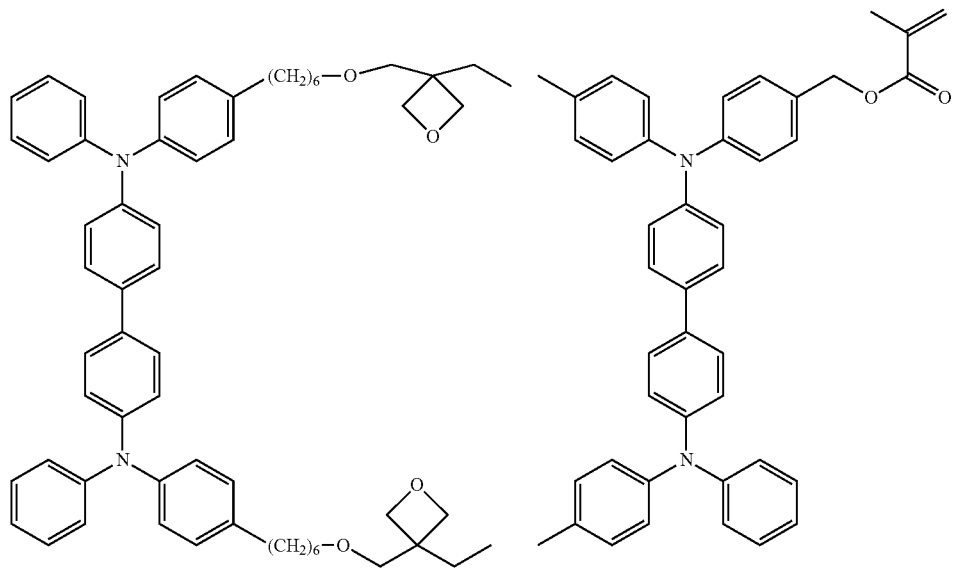
R =
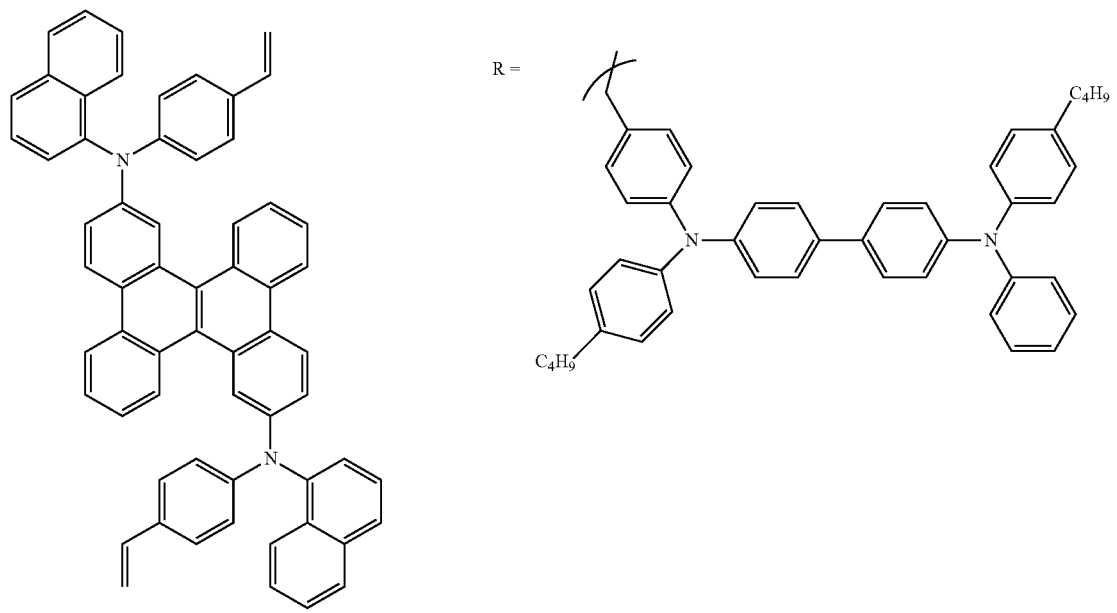
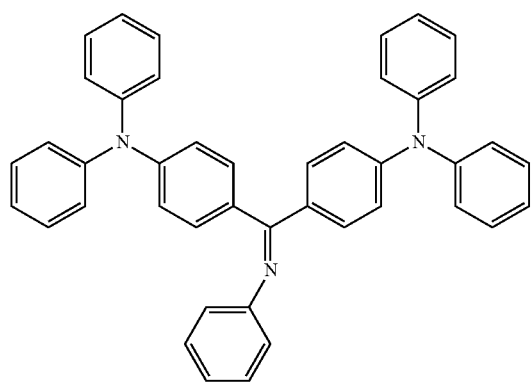

-continued
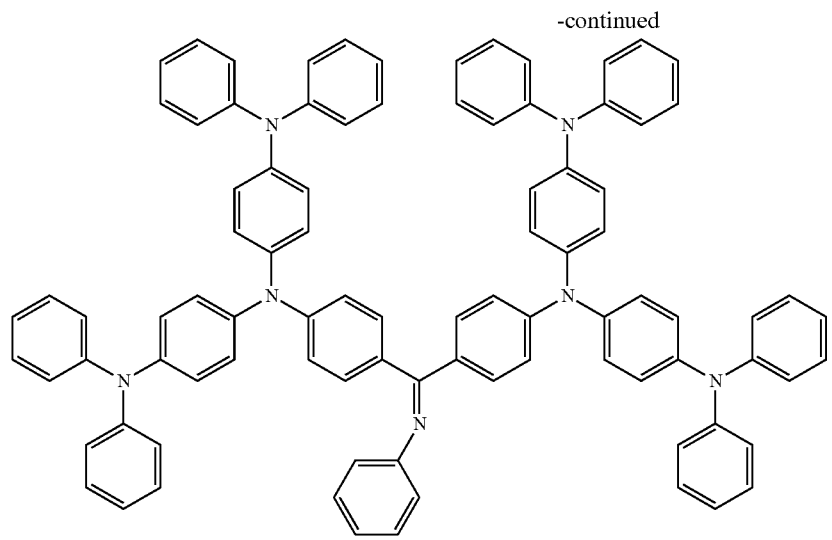
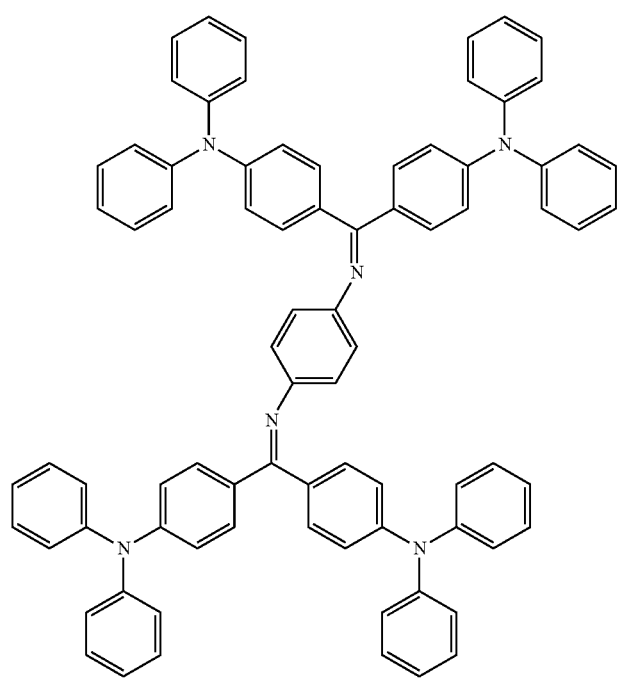

-continued
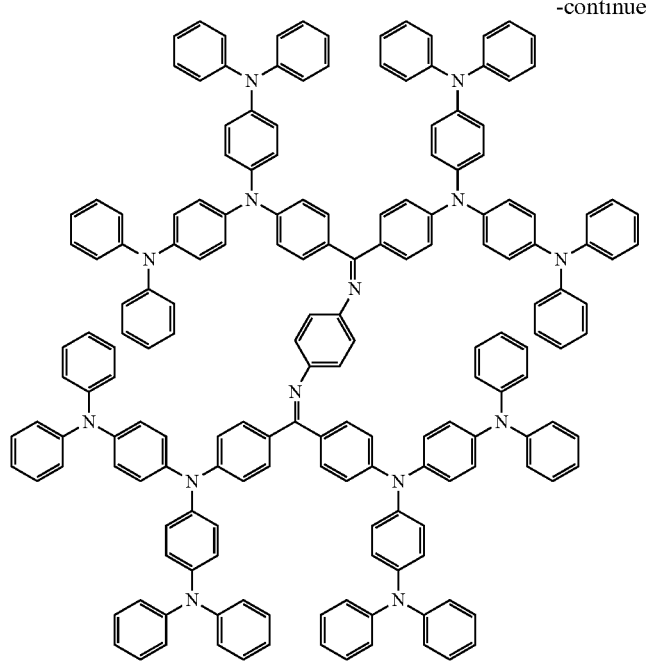
89
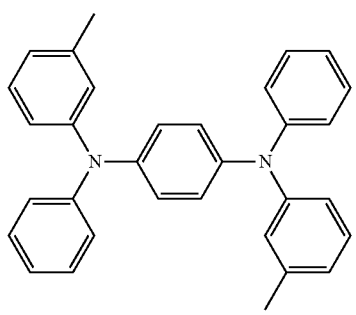
90
Subsequently, preferable compounds capable of being used as an electron blocking material are exemplified.
-continued
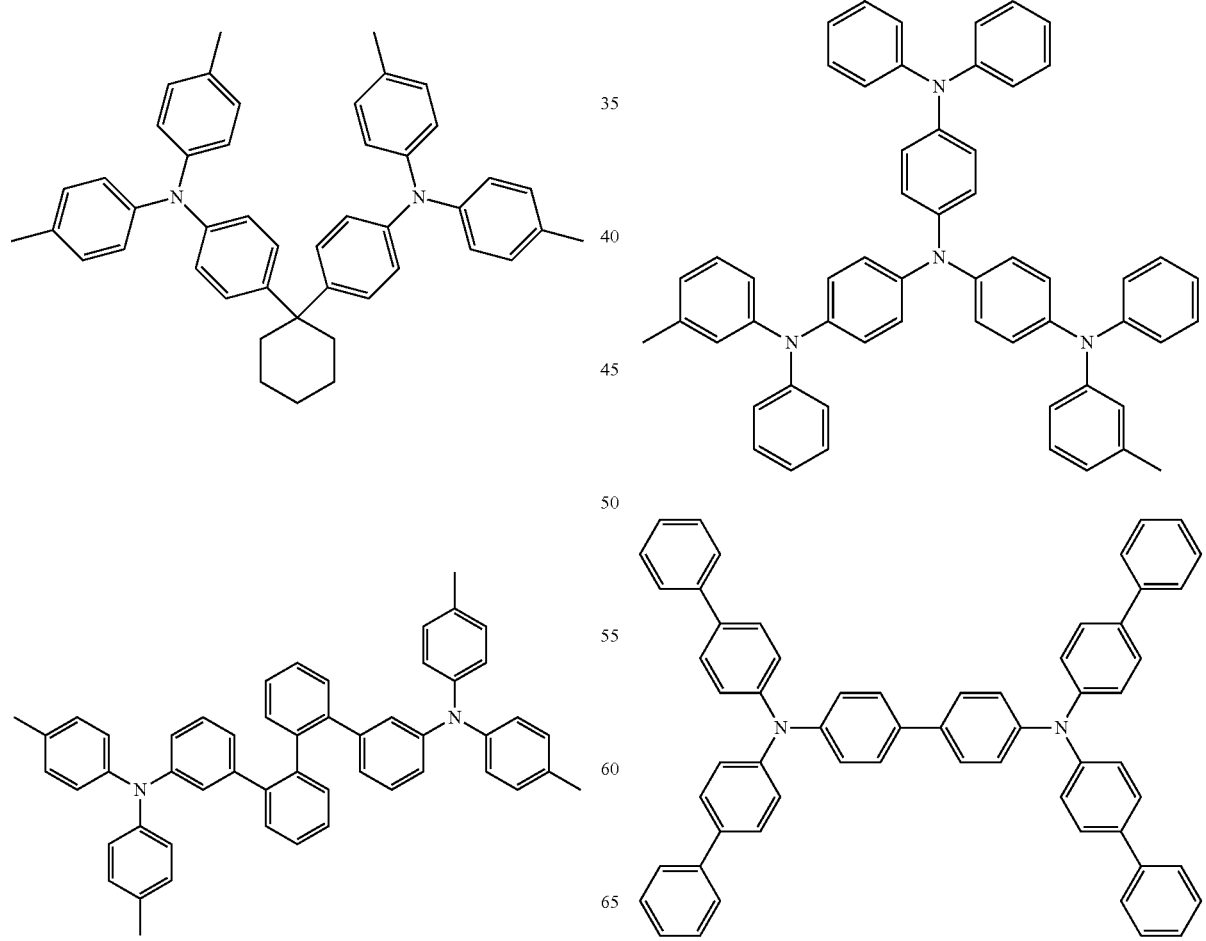

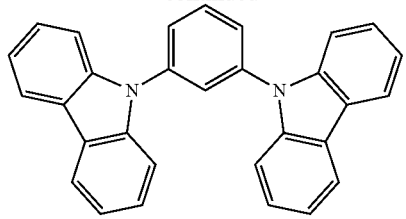
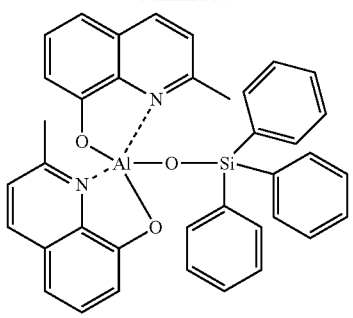
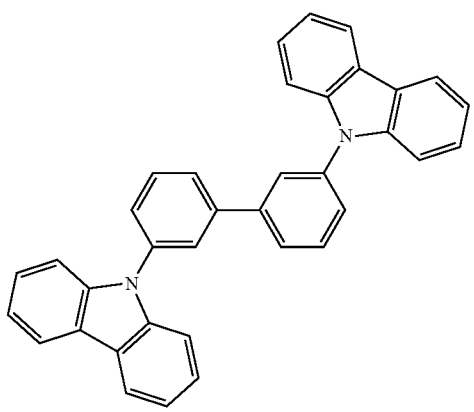
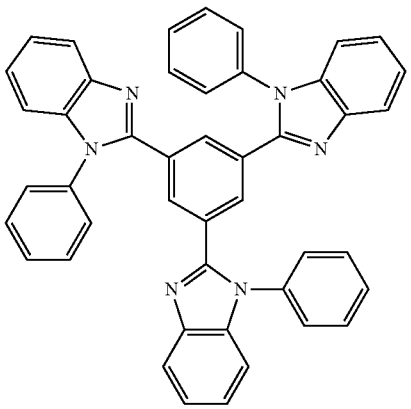
Subsequently, preferable compounds capable of being used as a positive hole blocking material are exemplified.
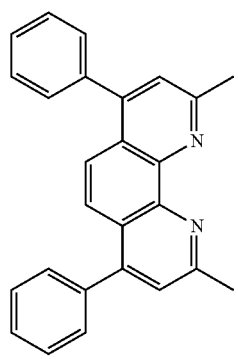
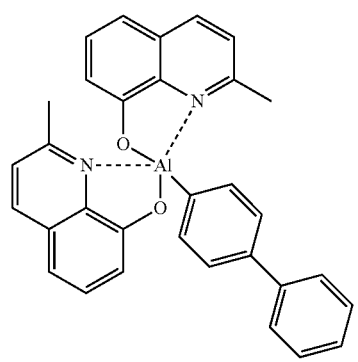
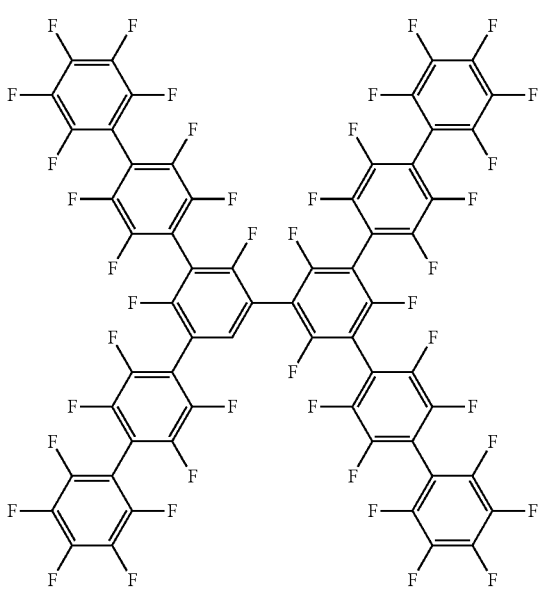

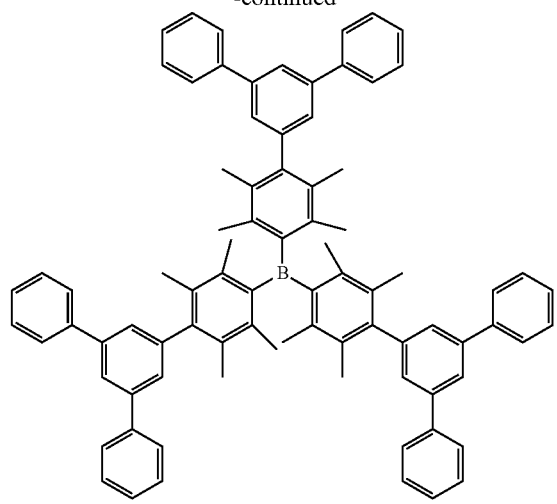
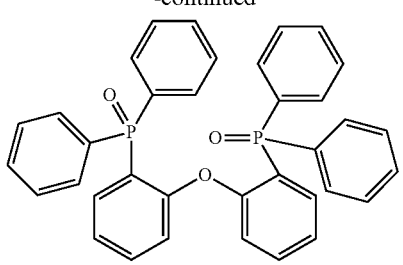
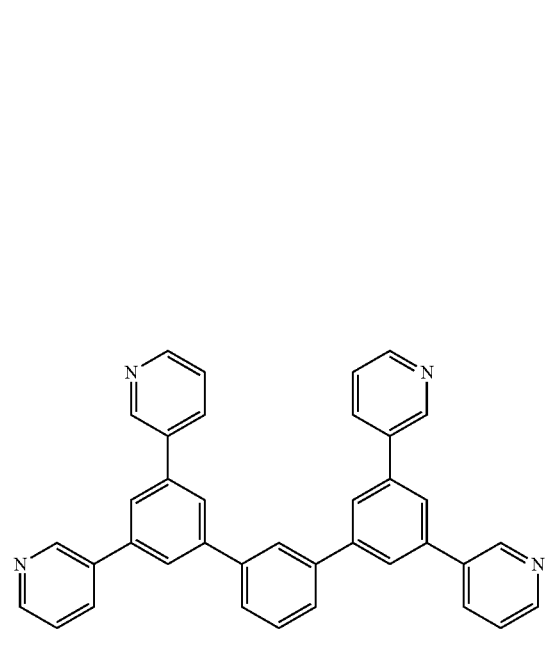
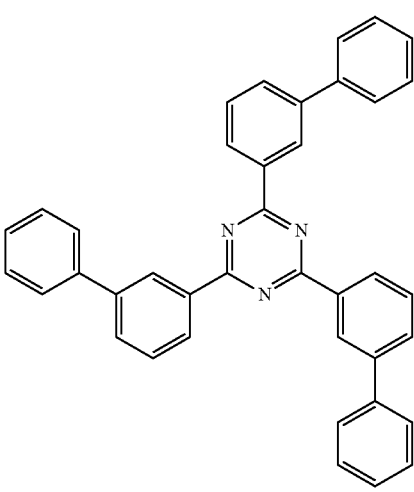
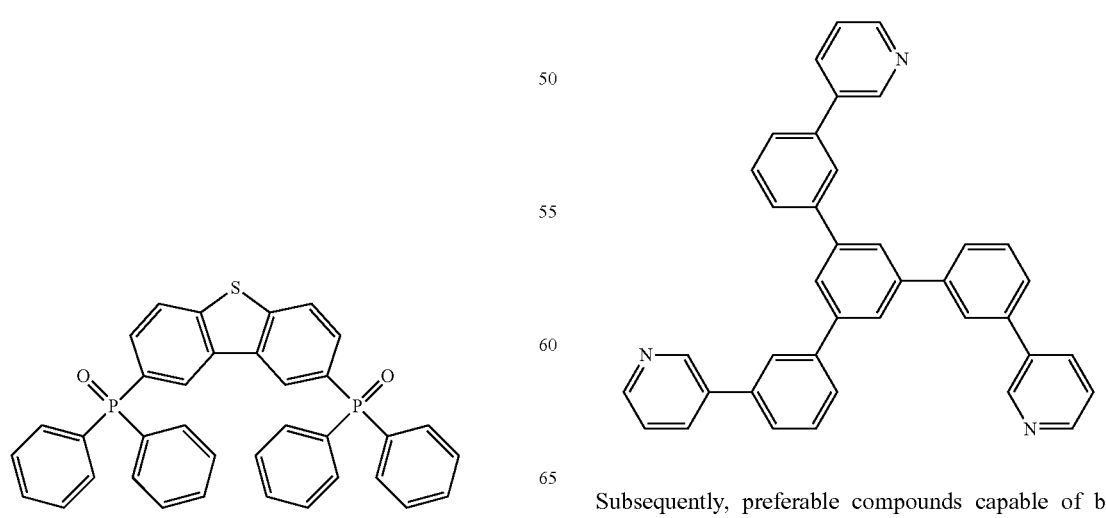
Subsequently, preferable compounds capable of being used as an electron transport material are exemplified.

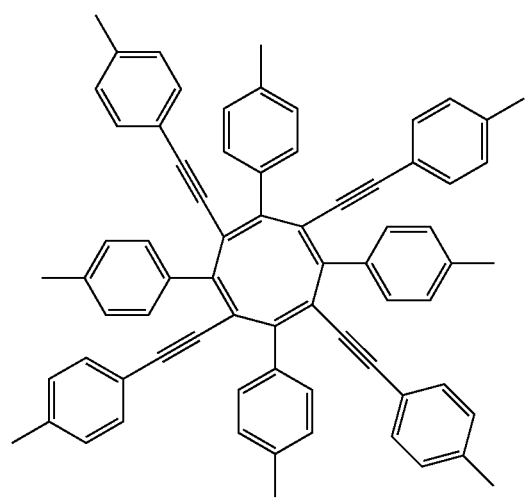
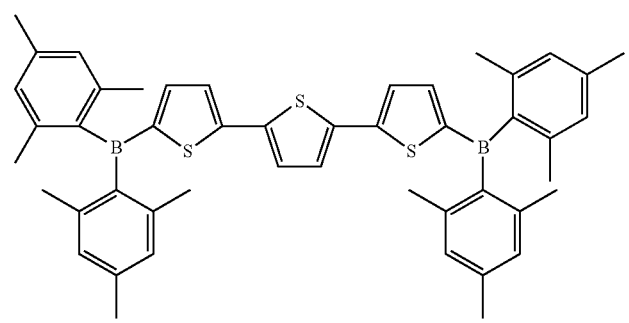
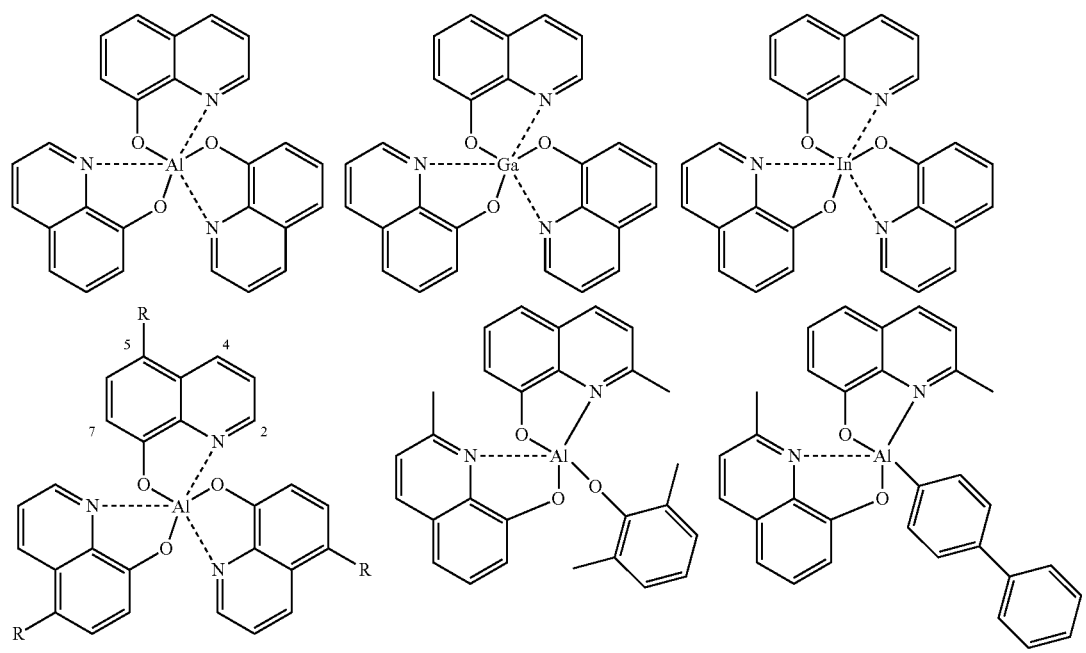
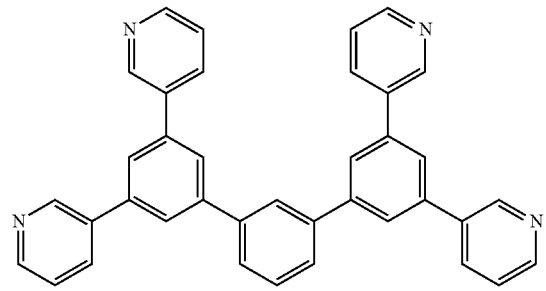
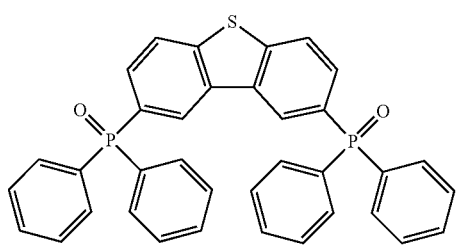
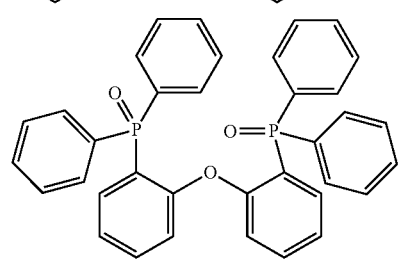
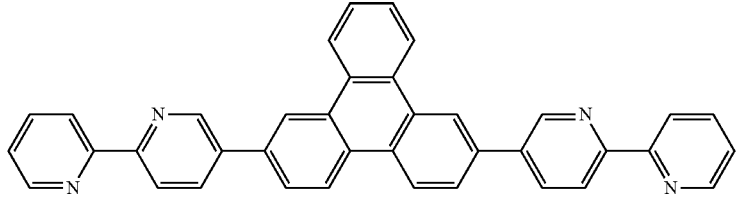

-continued
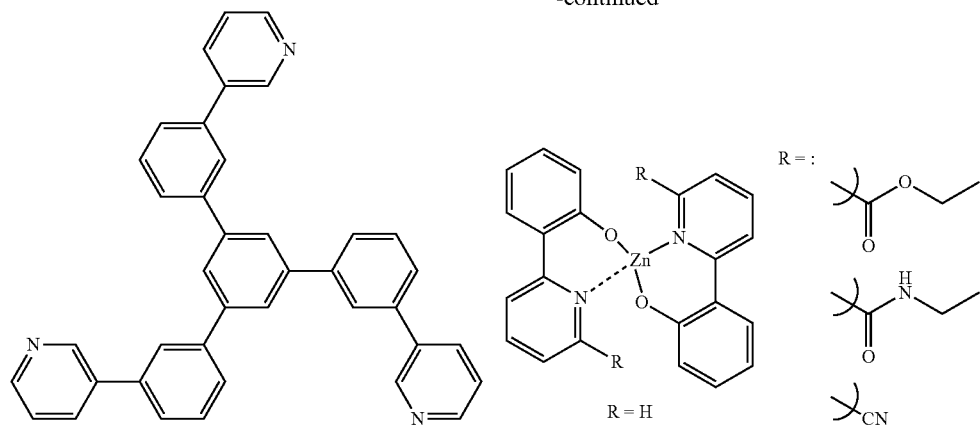
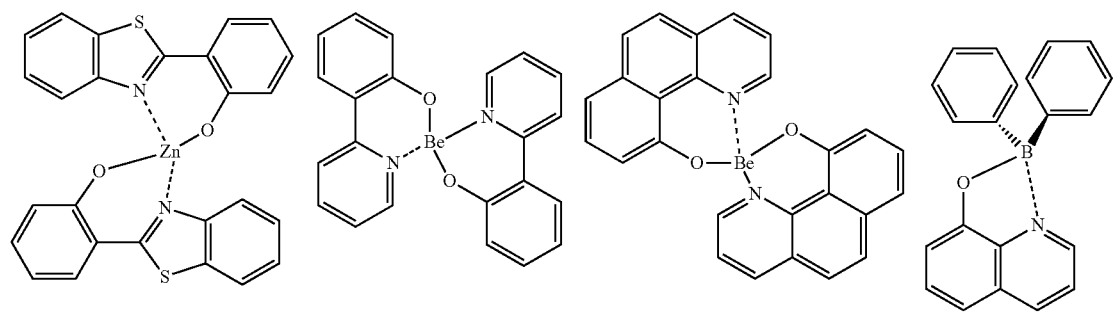
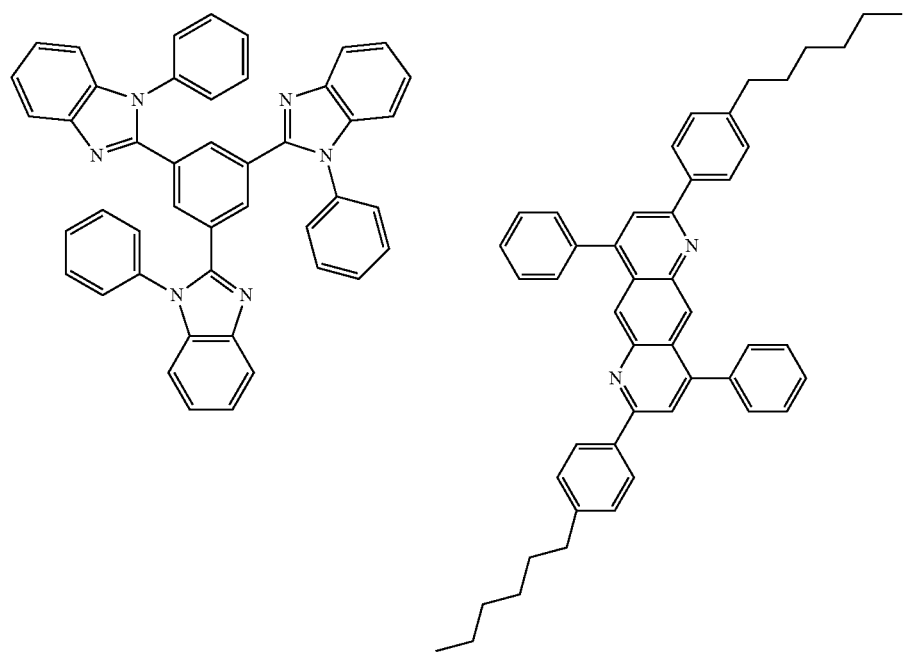

99
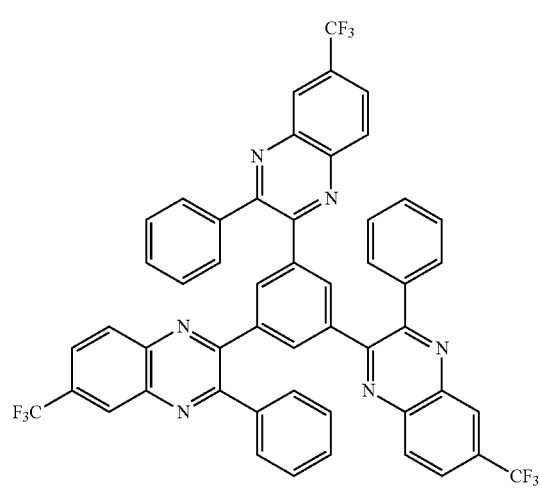
100
-continued
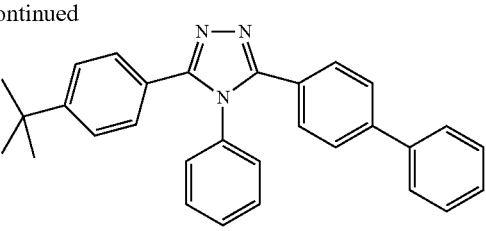
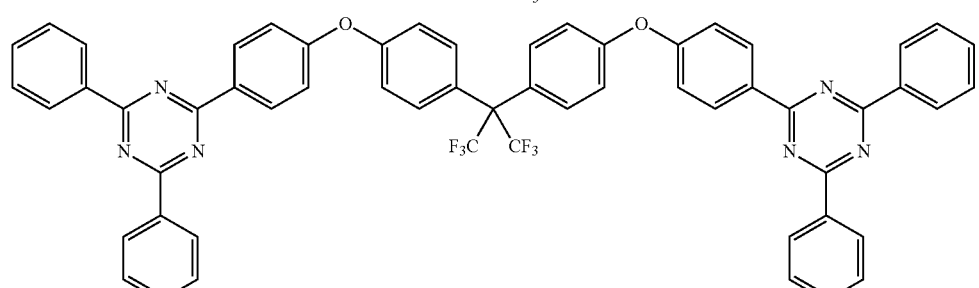
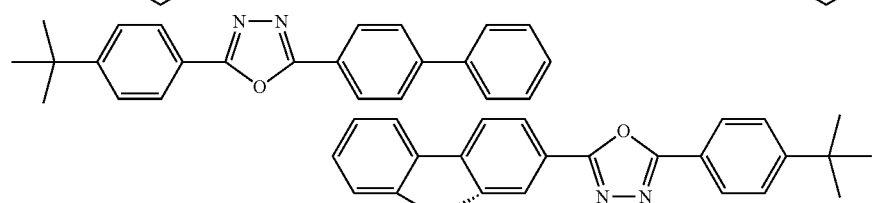
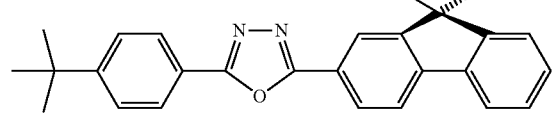
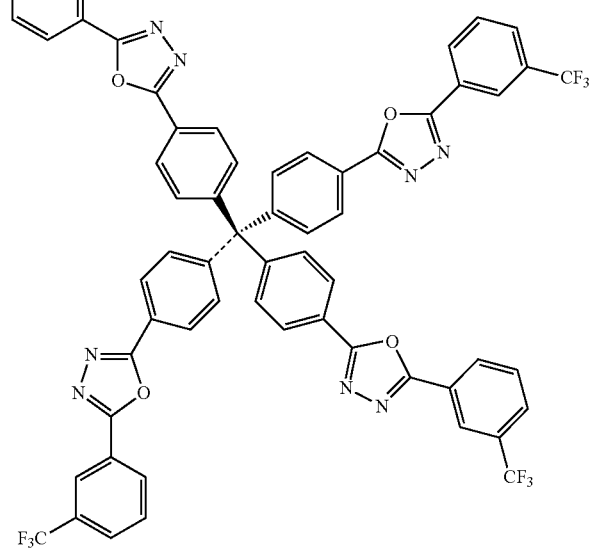

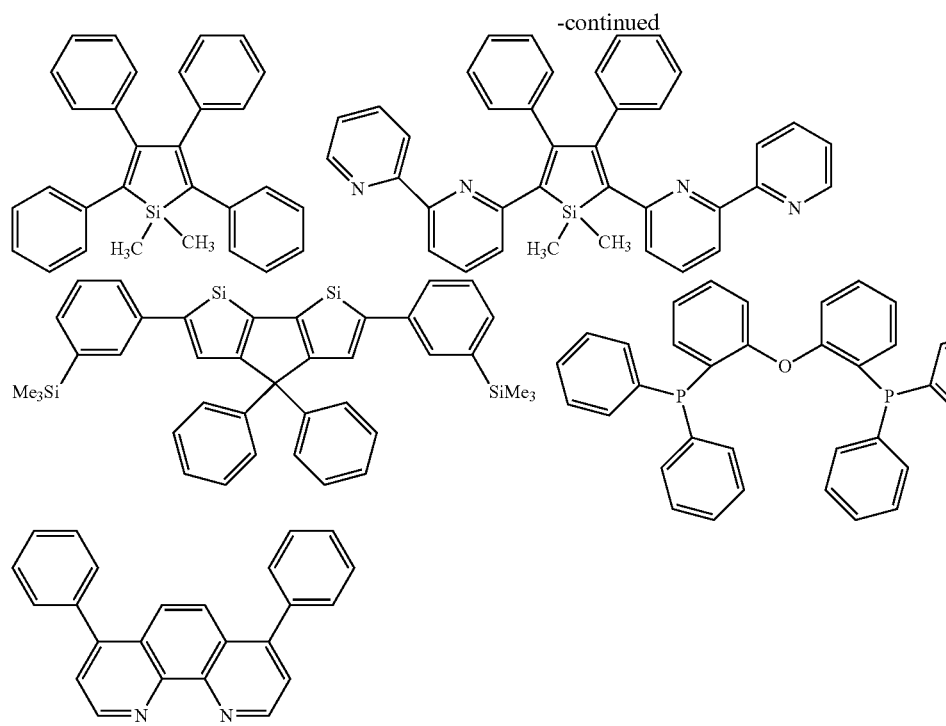
Subsequently, preferable compounds capable of being used as an electron injection material are exemplified.
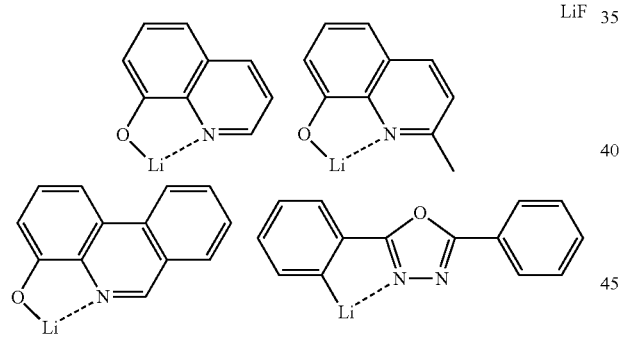
LiF
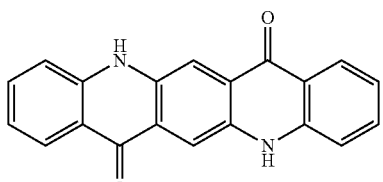
In addition, preferable compounds as a material capable of being added are exemplified. For example, it is considered that the compounds are added as a stabilizing material.
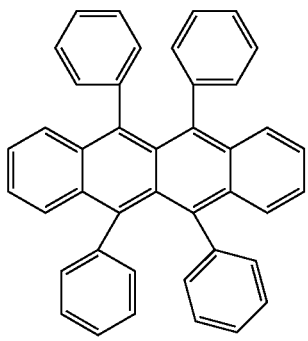
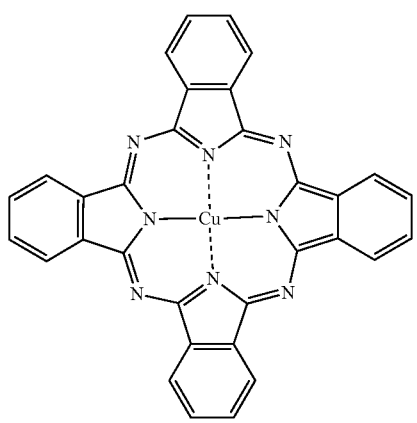

-continued

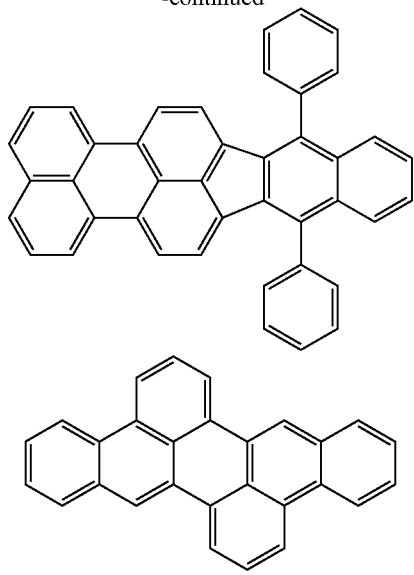

The organic electroluminescence element prepared by the above-described method emits light by applying an electric field between an anode and a cathode of the obtained element. At this time, if light is emitted by excited singlet energy, light of a wavelength in accordance with the energy level is checked as fluorescence light emission and delayed fluorescence light emission. In addition, if light is emitted by excited triplet energy, a wavelength in accordance with the energy level is checked as phosphorescence. General, fluorescence has a shorter fluorescence life than the delayed fluorescence light emission and thus light emission life can be distinguished by fluorescence and delayed fluorescence.

On the other hand, regarding phosphorescence, in a general organic compound such as the compound of the present invention, excited triplet energy is not stable, a rate constant of thermal deactivation is large, a rate constant of light emission is small and is immediately deactivated, and thus phosphorescence is hardly observable at room temperature. In order to measure the excited triplet energy of the general organic compound, it is possible to measure the excited triplet energy of the general organic compound by observing light emission under a condition of an extremely low temperature.

The organic electroluminescence element of the present invention is applicable to any of a single element, an element having a structure of being disposed in an array shape, and a structure in which an anode and a cathode are disposed in an X-Y matrics shape. According to the present invention, by the light-emitting layer containing the compound represented by the general formula (1), an organic light-emitting element with significantly improved light emission efficiency is obtained. An organic light-emitting element such as the organic electroluminescence element of the present invention is also applicable to various uses. For example, it is possible to produce an organic electroluminescence display device by using the organic electroluminescence element of the present invention, and for more details, it is possible to refer to "Organic EL Display" (Ohmsha, Ltd.) co-written by Shizuka Tokito, Adachi Chihaya, and Murata. Hideyuki. In addition, the organic electroluminescence element of the present invention can be particularly applicable to organic electroluminescence illumination or backlight for which demands are large.

EXAMPLES

Hereinafter, features of the present invention will be further specifically described with reference to synthesis examples and examples. Materials, treatment content, treatment procedures, and the like shown below can be appropriately changed within a range of not departing the gist of the present invention. Therefore, the scope of the present invention should not be limitedly interpreted by specific examples shown below. Measurement of ultraviolet absorption spectrum was performed by using LAMBDA950-PKA (manufactured by PerkinElmer Co., Ltd), measurement of light emission spectrum was performed by using Fluoromax-4 (manufactured by Horiba Jobin Yvon Inc.), measurement of excess attenuation curve was performed by using Quantaurus-tau (manufactured by Hamamatsu Photonics K.K.), and measurement of photoluminescence quantum efficiency (PL quantum efficiency) was performed by using Quantaurus-QY (manufactured by Hamamatsu Photonics In addition, in the present example, fluorescence having light emission life of 0.05 µs or more was determined as delayed fluorescence.

[1] Synthesis of Compound

In the present example, Compounds 1 to 6 were synthesized by the following reaction scheme.

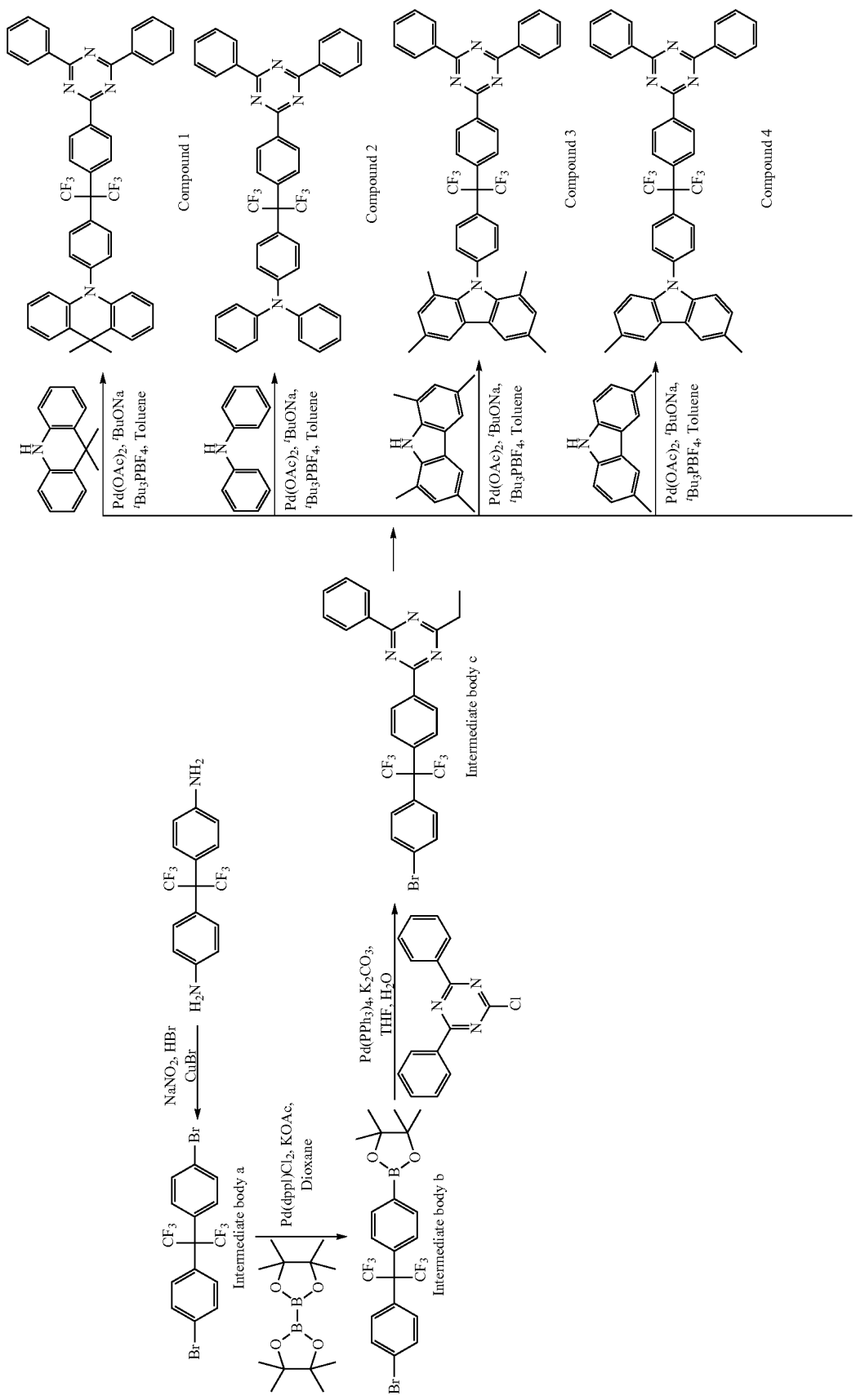

-continued
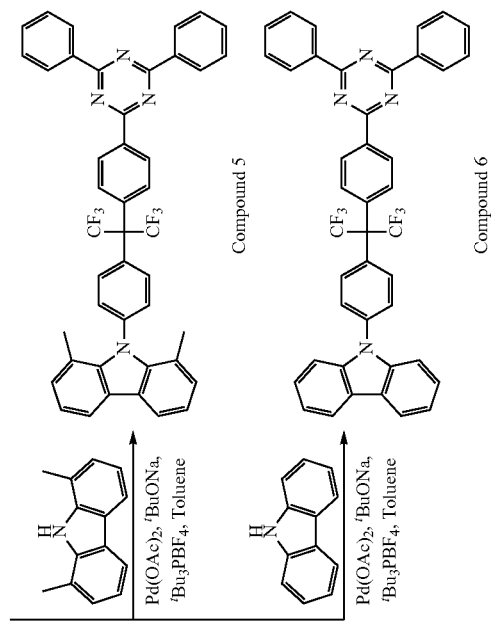

Specific synthesis procedure is shown below.

(Synthesis Example 1) Synthesis of Compound 1

First, Intermediate body a was synthesized by the following reaction.

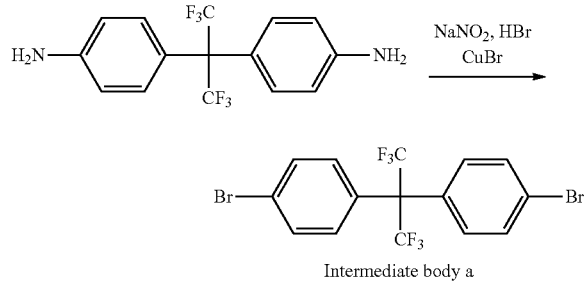

Intermediate body a 2,2-bis(4-aminophenyl)hexafluoropropane (3.34 g) and hydrobromic acid (20 mL) were put in a 10.0 mL of round bottom flask and left in an ice bath. A sodium nitrite aqueous solution (NaNO₂ 1.72 g/water 10 mL) was dropped in the mixture, and stirred to obtain a slurry. The slurry was stirred in an ice bath for 20 minutes, and then dropped in a hydrobromic acid solution of copper bromide (I) (CuBr 7.16 g/HBr 20 mL) while stirring, and further stirred at room temperature for 1.5 hours. 100 mL of water was added to the reaction solution, and generated precipitates were recovered by filtration to obtain a crude product. The crude product was purified by column chromatography using hexane as an eluant, and vacuum-dried to obtain a white solid of 2,2-bis(4-bromophenyl) hexafluoropropane (Intermediate body a) in a yield amount of 3.4 g at a yield rate of 73.6%.

Subsequently, Intermediate body b was synthesized by the following reaction.

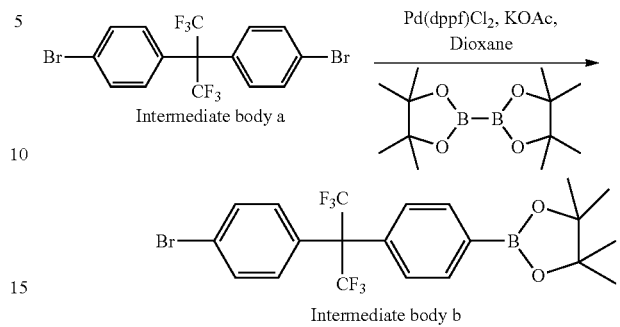

Intermediate body b 2,2-bis(4-bromophenyl) hexafluoropropane (2.31 g, 5 mmol), bis(pinacolato) diboron (1.27 g, 5 mmol), [1,1'-bis(diphenylphosphino) ferrocene] dichloroparadium (II) (110 mg, 0.15 mmol), potassium acetate (1.5 g), and 1,4-dioxane (50 mL) were put in a container, the inside of the container was substituted with nitrogen gas, and then heated in a hot water bath of 80° C. for 24 hours. The reaction solution was cooled to room temperature, and then 50 mL of water was added thereto to separate a water layer and an organic layer from each other. 50 mL of dicholoromethane was added to the water layer, and extraction was performed. In addition, the organic layer was recovered, 50 mL of dichloromethane was added to the remaining water layer, and an operation of performing extraction was repeated two times. Sodium sulfate was added to the recovered organic layer, dried, and filtered, and then the solvent was volatilized and removed. The obtained precipitates were purified by silica gel column chromatography by using a mixture solvent of dicholoromethane:hexane=1:2 in an eluant, and vacuum-dried to obtain a white solid of 2-(4-bromophenyl)-2-[4-{4,4,5,5-tetramethyl-1,3,2-dioxaborolane-2-yl)phenyl}hexafluoropropane (Intermediate body b) in a yield amount of 2.2 g at a yield rate of 86.4%.

Subsequently, Intermediate body c was synthesized by the following reaction.

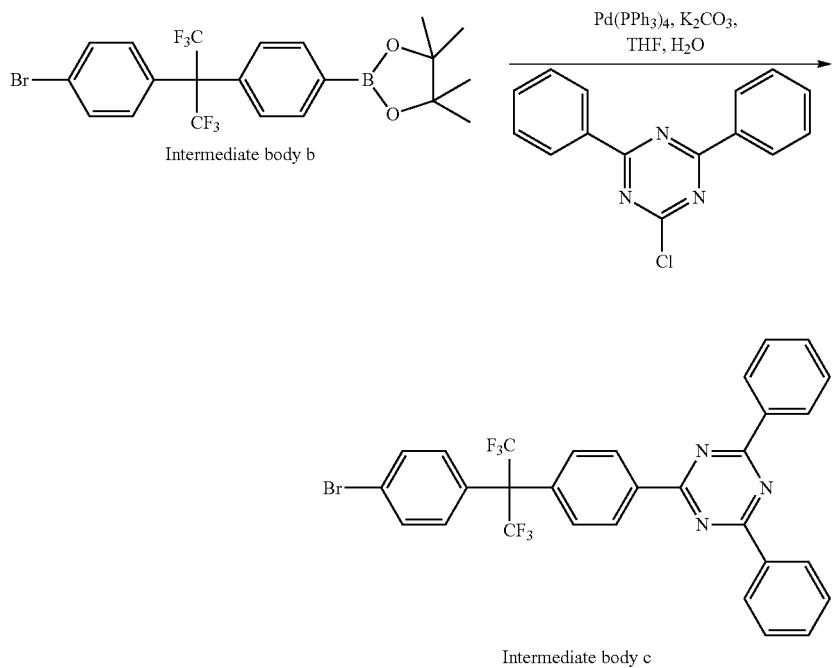

Intermediate body c 2-(4-bromophenyl)-2-{4-(4,4,5,5-tetramethyl)-1,3,2-dioxaborolane-2-yl]phenyl}-hexafluoropropane (2.04 g, 4 mmol), 2-chloro-4,6-diphenyl-1,3,5-triazine (1.29 g, 4.8 mmol), tetrakis(triphenylphosphine) palladium (0) (234 mg, 0.2 mmol), tetrahydrofuran (50 mL), and a potassium carbonate aqueous solution (1 M, 20 mL) were put in a container, the inside of the container was substituted with nitrogen gas, and then heated in a hot water bath of 60° C. for 16 hours. The reaction solution was cooled to room temperature to separate a water layer and an organic layer from each other. 50 mL of dichloromethane was added to the water layer and extraction was performed. In addition, the organic layer was recovered, 50 mL of dichloromethane was added to the remaining water layer, and an operation of performing extraction was repeated two times. Sodium sulfate was added to the recovered organic layer, dried, and filtered, and then the solvent was volatilized and removed. The obtained precipitates were purified by silica gel column chromatography by using a mixture solvent of dichloromethane:hexane=1:10 in an eluant, and vacuum-dried to obtain a white solid of 2-[4-{2-(4-bromophenyl)-1,1,1,3,3,3-hexafluoropropane-2-yl}phenyl]4,6-diphenyl-1,3,5-triazine (Intermediate body c) in a yield amount of 1.8 g at a yield rate of 73.2%.

Subsequently, Compound 1 was synthesized by the following reaction.

ladium acetate (II) (34 mg, 0.15 mmol), sodium tert-botoxide (1.73 g, 18 mmol), tri-tert-butylphosphonium tetrafluoroborate (131 mg, 0.45 mmol), and tolune (30 mL) were put in a container, and stirred at 110° C. for 16 hours in a nitrogen atmosphere. The reaction solution was cooled to room temperature, and then 50 mL of water was added thereto to separate a water layer and an organic layer from each other. 50 mL of dichloromethane was added to the water layer and extraction was performed. In addition, the organic layer was recovered, 50 mL of dichloromethane was added to the remaining water layer, and an operation of performing extraction was repeated two times. Sodium sulfate was added to the recovered organic layer, dried, and filtered, and the solvent was volatilized and removed. The obtained precipitates were purified by silica gel column chromatography by using a mixture solvent of dichloromethane:hexane=1:3 in an eluant, and vacuum-dried to obtain a white solid of Compound 1 in a yield amount of 1.72 g at a yield rate of 77.2%.

$^1$H-NMR (500 MHz, CDCl$_3$) δ=8.84 (d, J=8.8 Hz, 2H), 8.82-8.74 (m, 4H), 7.72 (dd, J=13.2, 8.5 Hz, 4H), 7.67-7.55 (m, 6H), 7.48 (dd, J=7.7, 1.5 Hz, 2H), 7.44-7.38 (m, 2H), 7.09-7.01 (m, 2H), 6.97 (td, J=7.5, 1.2 Hz, 2H), 6.30 (dd, J=8.2, 1.0 Hz, 2H), 1.69 (s, 6H); $^{13}$C-NMR (126 MHz, CDCl$_3$) δ=172.1, 171.0, 142.4, 140.7, 137.4, 136.2, 133.3, 132.9, 131.4, 130.7, 130.5, 129.2, 129.0, 128.9, 126.6, 125.4, 121.1, 114.1, 36.2, 31.2; APCI-MS m/z: 742 M$^+$; Anal. calcd for C$_{45}$H$_{32}$F$_6$N$_4$: C, 72.77; H, 4.34; N, 7.54. Found: C, 72.70; H, 4.32; N, 7.59.

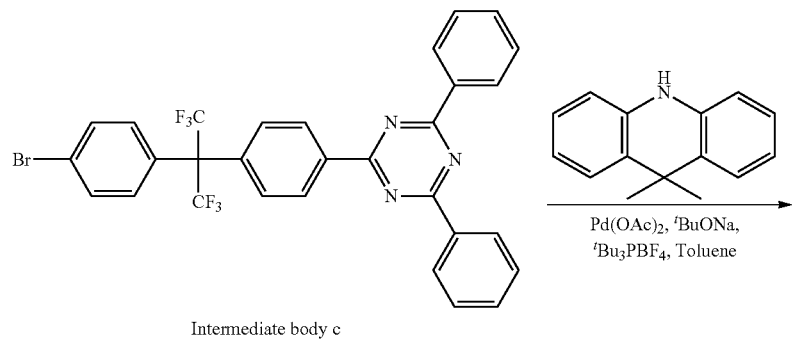

Intermediate body c

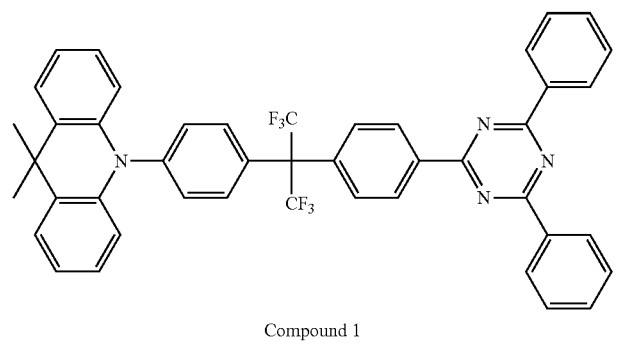

Compound 1

2-[4-{2-(4-bromophenyl)-1,1,1,3,3,3-hexafluoropropane-2-yl}phenyl]-4,6-diphenyl-1,3,5-triazine (1.85 g, 3 mmol), 9,9-dimethyl-9,10-dihydroacridine (753 mg, 3.6 mmol), pal- (Synthesis Example 2) Synthesis of Compound 2

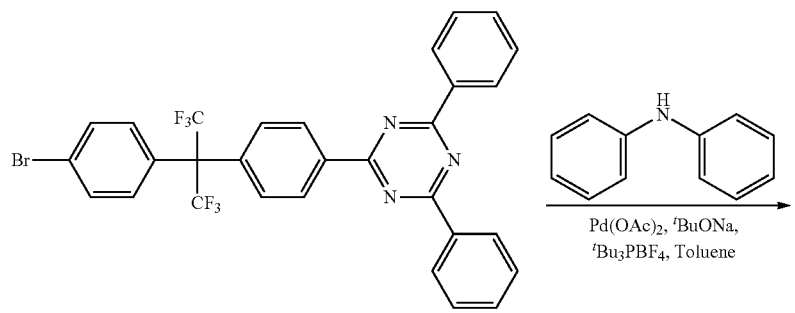

Intermediate body c

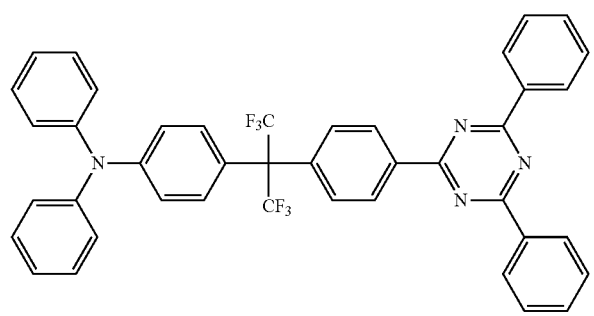

Compound 2

2-[4-{2-(4-bromophenyl)-1,1,1,3,3,3-hexafluoropropane-2-yl}phenyl]-4,6-diphenyl-1,3,5-triazine (1.85 g, 3 mmol), diphenylamine (609 mg, 3.6 mmol), palladium acetate (II) (34 mg, 0.15 mmol), sodium tert-butoxide (1.73 g, 18 mmol), tri-tert-butylphosphonium tetrafluoroborate (131 mg, 0.45 mmol), and toluene (30 mL) were put in a container, and stirred at 110° C. for 16 hours in a nitrogen atmosphere. The reaction solution was cooled to room temperature, and then 50 mL of water was added thereto to separate a water layer and an organic layer from each other. 50 mL of dichloromethane was added to the water layer and extraction was performed. In addition, the organic layer was recovered, dichloromethane was added to the remaining water layer, and an operation of performing extraction was repeated two times. Sodium sulfate was added to the recovered organic layer, dried, and filtered, the solvent was volatilized and removed. The obtained precipitates were purified by silica gel column chromatography by using the mixture solution of dichloromethane:hexane=1:3 in an eluant, and vacuum-dried to obtain a white solid of Compound 2 in a yield amount of 1.65 g at a yield rate of 78.3%.

$^1$H-NMR (500 MHz, CDCl$_3$) δ=8.83-8.74 (m, 6H), 7.68. (d, J=8.4 Hz, 2H), 7.65-7.56 (m, 6H), 7.30 (dd, J=8.4, 7.4 Hz, 4H), 7.22 (d, J=8.7 Hz, 2H), 7.16 (dd, J=8.4, 7.4 Hz, 4H), 7.11-7.05 (m, 2H), 7.03-6.97 (m, 2H); $^{13}$C-NMR (126 MHz, CDCl$_3$) δ=172.0, 171.1, 148.5, 147.1, 137.9, 137.0, 136.2, 132.8, 131.0, 130.7, 129.6, 129.2, 128.9, 128.8, 125.6, 125.4, 124.1, 120.9; APCI-MS m/z: 702 M$^+$; Anal. calcd for C$_{42}$H$_{28}$F$_6$N$_4$: C, 71.79; H, 4.02; N, 7.97. Found: C, 71.65; H, 3.90; N, 8.00.

(Synthesis Example 3) Synthesis of Compound 3

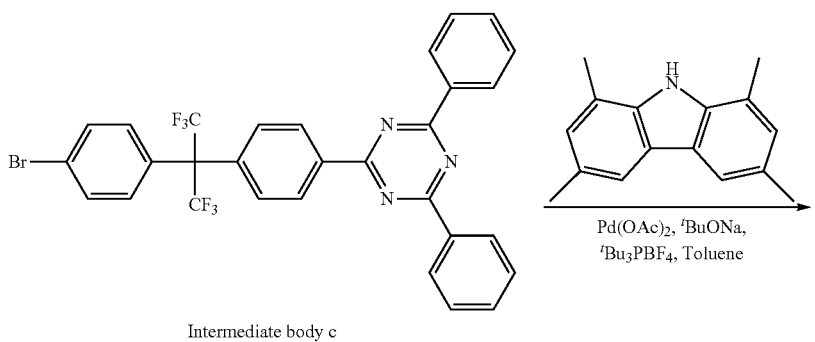

Intermediate body c

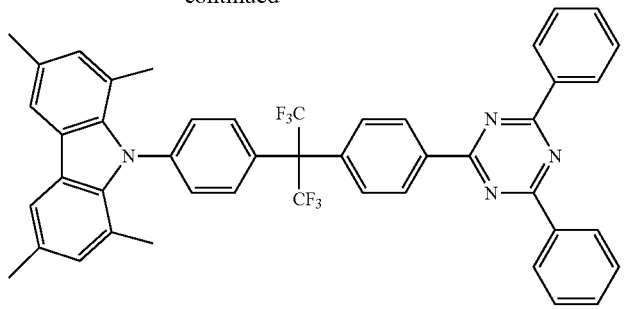

Compound 3

2-[4-{2-(4-bromophenyl)-1,1,1,3,3,3-hexafluoropropane-2-yl}phenyl]-4,6-diphenyl-1,3,5-triazine (1.85 g, 3 mmol), 1,3,6,8-tetramethyl-9H-carbazole (804 mg, 3.6 mmol), palladium acetate (II) (34 mg, 0.15 mmol), sodium tert-butoxide (1.73 g, 18 mmol), tri-tert-butylphosphonium tetrafluoroborate (131 mg, 0.45 mmol), and toluene (30 mL) were put in a container, and stirred at 110° C. for 16 hours in a nitrogen atmosphere. The reaction solution was cooled to room temperature, and then 50 mL of water was added thereto to separate a water layer and an organic layer from each other. 50 mL of dichloromethane was added to the water layer and extraction was performed. In addition, the organic layer was recovered, dichloromethane was added to the remaining water layer, and an operation of performing extraction was repeated two times. Sodium sulfate was added to the recovered organic layer, dried, and filtered, and the solvent was volatilized and removed. The obtained precipitates were purified by silica gel column chromatography by using a mixture solvent of dichloromethane: hexane=1:3 in an eluant, and vacuum-dried to obtain a white solid of Compound 3 in a yield amount of 1.86 g and at a yield rate of 81.9%.

$^1$H-NMR (500 MHz, CDCl$_3$) δ=8.81 (dd, J=7.3, 5.2 Hz, 2H), 8.80-8.76 (m, 4H), 7.73 (d, J=10.6 Hz, 2H), 7.70-7.65 (m, 2H), 7.65-7.56 (m, 6H), 7.53 (s, 4H), 6.94 (s, 2H), 2.48 (s, 6H), 1.94 (s, 6H); $^{13}$C-NMR (126 MHz, CDCl$_3$) δ=172.1, 170.9, 143.7, 139.6, 137.4, 137.3, 136.1, 133.9, 132.9, 131.3, 130.6, 130.5, 130.4, 129.5, 129.2, 129.0, 128.9, 124.5, 121.2, 11.8.0, 21.3, 19.5; APCI-MS m/z: 756 M$^+$; Anal. calcd for C$_{46}$H$_{34}$F$_6$N$_4$: C, 73.01; H, 4.53; N, 7.40. Found: C, 72.97; H, 4.47; N, 7.41.

(Synthesis Example 4) Synthesis of Compound 4

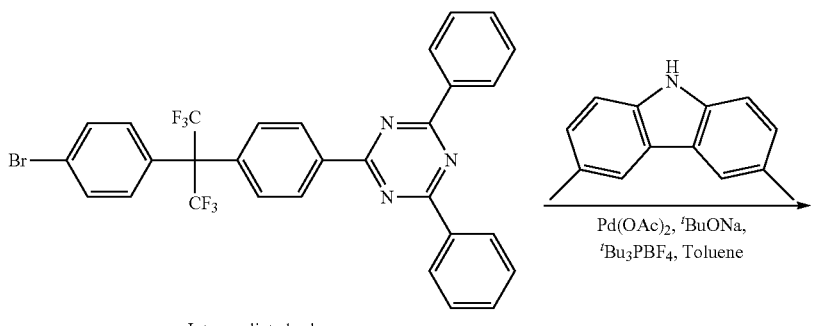

Intermediate body c

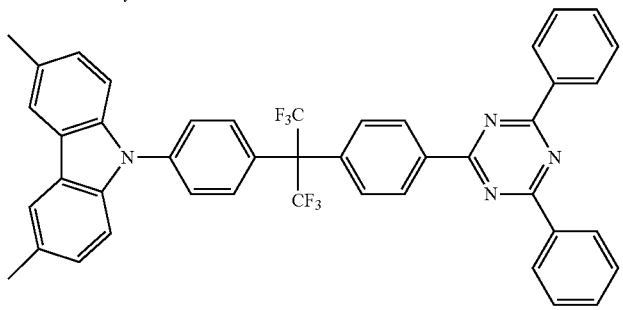

Compound 4

2-[4-{2-(4-bromophenyl)-1,1,1,3,3,3-hesafluoropropane-2-yl}, phenyl]-4,6-diphenyl-1,3,5-triazine (1.85 g, 3 mmol), 3,6-dimethyl-9H-carbazole (703 mg, 3.6 mmol), palladium acetate (II) (34 mg, 0.15 mmol), sodium tert-butoxide (1.73 g, 18 mmol), tri-tert-butylphosphonium tetrafluoroborate (131 mg, 0.45 mmol), and toluene (30 mL) were put in a container, and stirred at 110° C. for 16 hours in a nitrogen atmosphere. The reaction solution was cooled to a room temperature, and then 50 mL of water was added thereto to separate a water layer and an organic layer. 50 mL of dichloromethane was added to the water layer and extraction was performed. In addition, the organic layer was recovered, dichloromethane was added to the remaining water layer, and an operation of performing extraction was repeated two times. Sodium sulfate was added to the recovered organic layer, dried, and filtered, and the solvent was volatilized and removed. The obtained precipitates were purified by silica gel column chromatography by using a mixture solvent of dichloromethane:hexane=1:3 in an eluant, and vacuum-dried to obtain a white solid of Compound 4 in a yield amount of 1.62 g at a yield rate of 74.1%.

$^1$H-NMR (500 MHz, CDCl$_3$) δ=8.84 (d, J=8.7 Hz, 2H), 8.81-8.73 (m, 4H), 7.90 (s, 2H), 7.74 (d, J=8.4 Hz, 2H), 7.62 (ddd, J=21.7, 10.8, 6.0 Hz, 10H), 7.41 (d, J=8.3 Hz, 2H), 7.24 (dd, J=8.4, 1.4 Hz, 2H), 2.55 (s, 6H); $^{13}$C-NMR (126 MHz, CDCl$_3$) δ=172.0, 171.0, 139.3, 138.9, 137.5, 137.3, 136.2, 132.9, 131.9, 131.5, 130.7, 129.8, 129.2, 129.0, 128.9, 127.4, 126.2, 126.1, 123.9, 120.5, 109.6, 21.5; APCI-MS m/z: 728 M$^+$; Anal. calcd for C$_{44}$H$_{30}$F$_6$N$_4$: C, 72.52; H, 4.15; N, 7.59. Found: C, 72.28; H, 4.13; N, 7.26.

(Synthesis 5) Synthesis of Compound 5 g, 18 mmol), tri-tert-butylphosphonium tetrafluoroborate (131 mg, 0.45 mmol), and toluene (30 mL) were put in a container, and stirred at 110° C. for 16 hours in a nitrogen atmosphere. The reaction solution was cooled to a room temperature, and then 50 mL of water was added thereto to separate a water layer and an organic layer from each other. 50 mL of dichloromethane was added to the water layer and extraction was performed. In addition, the organic layer was recovered, dichloromethane was added to the remaining water layer, and an operation of performing extraction was repeated two times. Sodium sulfate was added to the recovered organic layer, dried, and filtered, and the solvent was volatilized and removed. The obtained precipitates were purified by silica gel column chromatography by using a mixture solvent of dichloromethane:hexane=1:3 in an eluant, and vacuum-dried to obtain a white solid of Compound 5 in a yield amount of 0.1.52 g at a yield rate of 69.5%.

$^1$H-NMR (500 MHz, CDCl$_3$) δ=8.83 (d, J=8.8 Hz, 2H), 8.81-8.76 (m, 4H), 8.00 (d, J=7.1 Hz, 2H), 7.68 (d, J=8.4 Hz, 2H), 7.66-7.54 (m, 10H), 7.18 (t, J=7.4 Hz, 2H), 7.13 (d, J=7.0 Hz, 2H), 1.99 (s, 6H); $^{13}$C-NMR (126 MHz, CDCl$_3$)

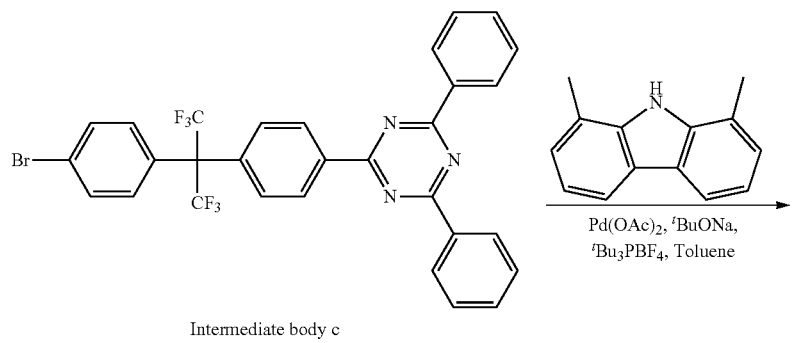

Intermediate body c

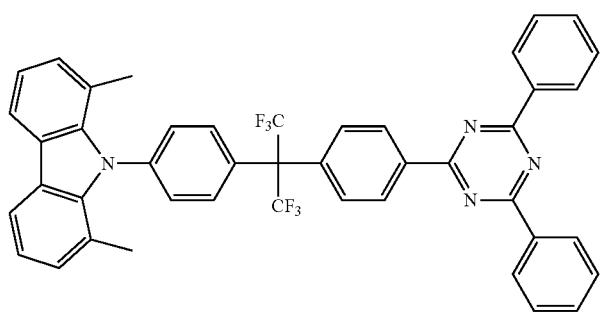

Compound 5

2-[4-{2-(4-bromophenyl)-1,1,1,3,3,3-hexafluoropropane-2-yl}, phenyl]-4,6-diphenyl-1,3,5-triazine (1.85 g, 3 mmol), 1,8-dimethyl-9H-carbazole (703 mg, 3.6 mmol), palladium acetate (II) (34 mg, 0.15 mmol), sodium tert-butoxide (1.73

δ=4.2, 132.9, 131.5, 13.0.6, 130.4, 129.3, 129.2, 129.0, 128.9, 124.3, 121.5, 120.3, 118.3, 19.6; APCI-MS m/z: 728 M$^+$; Anal. calcd for C$_{44}$H$_{30}$F$_6$N$_4$: C, 72.52; H, 4.15; N, 7.69. Found: C, 72.2.9; H, 4.12; N, 7.56.

(Synthesis 6). Synthesis of Compound 6

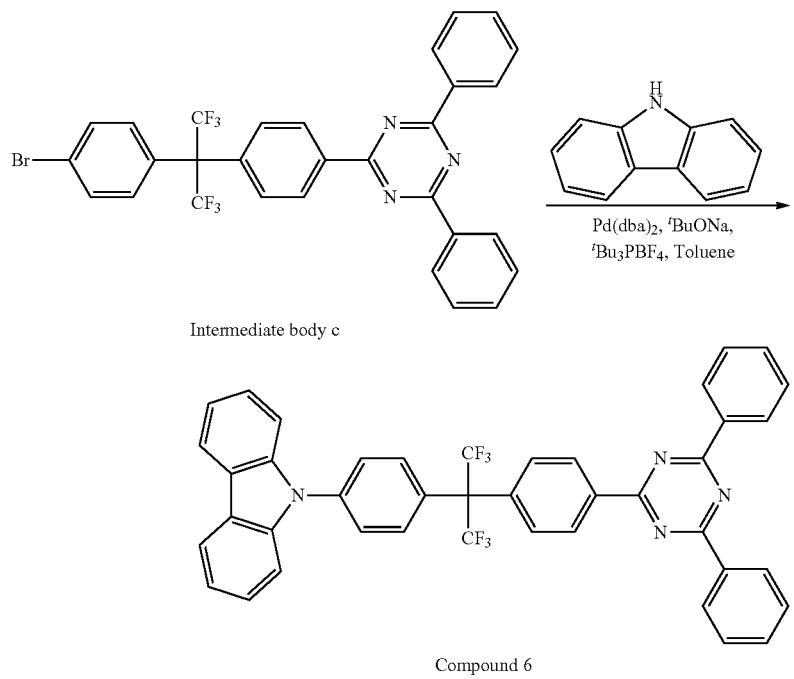

Compound 6

2-[4-{2-(4-bromophenyl)-1,1,1,3,3,3-hexafluoropropane-2-yl}, phenyl]-4,6-diphenyl-1,3,5-triazine (1.85 g, 3 mmol), carbazole (602 mg, 3.6 mmol), bis(dibenzilidene acetone) palladium (0) (86 mg, 0.15 mmol), sodium tert-butoxide (1.73 g, 18 mmol), tri-tert-butylphosphonium tetrafluoroborate (131 mg, 0.45 mmol), and toluene (30 mL) were put in, a container, and stirred at 110° C. for 16 hours in a nitrogen atmosphere. The reaction solution was cooled to a room temperature, and then 50 mL of water was added thereto to separate a water layer and an organic layer from each other. 50 mL of dichloromethane was added to the water layer, and extraction was performed. In addition, the organic layer was recovered, dichloromethane was added to the remaining water layer, and an operation of performing extraction was repeated two times. Sodium sulfate was added to the recovered organic layer, dried, and filtered, and the solvent was volatilized and removed. The obtained precipitates were purified by silica gel column chromatography by using a mixture solvent of dichloromethane:hexane=1:3 in an eluant, and vacuum-dried to obtain a white solid of Compound 6 in a yield amount of 1.52 g at a yield rate of 72.4%.

$^1$H-NMR (500 MHz, CDCl$_3$) δ=8.85 (d, J=8.8 Hz, 2H), 8.81-8.74 (m, 4H), 8.16 (d, J=7.7 Hz, 2H), 7.74 (d, J=8.2 Hz, 2H), 7.71-7.55 (m, 10H), 7.53 (t, J=8.2 Hz, 2H), 7.49-7.42 (m, 2H), 7.33 (t, J=7.4 Hz, 2H); $^{13}$C-NMR (126 MHz, CDCl$_3$) δ=172.0, 171.0, 140.6, 138.9, 137.4, 137.3, 136.1, 132.9, 132.1, 132.0, 130.7, 129.2, 129.0, 128.9, 126.6, 126.3, 123.8, 120.6, 109.9; APCI-MS m/z: 700 M$^+$; Anal. calcd for C$_{42}$H$_{26}$F$_6$N$_4$: C, 72.00; H, 3.74; N, 8.00. Found: C, 71.89; H, 3.72; N, 7.86.

[2] Preparation and Evaluation of Organic Light-Emitting Element (Example 1) Preparation and Evaluation of Organic Photoluminescence Element Using Compound 1

Compound 1 in a globe box in an Ar atmosphere was dissolved in toluene, chloroform, or cyclohexane to prepare a solution. A concentration of Compound 1 in each solution was 2×10$^{-5}$ mol/L.

In addition, a thin film (single film) of Compound 1 under a condition of degree of vacuum of 5×10$^{-4}$ Pa or less was formed at a thickness of 50 nm on a quartz substrate by a vacuum deposition method to make an organic photoluminescence element.

Apart from this, Compound 1 and PPT under a condition of degree of vacuum of 5×10$^{-4}$ Pa or less was deposited from different deposition sources on a quartz substrate by a vacuum deposition method, and a thin film (dope film) of Compound 1 having a concentration of 10% by mass was formed at a thickness of 50 nm to make an organic electroluminescence element.

Figure 2:
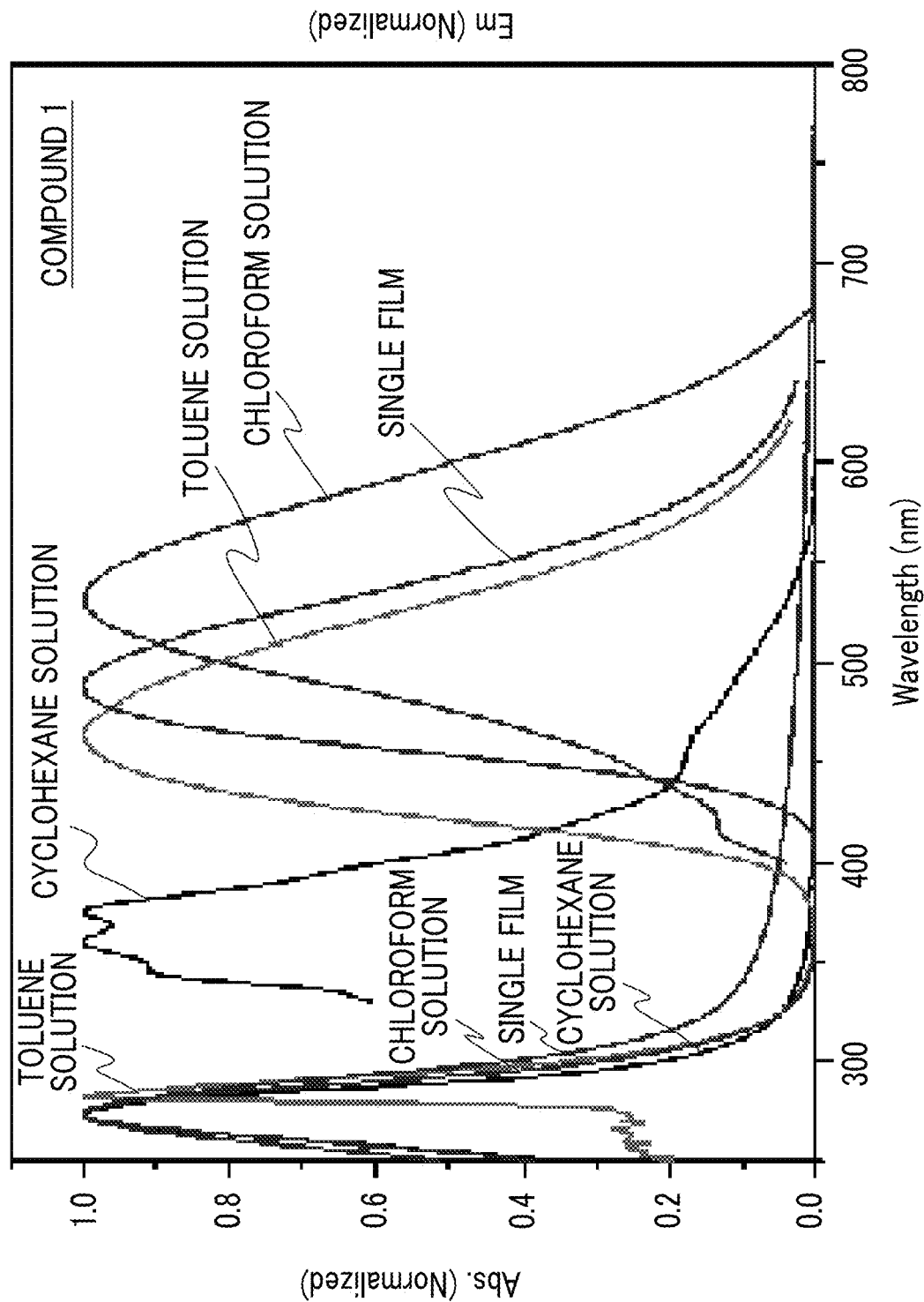
FIG. 2 illustrates light emission spectrums and absorption spectrums of a toluene solution, a chloroform solution, a cyclohexane solution, and a single film of a compound 1.
Figure 3:
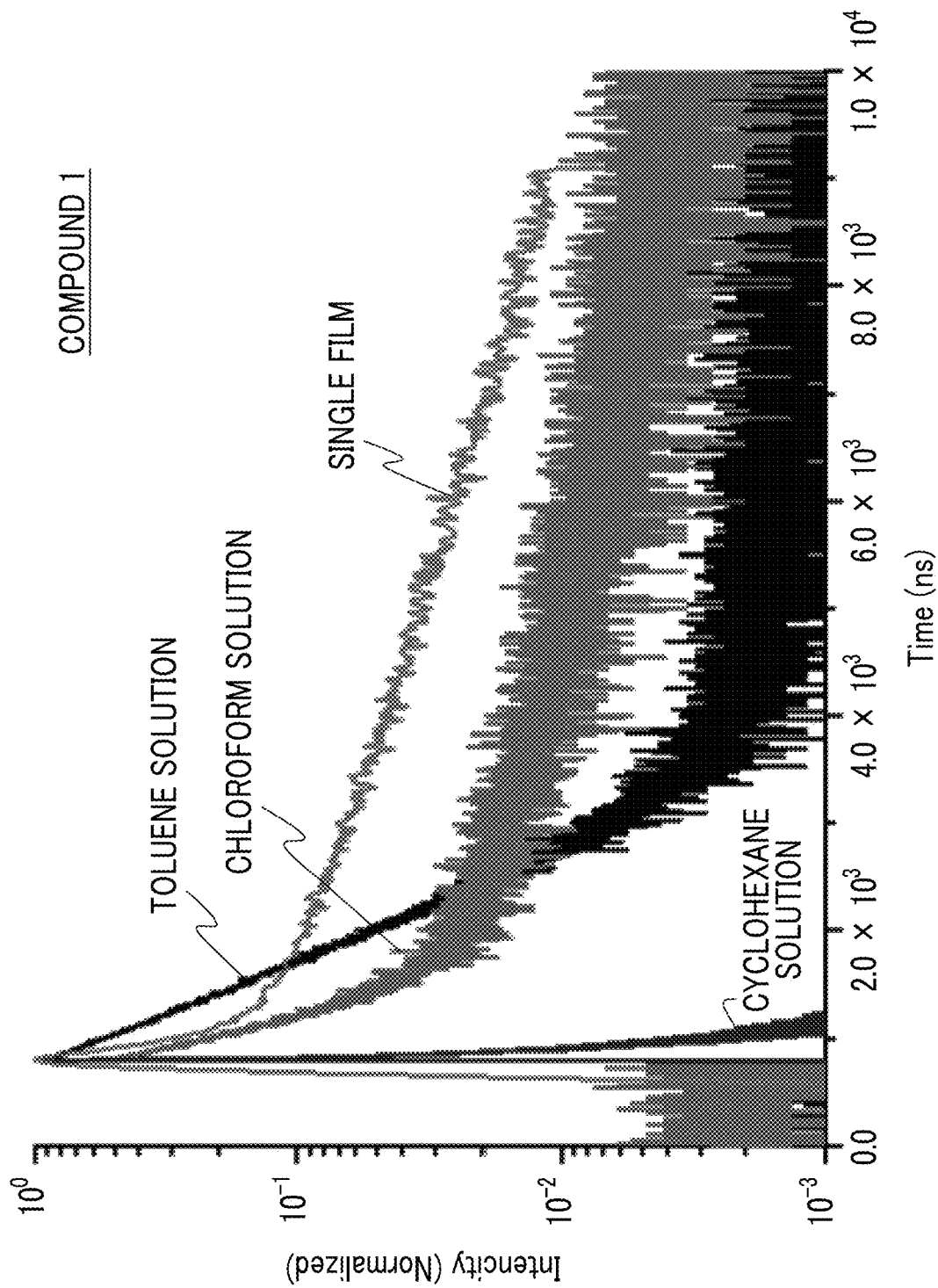
FIG. 3 illustrates excess attenuation curves of light emission of the toluene solution, the chloroform solution, the cyclohexane solution, and the single film of the compound 1.

Regarding each solution and the single film of Compound 1, light emission spectrum and absorption spectrum measured using 340 nm of excitation light are shown in FIG. 2, and excess attenuation curve of light emission measured by using 340 nm of excitation light is shown in FIG. 3. In the two spectrums of each solution and the single film shown, in FIG. 2, the spectrum having, a maximum on a short wavelength, side is the absorption spectrum, and the spectrum having a maximum on a long wavelength side is the light emission spectrum. The same applies to FIGS. 4, 6, 8, 10, and 12 as below. In addition, a photoluminescence quantum efficiency (PL quantum efficiency) measured with respect to each solution, the single film, and the dope film of Compound 1, and a photoluminescence quantum efficiency (PL quantum efficiency) measured after degassing of each solution, the single film, and the dope film of Compound 1 are shown in Table 1.

(Examples 2 to 4) Preparation and Evaluation of Organic Photoluminescence Element Using Compounds 2 to 4

In the same manner as that of Example 1 except that Compounds 2 to 4 were used instead of Compound 1, toluene solutions, chloroform solutions, cyclohexane solutions, single films, and dope films of Compounds 2 to 4 were prepared.

Figure 4:
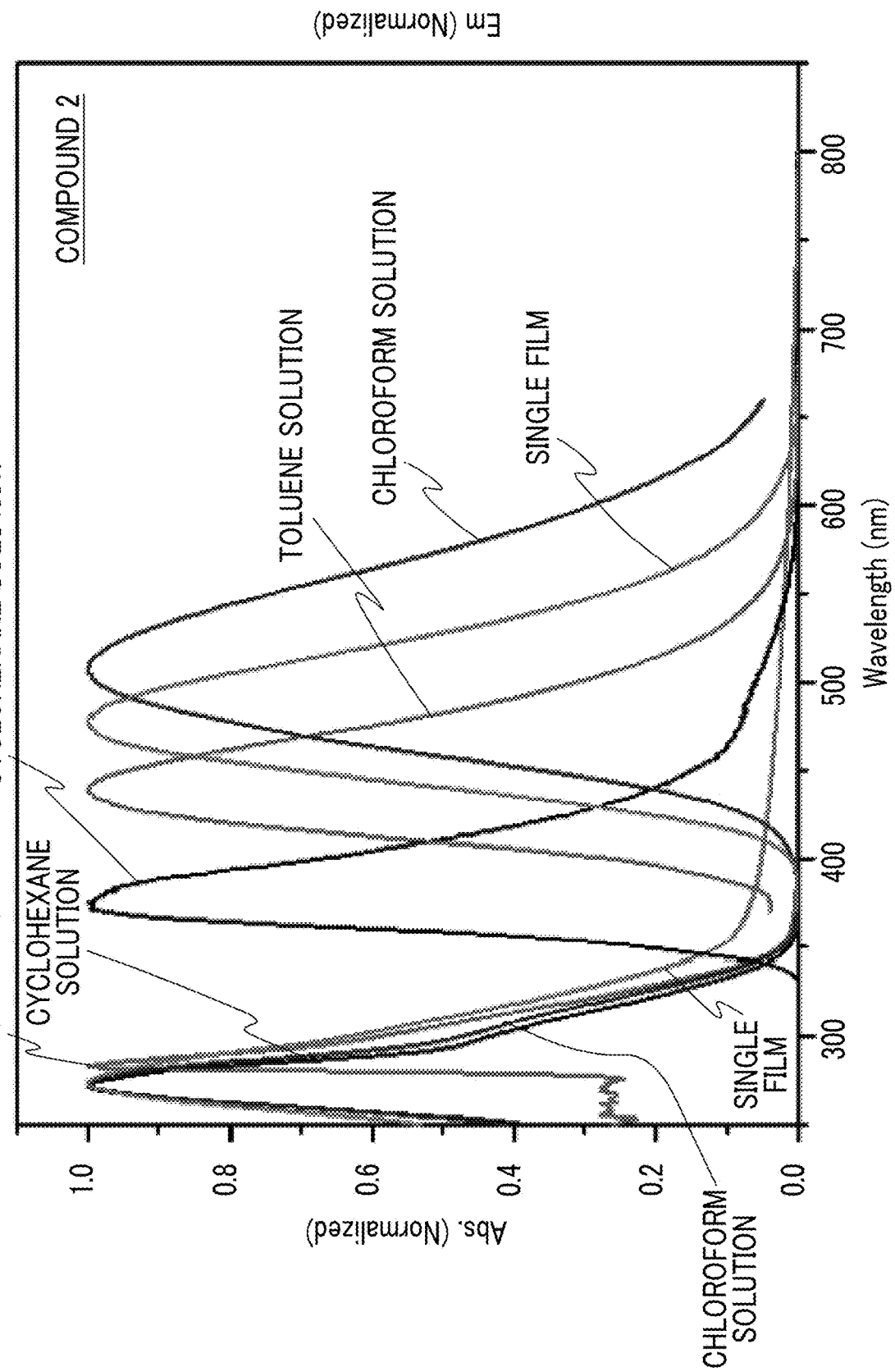
FIG. 4 illustrates light emission spectrums and absorption spectrums of a toluene solution, a chloroform solution, a cyclohexane solution, and a single film of a compound 2.
Figure 5:
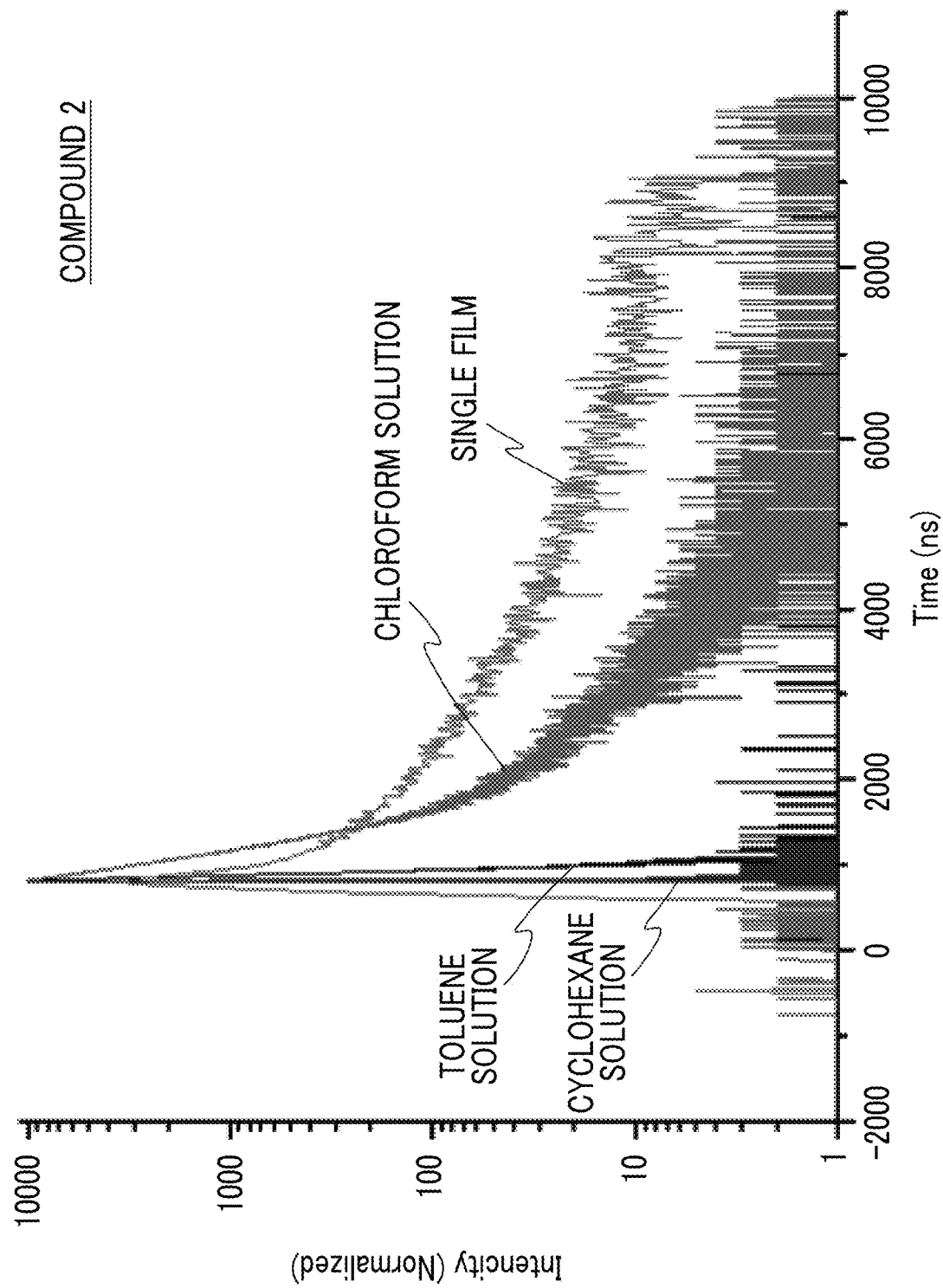
FIG. 5 illustrates excess attenuation curves of light emission of the toluene solution, the chloroform solution, the cyclohexane solution, and the single film of the compound 2.

Regarding each solution and a single film of Compound 2, light emission spectrum and absorption spectrum measured using 340 nm of excitation light are shown in FIG. 4, and excess attenuation curve of light emission using 340 nm of excitation light is shown in FIG. 5. Photoluminescence quantum efficiency measured with respect to each solution, the single filth, and the dope film of Compound 2 and photoluminescence quantum efficiency measured after degassing of each solution, the single film, and the dope film of Compound 2 are shown in Table 2.

Figure 6:
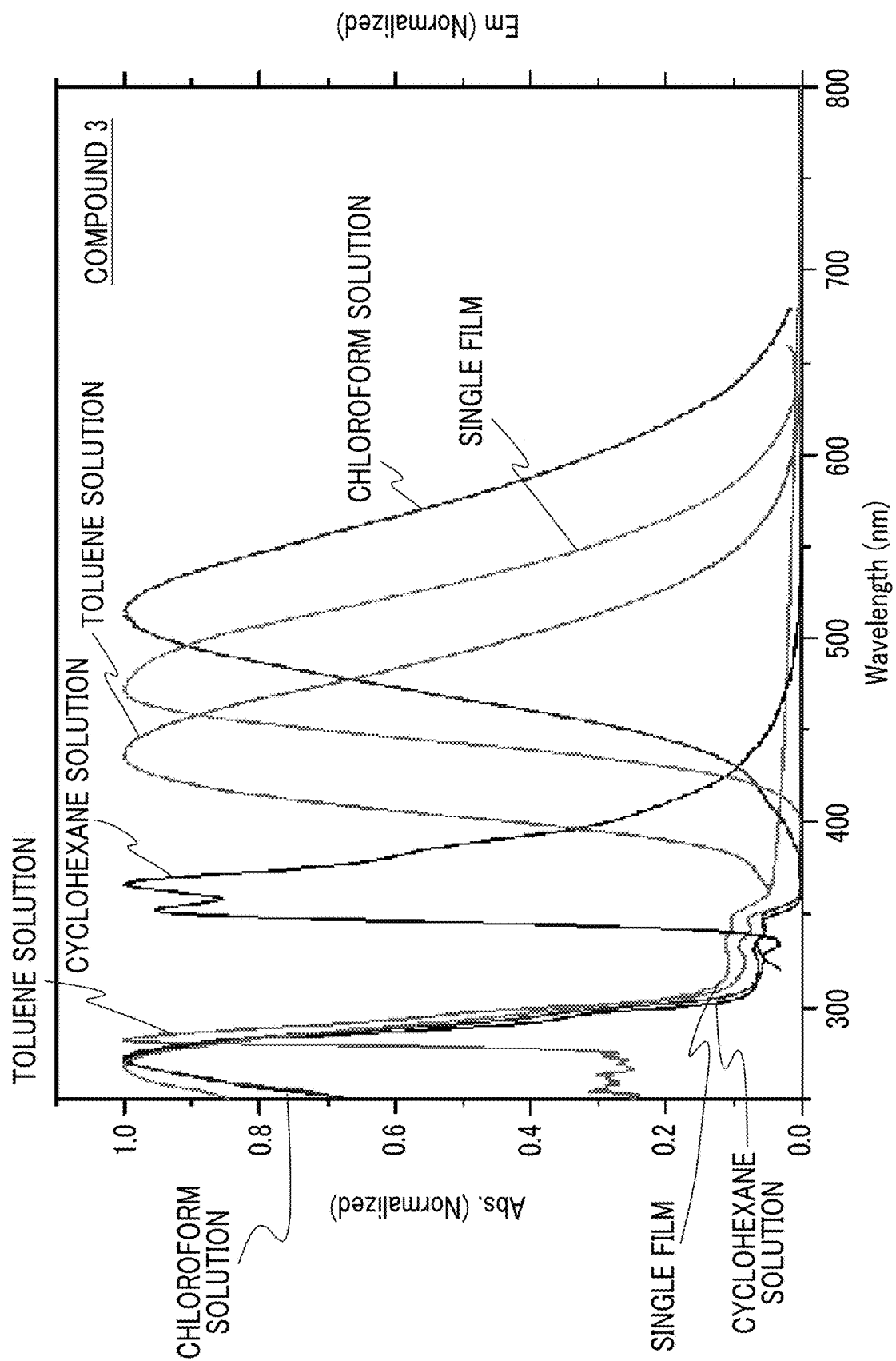
FIG. 6 illustrates light emission spectrums and absorption spectrums of a toluene solution, a chloroform solution, a cyclohexane solution, and a single film of a compound 3.
Figure 7:
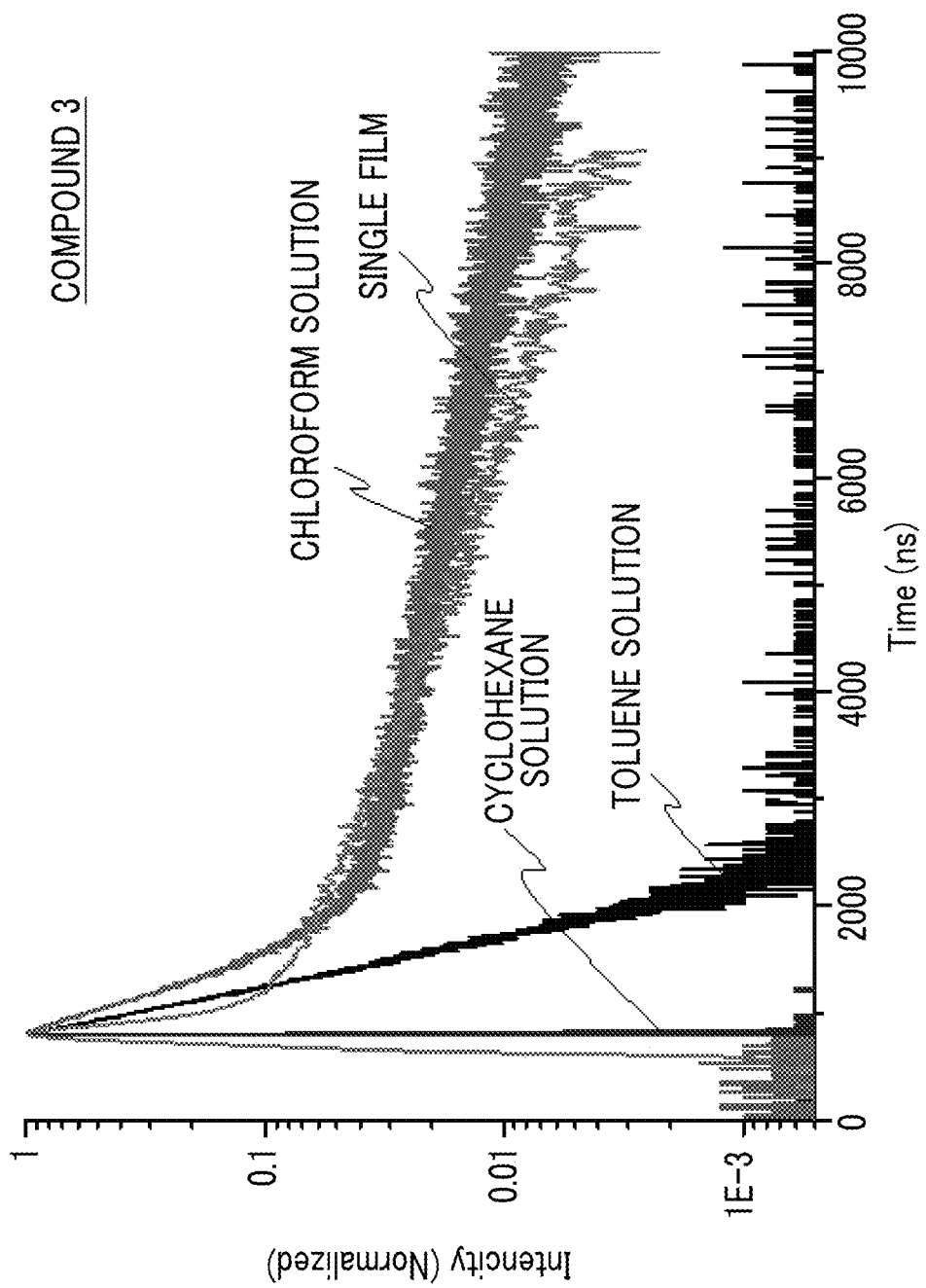
FIG. 7 illustrates excess attenuation curves of light emission of the toluene solution, the chloroform solution, the cyclohexane solution, and the single film of the compound 3.

Regarding each solution and a single film of Compound 3, light emission spectrum measured using 340 nm of excitation light is shown in FIG. 6, and excess attenuation curve of light emission measured using 340 nm of excitation light is shown in FIG. 7. Photoluminescence quantum efficiency measured with respect to each solution, the single film, and the dope film of Compound 3 and photoluminescence quantum efficiency measured after degassing of each solution, the single film, and the dope film of Compound 3 are shown in Table 3.

Figure 8:
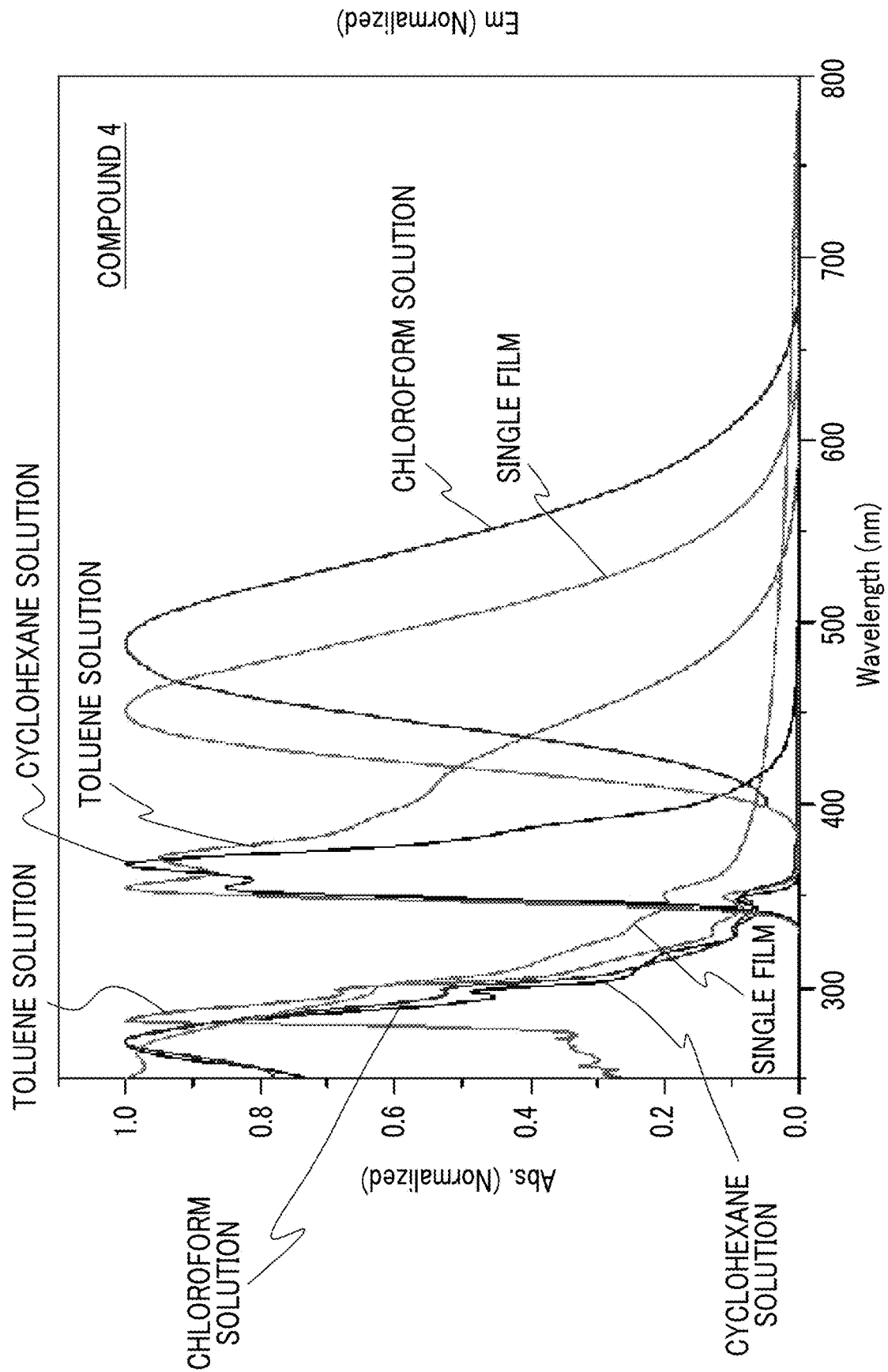
FIG. 8 illustrates light emission spectrums and absorption spectrums of a toluene solution, a chloroform solution, a cyclohexane solution, and a single film of a compound 4.
Figure 9:
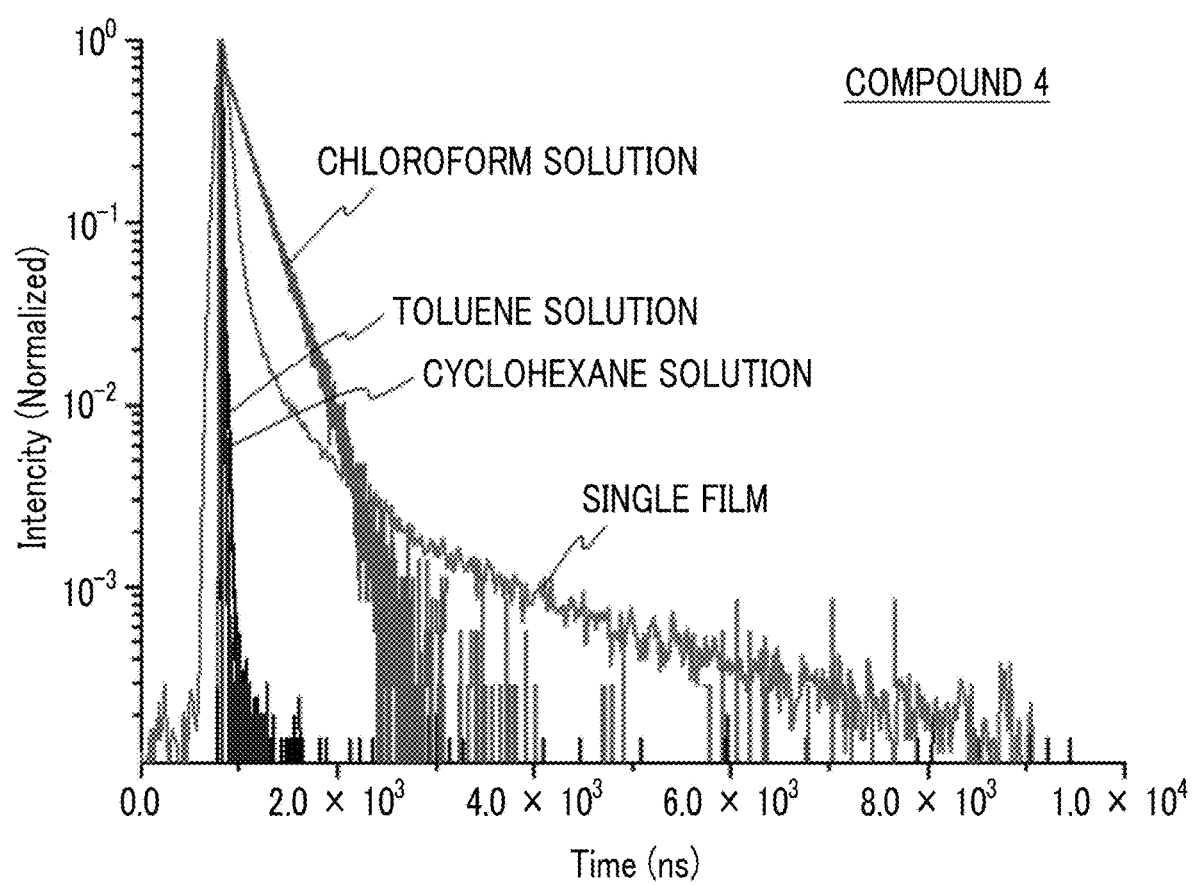
FIG. 9 illustrates excess attenuation curves, of light emission of the toluene solution, the chloroform solution, the cyclohexane solution, and the single film of the compound 4.

With respect to each solution and a single film of Compound 4, light emission spectrum and absorption spectrum measured by using 340 nm of excitation light are shown in FIG. 8, and excess attenuation curve of light emission measured by using 340 nm of excitation light is shown in FIG. 9. Photoluminescence quantum efficiency measured with respect to each solution, the single film, and the dope film of Compound 4 and photoluminescence quantum efficiency measured after degassing of each solution, the single film, and the dope film of Compound 4 are shown in Table 4.

(Example 5) Preparation and Evaluation of Organic Photoluminescence Element Using Compound 5

In the same manner as that of Example 1, except that Compound 5 was used instead, of Compound 1, a toluene solution, a chloroform solution, a single film, and a dope film of Compound 5 were prepared.

Figure 10:
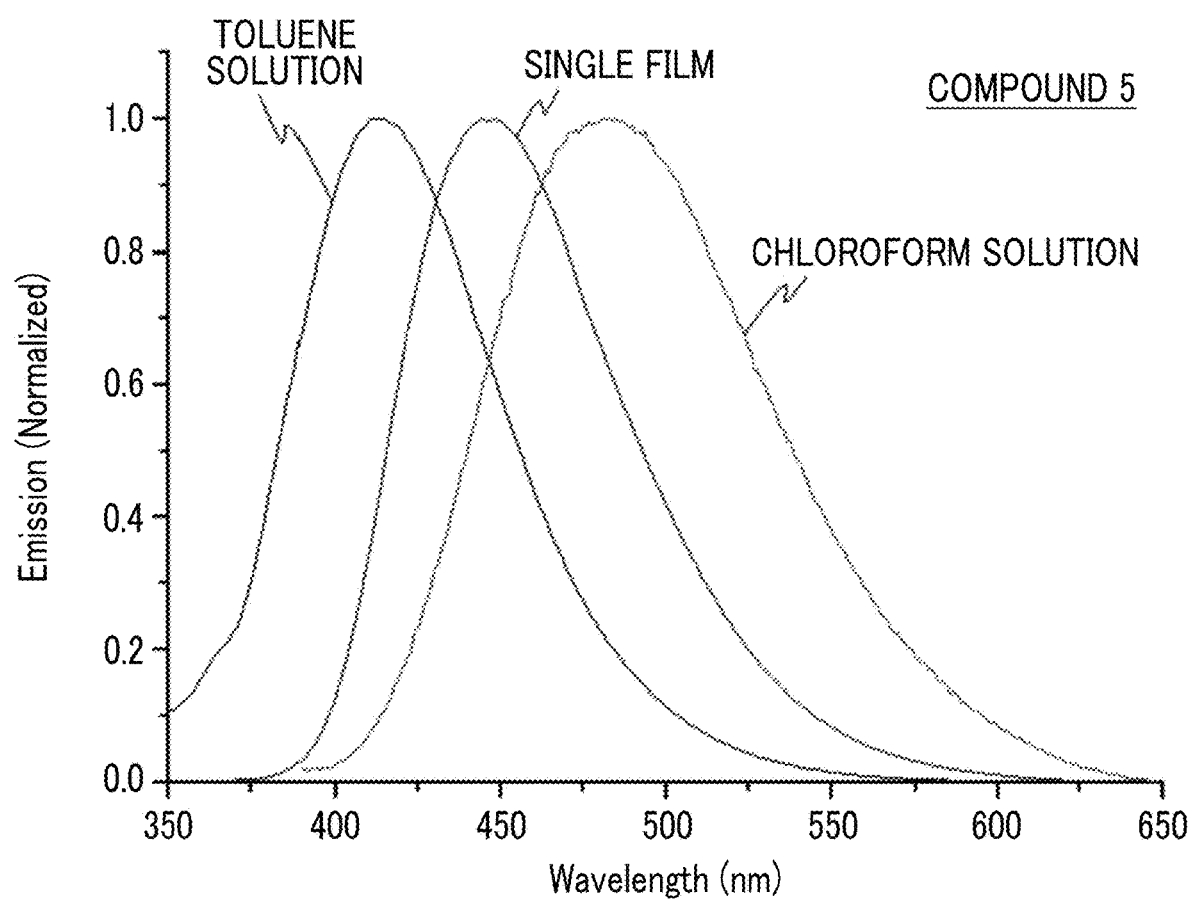
FIG. 10 illustrates light emission spectrums of a toluene solution, a chloroform solution, a cyclohexane solution, and a single film of a compound 5.
Figure 11:
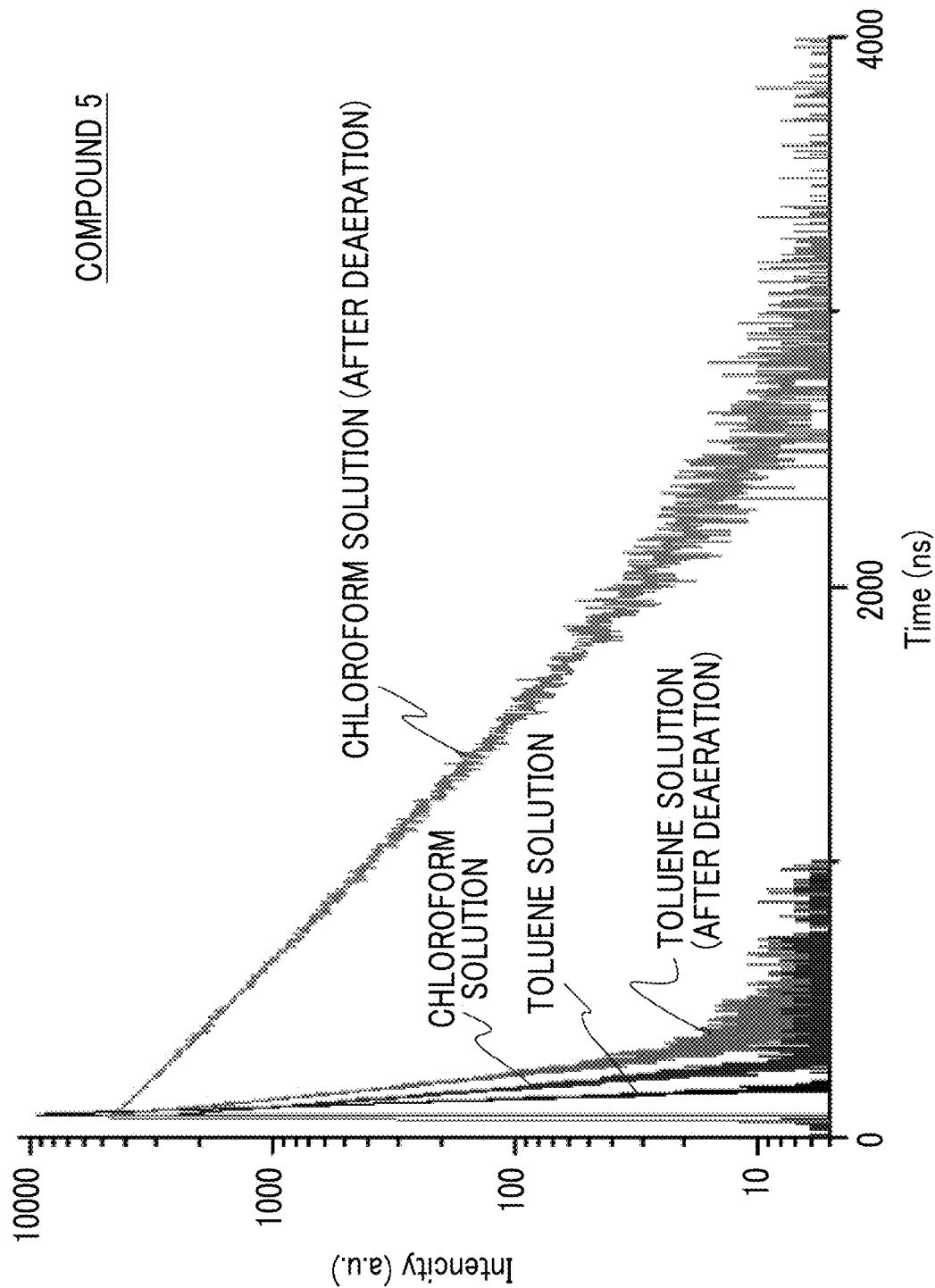
FIG. 11 illustrates excess attenuation curves of light emission of the toluene solution and the chloroform solution of the compound 5 and excess attenuation curves of light emission after degassing of the toluene solution and the chloroform solution of the compound 5.

With respect to each solution and the single film of Compound 5, light emission spectrum and absorption spectrum measured by using 340 nm of excitation light are shown in FIG. 10. With respect to the toluene solution and the chloroform solution of Compound 5, excess attenuation curve of light emission measured by using 340 nm of excitation light and excess attenuation curve of light emission measured after degassing of these solutions are shown in FIG. 11. Photoluminescence quantum efficiency measured with respect to each solution, the single film, and the dope film of Compound 5 and photoluminescence quantum efficiency measured after degassing of each solution, the single film, and the dope film of Compound 5 are shown in Table 5.

(Example 6) Preparation and Evaluation of Organic Photoluminescence Element Using Compound 6

In the same manner as that of Example 1, except that Compound 6 was used instead of Compound. 1, a toluene solution and a single film of Compound 6 were prepared.

Figure 12:
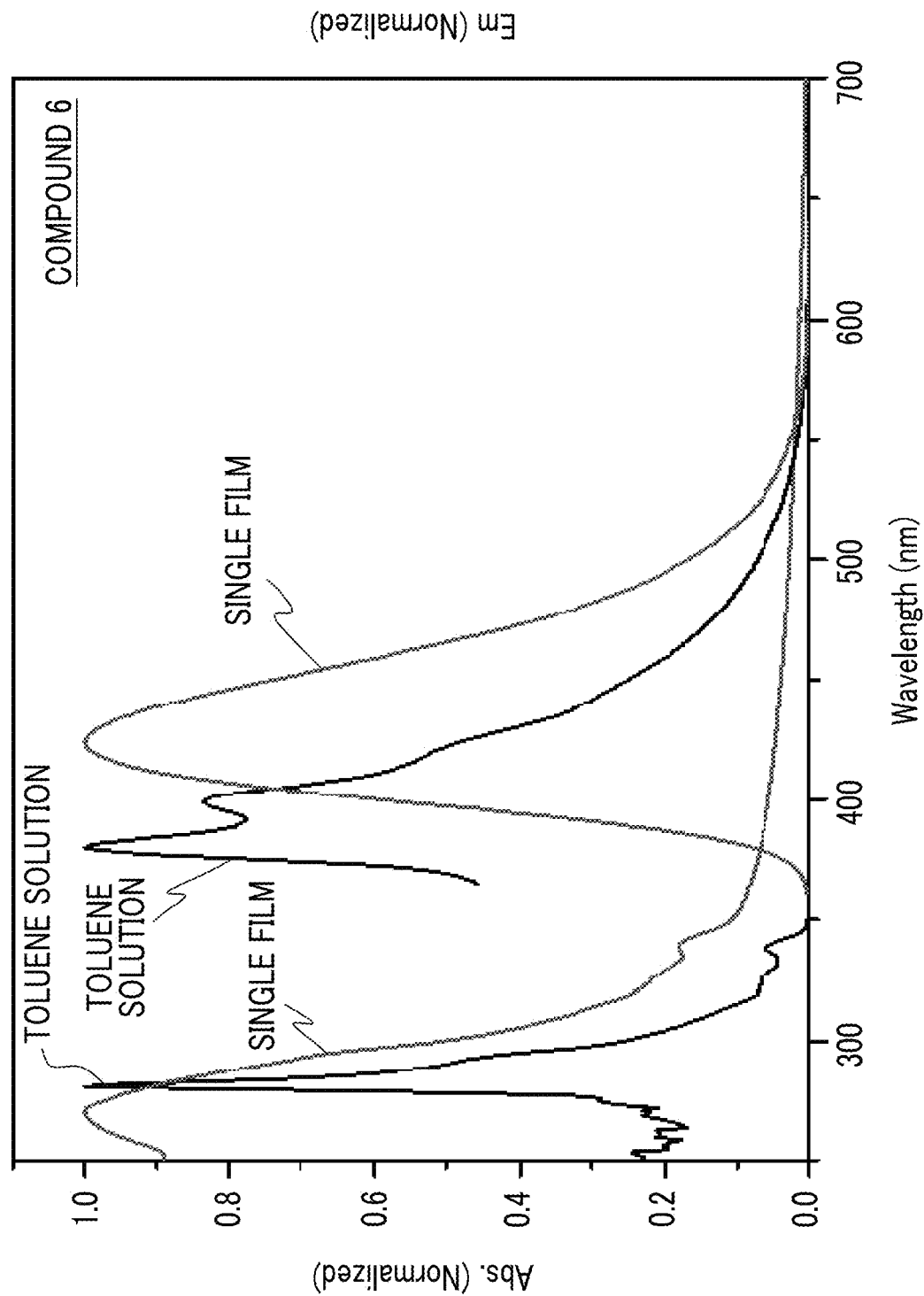
FIG. 12 illustrates light emission spectrums of a toluene solution and a single film of a compound 6.
Figure 13:
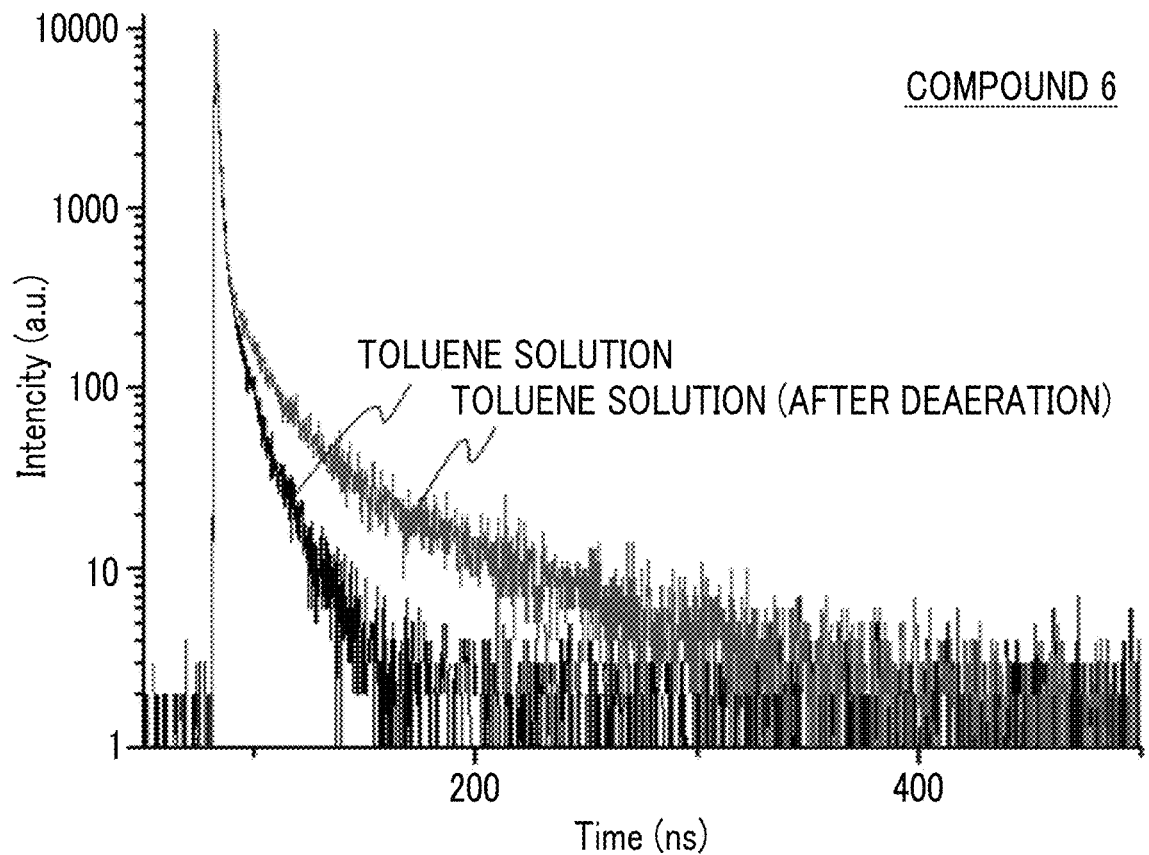
FIG. 13 illustrates an excess attenuation curve of light emission before and after degassing of the toluene solution of the compound 6.

With respect to the toluene solution and the single film of Compound 6, light emission spectrum and absorption spectrum measured by using 340 nm of excitation light are shown in FIG. 12. With respect to the toluene solution of Compound 6, excess attenuation curve of light emission measured by using 340 nm of excitation light and excess attenuation curve measured after degassing of the toluene solution are shown in FIG. 13. Photoluminescence quantum efficiency measured with respect to the toluene solution and the single film of Compound 6 and photoluminescence quantum efficiency measured after degassing of the toluene solution and the single film of Compound 6 are shown in Table 6.

TABLE 1

| | Compound 1 | | | | |
|---|---|---|---|---|---|
| | Toluene solution | Chloroform solution | Cyclohexane solution | Single film | Dope film |
| PL quantum efficiency | 2% | 2% | 1% | 38% | 46% |
| PL quantum efficiency (after degassing) | 72% | 13% | 10% | 74% | 78% |

TABLE 2

| | Compound 2 | | | | |
|---|---|---|---|---|---|
| | Toluene solution | Chloroform solution | Cyclohexane solution | Single film | Dope film |
| PL quantum efficiency | 10% | 12% | 1% | 30% | 45% |
| PL quantum efficiency (after degassing) | 20% | 53% | 2% | 50% | 62% |

TABLE 3

| | Compound 3 | | | | |
|---|---|---|---|---|---|
| | Toluene solution | Chloroform solution | Cyclohexane solution | Single film | Dope film |
| PL quantum efficiency | 2% | 2% | 1% | 34% | 36% |
| PL quantum efficiency (after degassing) | 36% | 23% | 8% | 41% | 60% |

TABLE 4

| | Compound 4 | | | | |
|---|---|---|---|---|---|
| | Toluene solution | Chloroform solution | Cyclohexane solution | Single film | Dope film |
| PL quantum efficiency | 10% | 4% | 5% | 10% | 23% |
| PL Quantum efficiency (after degassing) | 20% | 5% | 6% | 11% | 26% |

TABLE 5

| | Compound 5 | | | |
|---|---|---|---|---|
| | Toluene solution | Chloroform solution | Single film | Dope film |
| PL quantum efficiency | 1% | 1% | 6% | 22% |

TABLE 5-continued

| | Compound 5 | | | |
|---|---|---|---|---|
| | Toluene solution | Chloroform solution | Single film | Dope film |
| PL quantum efficiency (after degassing) | 6% | 4% | 8% | 24% |

TABLE 6

| | Compound 6 | |
|---|---|---|
| | Toluene solution | Single film |
| PL quantum efficiency | 1% | 4% |
| PL quantum efficiency (after degassing) | 2% | 4% |

As shown in FIGS. 3, 5, 7, 11, and 13, it was possible to observe a long-legged excess attenuation curve in any of the compounds. From this, it was possible to check that Compounds 1 to 6 are compounds that emit delayed fluorescence. In addition, from PL quantum efficiency after degassing shown in Tables 1 to 6, it was recognized that Compounds 1 to 6 have excellent light emission efficiency. It is estimated that regarding the one having low PL quantum efficiency among non-degassed each solution, the single film, the excited triplet state is extinguished by dissolved oxygen and generation of the excited singlet state via reverse intersystem crossing is reduced.

(Examples 7 and 8) Preparation and Evaluation of Organic Electroluminescence Element Using Compound 6

On a glass substrate on which an anode made of an indium tin oxide (ITO) having a film thickens of 100 nm was formed, each thin film was stacked at a degree of vacuum of $5 \times 10^{-5}$ Pa by a vacuum deposition method. First, HAT-CN was deposited at a thickness of 10 nm on the ITO to form a hole injection layer. Subsequently, TrisPCz was deposited at a thickness of 25 nm to form a hole transport layer, and thereon, mCBP or Compound 6 was deposited at a thickness of 5 nm to form an electron blocking layer. Subsequently, 4CzIPN and Compound 6 were co-deposited from different deposition sources, and a layer having a thickness of 30 nm was formed to make a light-emitting layer. At this time, a concentration of 4CzIPN was 20% by weight. Subsequently, Compound 6 was deposited at a thickness of 10 nm to form a hole blocking layer, and thereon, an electron transport material and Liq were co-deposited at a weight ratio of 7:3 at a thickness of 40 nm from different deposition sources to form an electron transfer layer. Subsequently, Liq and aluminum (Al) were co-deposited at a weight ratio of 2:100 at a thickness of 100 nm from different deposition sources to form a cathode, thereby preparing organic electroluminescence elements of Example 7 (electron blocking layer is mCBP) and Example 8 (electron blocking layer is Compound 6).

Figure 14:
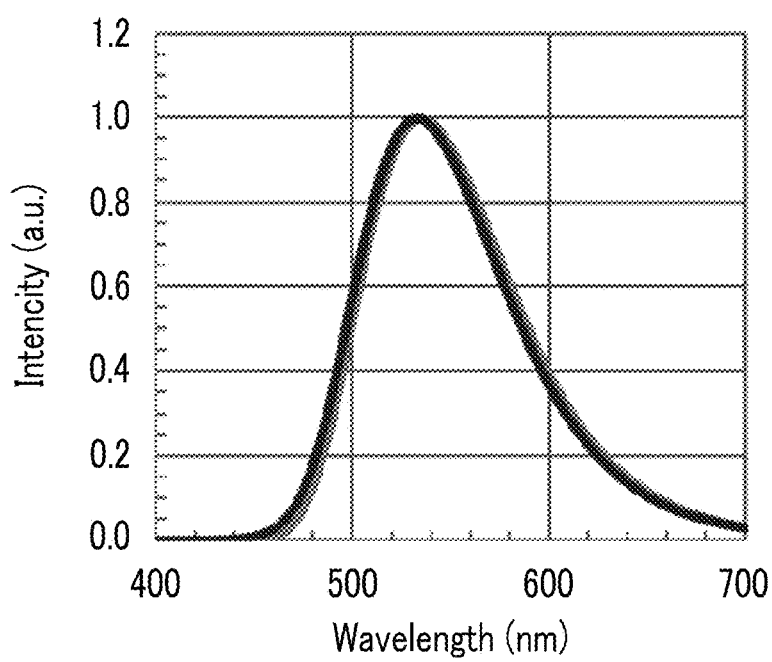
FIG. 14 illustrates a light emission spectrum of an organic electroluminescence element using the compound 6.

Light emission spectrum of each of the produced elements was overlapped as shown in FIG. 14. A maximum external quantum efficiency of Example 7 was 14%.

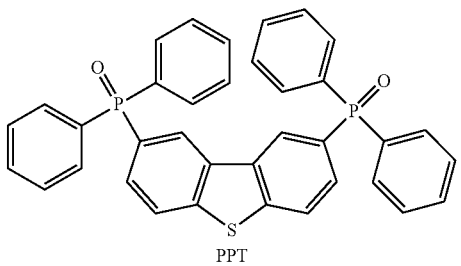
PPT

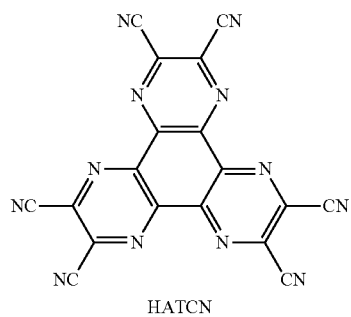
HATCN

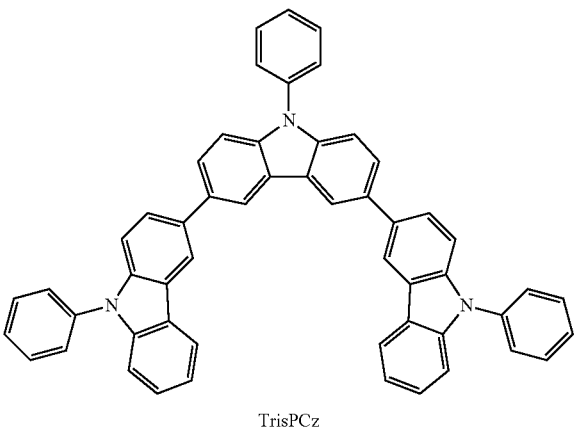
TrisPCz

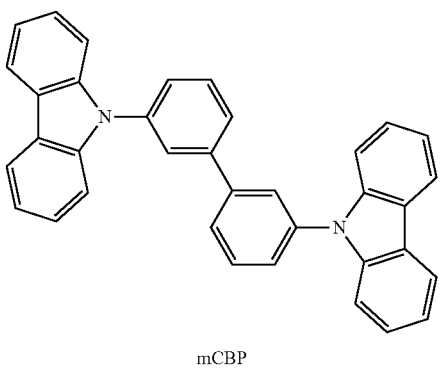
mCBP

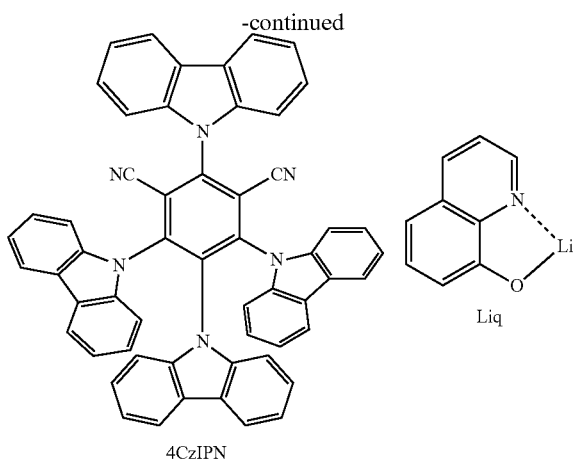

4CzIPN

INDUSTRIAL APPLICABILITY

The compounds of the present invention are useful as a light-emitting material and the like. For this reason, the compounds of the present invention are effectively used as a light-emitting material and the like for an organic light-emitting element such as an organic electroluminescence element. In the compounds of the present invention, those in which delayed fluorescence is emitted are contained, and thus it is also possible to provide an organic light-emitting element having high light emission efficiency. For this reason, the present invention has high industrial applicability.

REFERENCE SIGNS LIST

1 Substrate
2 Anode
3 Positive hole injection layer
4 Positive hole transport layer
0.5 Light-emitting layer
6 Electron transport layer
7 Cathode

The invention claimed is:

1. An organic light-emitting element comprising a compound represented by the following general formula (1):

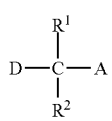

General formula (1)

wherein $R^1$ and $R^2$ each independently represent a fluorinated alkyl group, D represents a substituent in which Hammett's $\sigma_p$ value is negative, and A is represented by the following general formula (9):

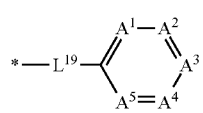

General formula (9)

wherein $L^{19}$ represents a substituted or non-substituted arylene group, or a substituted or non-substituted heteroarylene group; $A^1$ to $A^5$ each independently represent N or $C(R^{19})$ and at least one of $A^1$ to $A^5$ is N; and $R^{19}$ represents a hydrogen atom or a substituent.

2. The organic light-emitting element according to claim 1, wherein $R^1$ and $R^2$ each independently represent a perfluoroalkyl group.

3. The organic light-emitting element according to claim 1, wherein $R^1$ and $R^2$ each independently have 1 to 3 carbon atoms.

4. The organic light-emitting element according to claim 1, wherein D has a substituted or non-substituted diarylamino structure.

5. The organic light-emitting element according to claim 4, wherein D is an aryl group substituted with a substituted or non-substituted diarylamino group.

6. The organic light-emitting element according to claim 1, comprising the compound as a host material.

7. The organic light-emitting element according to claim 1, comprising the compound as a positive hole blocking material.

8. The organic light-emitting element according to claim 1, comprising the compound as an electron blocking material.

9. The organic light-emitting element according to claim 1, wherein a light-emitting layer includes the compound.

10. The organic light-emitting element according to claim 9, wherein the light-emitting layer contains the compound in an amount of less than 50% by weight, and the light-emitting layer contains a host material in addition to the compound.

11. The organic light-emitting element according to claim 9, wherein the light-emitting layer contains the compound in an amount of 50% or more by weight, and the light-emitting layer contains a light-emitting material in addition to the compound.

12. The organic light-emitting element according to claim 1, wherein an anode, a plurality of organic layers including a light-emitting layer, and a cathode are stacked in order, and the compound is included in a layer in contact with a cathode side of the light-emitting layer.

13. The organic light-emitting element according to claim 1, wherein the anode, the plurality of organic layers including a light-emitting layer, and the cathode are stacked in order, and the compound is included in a layer in contact with an anode side of the light-emitting layer.

14. The organic light-emitting element according to claim 1 that emits delayed fluorescence.

15. A compound represented by the general formula (1):

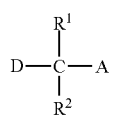

General formula (1)

wherein $R^1$ and $R^2$ each independently represent a fluorinated alkyl group, D represents an aryl group substituted with a substituted or non-substituted diarylamino group in which Hammett's $\sigma_p$ value is negative, and A is represented by the following general formula (9):

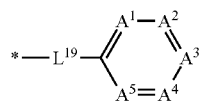
General formula (9)
wherein $L^{19}$ represents a substituted or non-substituted arylene group, or a substituted or non-substituted heteroarylene group; $A^1$ to $A^5$ each independently represent N or $C(R^{19})$ and at least one of $A^1$ to $A^5$ is N; and $R^{19}$ represents a hydrogen atom or a substituent.
* * * * *